(12) United States Patent
Nilsson

(10) Patent No.: US 9,713,634 B2
(45) Date of Patent: Jul. 25, 2017

(54) PROCESS FOR CONCENTRATION OF A POLYPEPTIDE

(71) Applicant: Shire Pharmaceuticals Ireland Limited, Dublin (IE)

(72) Inventor: Stefan Nilsson, Lidingö (SE)

(73) Assignee: Shire Pharmaceuticals Ireland Limited, Dublin (IE)

( * ) Notice: Subject to any disclaimer, the term of this patent is extended or adjusted under 35 U.S.C. 154(b) by 0 days.

(21) Appl. No.: 15/041,841

(22) Filed: Feb. 11, 2016

(65) Prior Publication Data

US 2016/0193304 A1    Jul. 7, 2016

Related U.S. Application Data

(62) Division of application No. 12/295,848, filed as application No. PCT/DK2007/000177 on Apr. 4, 2007, now abandoned.

(30) Foreign Application Priority Data

Apr. 4, 2006 (DK) ................................ 2006 00488
Jul. 5, 2006 (DK) ................................ 2006 00922

(51) Int. Cl.
| | |
|---|---|
| C12N 9/16 | (2006.01) |
| A61K 38/46 | (2006.01) |
| A61K 38/47 | (2006.01) |
| C07K 1/34 | (2006.01) |
| C07K 1/36 | (2006.01) |
| A61K 38/45 | (2006.01) |

(52) U.S. Cl.
CPC ............ *A61K 38/465* (2013.01); *A61K 38/45* (2013.01); *A61K 38/47* (2013.01); *C07K 1/34* (2013.01); *C07K 1/36* (2013.01); *C12Y 205/01061* (2013.01); *C12Y 301/06001* (2013.01); *C12Y 302/01024* (2013.01); *C12Y 302/01046* (2013.01); *C12Y 301/06008* (2013.01)

(58) Field of Classification Search
CPC ... C12N 9/16; C12Y 302/06008; A61K 38/00
USPC ....................................................... 435/196
See application file for complete search history.

(56) References Cited

U.S. PATENT DOCUMENTS

| | | |
|---|---|---|
| 6,197,507 B1 | 3/2001 | Berg et al. |
| 6,812,339 B1 | 11/2004 | Venter et al. |
| 7,232,670 B2 | 6/2007 | D'Azzo et al. |
| 8,536,315 B2 * | 9/2013 | Fogh ......................... C12N 9/16  435/196 |
| 2003/0199073 A1 | 10/2003 | Fogh et al. |
| 2004/0126370 A1 | 7/2004 | d'Azzo et al. |
| 2008/0003211 A1 | 1/2008 | Fogh et al. |
| 2009/0246187 A1 | 10/2009 | Nilsson |

FOREIGN PATENT DOCUMENTS

| | | |
|---|---|---|
| EP | 0456229 A2 | 11/1991 |
| JP | 2002-517516 A | 6/2002 |
| WO | WO-97/26369 A1 | 7/1997 |
| WO | WO-99/37325 A2 | 7/1999 |
| WO | WO-99/64462 A1 | 12/1999 |
| WO | WO-00/67789 A1 | 11/2000 |
| WO | WO-01/07065 A2 | 2/2001 |
| WO | WO-02/40686 A2 | 5/2002 |
| WO | WO-02/098455 A2 | 12/2002 |
| WO | WO-02/099092 A2 | 12/2002 |
| WO | WO-03/002731 A1 | 1/2003 |
| WO | WO-03/029403 A2 | 4/2003 |
| WO | WO-03/057179 A2 | 7/2003 |
| WO | WO-03/066669 A2 | 8/2003 |
| WO | WO 2005/073307 A1 | 8/2005 |
| WO | WO-2005/073367 A1 | 8/2005 |
| WO | WO-2005/094874 A1 | 10/2005 |
| WO | WO-2006/031560 A2 | 3/2006 |

OTHER PUBLICATIONS

Aronson, J.R. et al., Lysosomal degradation of Asn-linked glycoproteins, FASEB J., 3(14):2615-22 (1989).

Austin, J. et al., Abnormal sulphatase activities in two human diseases (metachromatic leucodystrophy and gargoylism), Biochem. J., 93(2):15C-17C (1964).

Author Not Known, Chapter 788: Particulate Matter in Injections, Methods 1 and 2, Revision Bulletin, The United States Pharmacopeial Convention, 3 pages (2012).

Author Not Known, Guidance for Industry: Immunogenicity Assessment for Therapeutic Protein Products [Draft], Clinical/Medical, U.S. Department of Health and Human Services, Food and Drug Administration, Center for Drug Evaluation and Research (CDER), and Center for Biologics Evaluation and Research (CBER), 34 pages (Feb. 2013).

Author Not Known, Guidance for Industry: Immunogenicity Assessment for Therapeutic Protein Products, Clinical/Medical, U.S. Department of Health and Human Services, Food and Drug Administration, Center for Drug Evaluation and Research (CDER), and Center for Biologics Evaluation and Research (CBER), 39 pages (Aug. 2014).

Author Not Known, Protein Purification Handbook, GE Healthcare, 96 pages (Oct. 2001).

Author Not Known, Recombinant Human Arylsulfatase A/ARSA, CF, Safety Data Sheet, R and D Systems, 3 pages (2012).

(Continued)

*Primary Examiner* — Tekchand Saidha

(74) *Attorney, Agent, or Firm* — Fangli Chen; Emily E. Bates; Proskauer Rose LLP

(57) ABSTRACT

The present invention comprises a method of concentrating a composition comprising a polypeptide of interest and the use of such concentrated composition for the treatment of diseases in mammals, in particular by subcutaneous injection.

9 Claims, No Drawings

(56) References Cited

OTHER PUBLICATIONS

Author Not Known, Recombinant Human Arylsulfatase A/ARSA, Material Safety Data Sheet, Version 1.1, Novoprotein, 2 pages (2013).
Baum, H. et al., The assay of arylsulphatases A and B in human urine, Clin. Chim. Acta., 4(3):453-5 (1959).
Ben-Yoseph, Y. et al., The Interrelations between High- and Low-Molecular-Weight Forms of Normal and Mutant (Krabbe-Disease) Galactocerebrosidase, Biochemistry Journal, 189:9-15, 1980.
Berg, T. et al., Purification and characterization of Recombinant Human Lysosomal a-mannosidase, Molecular Genetics and Metabolism, 73:18-29 (2001).
Bond, C.S. et al., Structure of a human lysosomal sulfatase, Structure, 5(2):277-289, (1997).
Bostick, W.D. et al., Separation and analysis of arylsulfatase isoenzymes in body fluids of man, Clin. Chem., 24(8):1305-16 (1978).
Branden et al., Introduction to Protein Structure, Garland Publishing Inc., New York, p. 247 (1991).
Braulke, T. et al., Insulin-like Growth Factors I and li Stimulate Endocytosis but Do Not Affect Sorting of Lysosomal Enzymes in Human Fibroblasts, The Journal of Biological Chemistry, 265(12):6650-6655 (1990).
Braulke, T. et al., Sulfated Oligosaccharides in Human Lysosomal Enzymes, Biochemical and Biophysical Research Communications, 143(1):178-185 (1987).
Chen Y.Q. And Wenger, D.A., Galactocerebrosidase from human urine: purification and partial characterization, Biochimica et Biophysica Acta, 1170:53-61 (1993).
Chen, S. et al., Production of Recombinant Proteins in Mammalian Cells, Current Protocols in Protein Science, 5(10):1-41 (1998).
Chothia, C. And Lesk, A.M., The relation between the divergence of sequence and structure in proteins, The EMBO Journal, 5(4):823-826 (1986).
Coenen, R. et al., Morphological alterations in the inner ear of the arylsulfatase A-deficient mouse, Acta Neuropathol., 101(5):491-8 (2001).
Cordoba-Rodriguez, R.V., Aggregates in MAbs and Recombinant Therapeutic Proteins: A Regulatory Perspective, BioPharm International, Advanstar Communications, Inc., 11 pages (2008), retrieved on Dec. 10, 2014 <https://license.icopyright.net/rights/downloadLicense.act?lid=ilvX2ex1CJU%3d>.
D'Hooge, R. et al., Hyperactivity, neuromotor defects, and impaired learning and memory in a mouse model for metachromatic leukodystrophy, Brain Res., 907(1-2):35-43 (2001).
Demeule, M. et al., High transcytosis of melanotransferrin (P97) across the blood-brain barrier, J. Neurochem., 83(4):924-33 (2002).
Dierks, T. et al., Conversion of cysteine to formylglycine: A protein modification in the endoplasmic reticulum, Proceedings of the National Academy of Science USA, 94:11963-11968 (1997).
Dunican, D.J. and Doherty, P., Designed Cell-Permeant Phosphopeptides to Modulate Intracellular Signaling Pathways, Biopolymers, 61(1):45-60 (2001).
Extended European Search Report for EP13167428.5, 6 pages (Sep. 2, 2013).
Farooqui, A.A. And Srivastava, P.N., Isolation, Characterization and the Role of Rabbit Testicular Arylsulphatase A in Fertilization, Biochemistry Journal, 181:331-337 (1979).
Fluharty, A.L. and Edmond, J., Arylsulfatases A and B from Human Liver, Meth. Enzymol. 50:537-547 (1978).
Franco, B. et al., A Cluster of Sulfatase Genes on Xp22.3: Mutations in Chondrodysplasia Punctata (CDPX) and Implications for Warfarin Ernbryopathy, Cell, 81:15-25 (1995).
GenBank Accession No. AAE33543.1 GI: 10056637, first referenced Sep. 1, 2000 (1 page).
GenBank Accession No. X52151.1, GI:28857, first referenced Dec. 4, 1992, updated Oct. 7, 2008 (2 pages).
Gieselmann, V. et al., Arylsulfatase A pseudodeficiency: Loss of a polyadenylylation signal and N-glycosylation site, Proceedings of the National Academy of Science USA, 86:9436-9440 (1989).
Gieselmann, V. et al., In vitro mutagenesis of potential N-glycosylation sites of arylsulfatase A. Effects on glycosylation, phosphorylation, and intracellular sorting, J. Biol. Chem., 267(19):13262-6 (1992).
Gieselmann, V. et al., Metachromatic leukodystrophy: consequences of sulphatide accumulation, Acta Paediatr. Suppl., 92(443):74-9 (2003).
Gieselmann, V. et al., Metachromatic leukodystrophy: molecular genetics and an animal model, J. Inherit. Metab. Dis., 21(5):564-74 (1998).
Hallmann, A. and Sumper, M., An inducible arylsulfatase of *Volvox carteri* with properties suitable for a reporter-gene system: Purification, characterization and molecular cloning, European Journal of Biochemistry, 221:143-150 (1994).
Hess, B. et al., Phenotype of arylsulfatase A-deficient mice: relationship to human metachromatic leukodystrophy, Proc. Natl. Acad. Sci. U S A., 93(25):14821-6 (1996).
Hess, G., Isolation and comparison of arylsulfatase A from rat liver and Morris hepatoma 7777, European Journal of Biochemistry, 135:505-509 (1983).
Hift. R.J. et al., Variegate porphyria in South Africa, 1688-1996—new developments in an old disease, S. Afr. Med. J., 87(6):722-31 (1997).
Ho, A. et al., Synthetic Protein Transduction Domains: Enhanced Transduction Potential in Vitro and in Vivo, Cancer Research, 61:474-477 (2001).
Ida, H. et al., Pathological and biochemical studies of fetal Krabbe disease, Brain & Development, 16:480-484 (1994).
International Preliminary Report on Patentability for PCT/DK2007/000177, 15 pages (Nov. 21, 2008).
International Search Report for PCT/DK2007/000177, 5 pages (Jan. 17, 2008).
James, G.T., Essential Arginine Residues in Human Liver Arylsulfatase AU, Archives of Biochemistry and Biophysics, 197(1):57-62 (1979).
Jordan, P.M. et al., Purification, crystallization and properties of porphobilinogen deaminase from a recombinant strain of *Escherichia coli* K12, Biochemistry, 254:427-435 (1988).
Kakkis et al., Abstract only, Abstract No. 281-0, A method to reduce the immune response to enzyme replacement therapy: Studies of criteria for success, J. Inherit. Metab. Dis., vol. 26, Supple 2 (2003).
Kakkis et al., Abstract only, Abstract No. 282-0, Effective reduction of lysosomal storage in brain and meninges following intrathecal administration of iduronidase in canine mucopolysaccharidosis I (MPS I), J. Inherit. Metab. Dis., vol. 26, Supple 2 (2003).
Kaneda, Y. et al., Regional assignment of five genes on human chromosome 19, Chromosoma, 95(1):8-12 (1987).
Kelly, B.M. et al., Presence of a lysosomal enzyme, arylsulfatase-A, in the prelysosome-endosome compartments of human cultured fibroblasts, European Journal of Cell Biology, 48:71-78 (1989).
Kudoh, T. and Wenger, D.A., Diagnosis of metachromatic leukodystrophy, Krabbe disease, and Farber disease after uptake of fatty acid-labeled cerebroside sulfate into cultured skin fibroblasts, J. Clin. Invest., 70(1):89-97 (1982).
Lee, G.D. and Van Etten, R.L., Evidence for an Essential Histidine Residue in Rabbit Liver Aryl Sulfatase A, Archives of Biochemistry and Biophysics, 171:424-434 (1975).
Liao, Y.F. et al., Cloning, expression, purification, and characterization of the human broad specificity lysosomal acid alpha-mannosidase. J. Biol. Chem., 271(45):28348-58 (1996).
Lindgren, M. et al., Cell-penetrating peptides, TiPS, 21:99-103 (2000).
Lukatela, G. et al., Crystal structure of human arylsulfatase A: the aldehyde function and the metal ion at the active site suggest a novel mechanism for sulfate ester hydrolysis, Biochemistry, 37(11):3654-64 (1998).
Lüllmann-Rauch, R. et al., Lysosomal sulfoglycolipid storage in the kidneys of mice deficient for arylsulfatase A (ASA) and of double-knockout mice deficient for ASA and galactosylceramide synthase, Histochem. Cell Biol., 116(2):161-9 (2001).

(56) References Cited

OTHER PUBLICATIONS

Matsushima, G.K. et al., Absence of MHC class II molecules reduces CNS demyelination, microglial/macrophage infiltration, and twitching in murine globoid cell leukodystrophy, Cell, 78(4):645-56 (1994).
Matzner, U. et al., Bone marrow stem cell-based gene transfer in a mouse model for metachromatic leukodystrophy: effects on visceral and nervous system disease manifestations, Gene. Ther. 9(1):53-63 (2002).
Matzner, U. et al., Enzyme replacement improves nervous system pathology and function in a mouse model for metachromatic leukodystrophy, Human Molecular Genetics, 14:1139-1152 (2005).
Matzner, U. et al., Long-term expression and transfer of arylsulfatase A into brain of arylsulfatase A-deficient mice transplanted with bone marrow expressing the arylsulfatase A cDNA from a retroviral vector, Gene Ther., 7(14):1250-7 (2000).
Matzner, U. et al., Retrovirally expressed human arylsulfatase A corrects the metabolic defect of arylsulfatase A-deficient mouse cells, Gene Ther., 7(9):805-12 (2000).
Meissner, P. et al., Allosteric inhibition of human lymphoblast and purified porphobilinogen deaminase by protoporphyrinogen and coproporphyrinogen, A possible mechanism for the acute attack of variegate porphyria, J. Clin. Invest., 91(4):1436-44 (1993).
Meissner, P.N. et al., Protoporphyrinogen oxidase and porphobilinogen deaminase in variegate porphyria, Eur. J. Clin. Invest., 16(3):257-61 (1986).
Millipore, Protein Concentration and Diafiltration by Tangential Flow Filtration, Millipore Corporation, Billerica, MA, 01821. USA. 2003.
Muschol, N. et al., Secretion of phosphomannosyl-deficient arylsulphatase A and cathepsin D from isolated human macrophages, Biochem. J., 368(Pt 3):845-53 (2002).
Nebes, V.L. and Schmidt, M.C., Human lysosomal alpha-mannosidase: isolation and nucleotide sequence of the full-length cDNA, Biochem. Biophys. Res. Commun., 200(1):239-45 (1994).
Nilssen, O. et al., alpha-Mannosidosis: functional cloning of the lysosomal alpha-mannosidase cDNA and identification of a mutation in two affected siblings, Hum. Mol. Genet., 6(5):717-26 (1997).
Pan, W. and Kastin, A,J. Upregulation of the transport system for TNFalpha at the blood-brain barrier, Arch. Physiol. Biochem., 109(4):350-3 (2001).
Pan, W. and Kastin, A.J., TNFalpha transport across the blood-brain barrier is abolished in receptor knockout mice, Exp. Neurol., 174(2):193-200 (2002).
Pearson, W.R. and Lipman, D.J., Improved tools for biological sequence comparison, Proceedings of the National Academy of Science USA, 85:2444-2448 (1988).
Pearson, W.R., Rapid and Sensitive Sequence Comparison with FASTP and FASTA, Methods of Enzymology, 183:63-98 (1990).
Perusi, C. et al., A novel mutation which represents the fifth non-pathogenic polymorphism in the coding sequence of the Arylsulfatase A gene, Molecular and Cellular Probes, 2:449-451 (1997).
Peters, C. et al., Phylogenetic Conservation of Arylsulfatases, The Journal of Biological Chemistry, 265(6):3374-3381 (1990).
Pohl, T., Concentration of Proteins and Removal of Solutes, Methods in Enzymology, 182:68-83 (1990).
Rafi, M.A. et al., Disease-causing mutations in cis with the common arylsulfatase A pseudodeficiency allele compound the difficulties in accurately identifying patients and carriers of metachronnatic leukodystrophy, Molecular Genetics and Metabolism, 79:83-90 (2003).
Ricketts, M.H. et al., The R496H Mutation of Arylsulfatase A Does Not Cause Metachromatic Leukodystrophy, Human Mutation, 12:238-239 (1998).
Riise, H.M. et al., Genomic structure of the human lysosomal alpha-mannosidase gene (MANB), Genomics, 42(2):200-7 (1997).
Rodman, T.C. et al., Circulating natural IgM antibodies and their corresponding human cord blood cell-derived Mabs specifically combat the Tat protein of HIV, Exp. Hematol., 29(8):1004-9 (2001).
Rothenberger, S. et al., Coincident expression and distribution of melanotransferrin and transferrin receptor in human brain capillary endothelium, Brain Res., 712(1):117-21 (1996).
Sakai, N. et al., Purification and Characterization of Galactocerebrosidase from Human Lymphocytes, Journal of Biochemistry, 116(3):615-620 (1994).
Sandhoff, R. et al., Kidney sulfatides in mouse models of inherited glycosphingolipid disorders: determination by nano-electrospray ionization tandem mass spectrometry, J. Biol. Chem., 277(23):20386-98 (2002).
Sangalli, A. et al., Transduced fibroblasts and metachromatic leukodystrophy lymphocytes transfer arylsulfatase A to myelinating glia and deficient cells in vitro, Hum. Gene. Ther., 9(14):2111-9 (1998).
Sarafian, T.A. et al., Studies on the charge isomers of arylsulfatase A, Biochem. Med., 33(3):372-80 (1985).
Schmidt, B. et al., A Novel Amino Acid Modification in Sulfatases That is Defective in Multiple Sulfatase Deficiency, Cell, 82:271-278 (1995).
Schuchman, E.H. et al., Human Arylsulfatase B: MOPAC Cloning, Nucleotide Sequence of a Full-Length cDNA, and Regions of Amino Acid Identity with Arylsulfatases A and C, Genomics, 6:149-158 (1990).
Schwarze, S.R. et al., Protein transduction: unrestricted deliver into all cells?, Trends in Cell Biology, 10:290-295 (2000).
Scott, J.E. And Dorling, J., Differential staining of acid glycosaminoglycans (mucopolysaccharides) by alcian blue in salt solutions, Histochemie, 5(3):221-33 (1965).
Selmer, T. et al., The evolutionary conservation of a novel protein modification, the conversion of cysteine to serinesemialdehyde in arylsulfatase from Volttox carterr, European Journal Biochemistry, 238:341-345 (1996).
Sevin, C. et al., Intracerebral adeno-associated virus-mediated gene transfer in rapidly progressive forms of metachromatic leukodystrophy, Human Molecular Genetics, 15(1):53-64 (2006).
Shire, S.J. et al., Challenges in the Development of High Protein Concentration Formulations, Journal of Pharmaceutical Sciences, 93(6):1390-1402 (2004).
Sofer, G., Preparation chromatographic separations in pharmaceutical, diagnostic, and biotechnology industries: current and future trends, Journal of Chromatography A., 707(1):23-28 (1995).
Sommerlade, H.J. et al., Four monoclonal antibodies inhibit the recognition of arylsulphatase A by the lysosomal enzyme phosphotransferase, Biochem. J., 297 ( Pt 1):123-30 (1994).
Stein, C. et al., Cloning and expression of human arylsulfatase A, J. Biol. Chem., 264(2):1252-9 (1989).
Stevens, R.L. et al., Purification and Properties of Arylsulfatase A from Human Urine, The Journal of Biological Chemistry, 250(7):2495-2501, (1975).
Thompson, J.D. et al., Clustal W: improving the sensitivy of progressive multiple sequence alignment through sequence weighting, position-specific gap penalties and weight matrix choice, Nucleic Acids Research, 22(22):4673-4680 (1994).
Tollersrud, O.K. et al., Purification of bovine lysosomal a-mannosidase, characterization of its gene and dtermination of two mutations that cause a-mannosidosis, European Journal of Biochemistry, 246:410-419 (1997).
Treuheit, M.J. et al., Inverse Relationship of Protein Concentration and Aggregation, Pharmaceutical Research, 19(4):511-516 (2002).
Wada, R. et al., Microglial activation precedes acute neurodegeneration in Sandhoff disease and is suppressed by bone marrow transplantation, Proc. Natl. Acad. Sci. U S A, 97(20):10954-10959 (2000).
Waheed, A. and Van Etten, R.L., Phosphorylation and sulfation of arylsulfatase A accompanies biosynthesis of the enzyme in normal and carcinoma cell lines, Biochimica et Biophysica Acta, 847:53-61 (1985).
Wang, J. et al., Neutralizing antibodies to therapeutic enzymes: considerations for testing, prevention and treatment, Nat. Biotechnol., 26(8):901-8 (2008).
Wang, M. et al., Erythropoietin Production from CHO Cells Grown by Continuous Culture in a Fluidized-Bed Bioreactor, Biotechnology Bioengineering, 77(2):194-203 (2002).

(56) References Cited

OTHER PUBLICATIONS

Wang, W., Protein aggregation and its inhibition in biopharmaceutics, Int. J. Pharm., 289(1-2):1-30 (2005).

Wittke, D. et al., Lysosomal sulfatide storage in the brain of arylsulfatase A-deficient mice: cellular alterations and topographic distribution, Acta Neuropathol, 108:261-271 (2004).

Written Opinion for PCT/DK2007/000177, 10 pages (Jan. 17, 2008).

Wu, D. and Pardridge, W.M., Neuroprotection with noninvasive neurotrophin delivery to the brain, Proc. Natl. Acad. Sci. U S A, 96(1):254-9 (1999).

Yao, J.K. and Rastetter, G.M., Microanalysis of complex tissue lipids by high-performance thin-layer chromatography, Anal. Biochem., 150(1):111-6 (1985).

Zielasek, J. et al., Functional abnormalities in P0-deficient mice resemble human hereditary neuropathies linked to P0 gene mutations, Muscle Nerve, 19(8):946-52 (1996).

\* cited by examiner

PROCESS FOR CONCENTRATION OF A POLYPEPTIDE

RELATED APPLICATIONS

The present application is a division of U.S. patent application Ser. No. 12/295,848, a National Stage Entry of International Patent Application No. PCT/DK2007/000177, filed on Apr. 4, 2007, which claims priority to, and benefit of, DK PA 2006 00488 (filed on Apr. 4, 2006) and DK PA 2006 00922 (filed on Jun. 5, 2006), the entire contents of each of which are herein incorporated by reference.

SEQUENCE LISTING

The present specification makes reference to a Sequence Listing (submitted electronically as a .txt file named "2006685-1355 Sequence Listing" on Feb. 11, 2016). The .txt file was generated on Feb. 11, 2016 and is 85 kilobytes in size. The entire contents of the Sequence Listing are herein incorporated by reference.

FIELD OF THE INVENTION

The present invention relates to a method for concentrating a polypeptide of interest, to the use of a composition comprising a concentrated polypeptide of interest as a medicament for subcutaneous injection and to a composition comprising at least 10 mg/ml polypeptide of interest.

BACKGROUND OF THE INVENTION

Some polypeptides are useful as a medicament for the prevention and/or treatment of certain diseases. The ability to inject a medicament subcutaneously is an advantage as it makes it easy for the patients to administer the medication to themselves.

As there are physiological restrains on how large a volume it is possible to inject subcutaneously. Thus it is an advantage for medicaments which are to be administered subcutaneously that they are available in a high concentration so as to ensure that the patient receives an adequate amount of the medicament and/or to avoid multiple subcutaneous injections.

WO 99/37325 discloses methods of treating and preventing disease caused by absence or deficiency of the activity of enzymes belonging to the heme biosynthetic pathway. WO 03/002731 discloses a process for purification of recombinant porphobilinogen deaminase on an industrial scale and to the use of the purified product for the preparation of a medicament. Similarly, WO 02/099092 and WO 2005/094874 provides lysosomal alpha-mannosidase and therapeutic use hereof. Finally, WO 2005/073367 provides a process for purification of aryl sulfatase A and use of the enzyme in the treatment of metachromatic leukodystrophy.

The present invention relates to a method for concentrating a polypeptide of interest and to the use of a composition comprising a concentrated polypeptide of interest for the manufacture of a medicament for subcutaneous injection into mammal.

SUMMARY OF THE INVENTION

The present invention relates in one aspect to a method of concentrating a composition comprising a polypeptide of interest comprising:

a) Centrifugation and/or filtration of a composition comprising a polypeptide of interest
b) Concentrating the supernatant or retentate, respectively, obtained from step a).

In another aspect the present invention relates to a composition comprising at least 10 mg/ml polypeptide of interest.

In yet another aspect the present invention relates to use of a composition comprising 75-250 mg/ml polypeptide of interest for the manufacture of a medicament for subcutaneous injection into a mammal.

In yet another aspect the present invention relates to a method of treating a mammal for Acute Intermittent *Porphyria* comprising injecting subcutaneously a composition of 500-300 mg/ml PBGD.

In yet another aspect the present invention relates a method of treating a mammal for metachromatic leukodystrophy comprising subcutaneous injection of a composition of 50-300 mg/ml aryl sulfatase A.

In yet another aspect the present invention relates a method of treating a mammal for the lysosomal storage disorder alpha-mannosidosis comprising subcutaneous injection of a composition of 50-300 mg/ml lysosomal alpha-mannosidase.

In yet another aspect the present invention relates a method of treating a mammal for Krabbe disease comprising subcutaneous injection of a composition of 50-300 mg/ml galactosylcerebrosidase.

DEFINITIONS

For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA.

Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Multiple alignments of protein sequences may be made using "ClustalW" (Thompson, J. D., Higgins, D. G, and Gibson, T J. (1994) CLUSTAL W: improving the sensitivity of progressive multiple sequence alignment through sequence weighting, positions-specific gap penalties and weight matrix choice. Nucleic Acids Research, 22:4673-4680). Multiple alignment of DNA sequences may be done using the protein alignment as a template, replacing the amino acids with the corresponding codon from the DNA sequence.

In the context of the present invention, the term "E. C." (Enzyme Class) refers to the internationally recognized enzyme classification system, Recommendations of the Nomenclature Committee of the International Union of Biochemistry and Molecular Biology, Academic Press, Inc.

The term "origin" used in the context of amino acid sequences, e.g. proteins, or nucleic acid sequences is to be understood as referring to the organism from which it derives. Said sequence may be expressed by another organism using gene technology methods well known to a person skilled in the art. This also encompasses sequences which have been chemically synthesized. Furthermore, said sequences may comprise minor changes such as codon optimization, i.e. changes in the nucleic acid sequences which do not affect the amino acid sequence.

DETAILED DESCRIPTION OF THE INVENTION

Polypeptide of Interest

The polypeptide of the present invention may in particular be a hormone or hormone variant, an enzyme, a receptor or portion thereof, an antibody or portion thereof, an allergen or a reporter. The polypeptide of interest may in particular be an enzyme selected from one of six major enzyme groups, such as an oxidoreductase (E.C. 1), a transferase (E.C. 2), a hydrolase (E.C. 3), a lyase (E.C. 4), an isomerase (E.C. 5), or a ligase (E.C. 6). In a more particular aspect, the polypeptide of interest may be an aminopeptidase, amylase, carbohydrase, carboxypeptidase, catalase, cellulase, cellobiohydrolase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, xylanase, or beta-xylosidase.

The polypeptide of interest may in particular be a polypeptide which is useful as a medicament.

Examples of a suitable polypeptide of interest include but is not limited to one selected from the group consisting of a phorphobilinogen deaminase, an aryl sulfatase, an alpha-mannosidase and a galactocerebrosidase.

In principle a polypeptide of interest derivable from any source may be treated according to the methods of the present invention.

In a particular embodiment the polypeptide of interest may be of human origin. Especially in the context of using a polypeptide of interest for the manufacture of a medicament which is to be administered to humans may the polypeptide be of human origin as this may minimize the risk of unwanted allergic reactions. Natural variations of human polypeptide due to e.g. polymorphism are in the context of the present invention included in the term "human origin".

The polypeptide of interest may in particular be produced as a recombinant protein, i.e. a nucleotide sequence encoding the polypeptide of interest may be introduced into a cell for expression of the polypeptide of interest. The recombinant expression may be homologous or heterologous, i.e. the polypeptide of interest may be expressed in cell which it is naturally expressed by (homologous expression) or it may be expressed by a cell which it is not naturally expressed by (heterologous expression).

The recombinant polypeptide of interest may be expressed by any cell suitable for recombinant production of the particular polypeptide of interest. Examples of suitable cells include but are not limited to prokaryotic cells, such as an *E. coli* cell or a *Bacillus* cell. Examples of suitable eukaryotic cells include but are not limited to a yeast cell or a mammalian cell such as a Chinese Hamster Ovary (CHO). Alternatively, it may be a human cell.

Suitable host cells for the expression of glycosylated polypeptide are derived from multicellular organisms. Examples of invertebrate cells include plant and insect cells.

However, the host cell may also be a vertebrate cell, and propagation of vertebrate cells in culture (tissue culture) has become a routine procedure The term "recombinant polypeptide" or "recombinant polypeptide of interest" denotes herein a recombinant produced polypeptide.

Reference to a particular polypeptide of interest includes in the context of the present invention also functionally equivalent parts or analogues of the polypeptide of interest. For example, if the polypeptide of interest is an enzyme a functionally equivalent part of the enzyme could be a domain or subsequence of the enzyme which includes the necessary catalytic site to enable the domain or subsequence to exert substantially the same enzymatic activity as the full-length enzyme or alternatively a gene coding for the catalyst. The term "substantially the same enzymatic activity" refers to an equivalent part or analogue having at least 50%, preferably at least 60%, more preferably at least 70%, more preferably at least 75%, more preferably at least 80%, more preferably at least 85%, more preferably at least 90%, more preferably at least 95% and most preferably at least 97° k, at least 98% or at least 99% of the activity of the natural enzyme. An example of an enzymatically equivalent analogue of the enzyme could be a fusion protein which includes the catalytic site of the enzyme in a functional form, but it can also be a homologous variant of the enzyme derived from another species. Also, completely synthetic molecules that mimic the specific enzymatic activity of the relevant enzyme would also constitute "enzymatic equivalent analogues".

Generally, the skilled person will be able to readily devise appropriate assays for the determination of enzymatic activity. For PBGD, however, a suitable assay is described in WO 03/002731, in example 2, as well as in the experimental sections of the present applications. Aryl sulfhatase, in addition to its natural substrates, is also able to catalyze the hydrolysis of the synthetic, chromogenic substrate, para-Nitrocatechol sulfate (pNCS). The product, para-Nitrocatechol (pNC), absorbs light at 515 nm. An assay for determination of aryl sulfatase activity is described in details in WO 2005/073367 and in Fluharty et al. 1978, Meth. Enzymol. 50:537-47. For LAMAN, an appropriate enzyme activity assay is disclosed in WO 02/099092.

Porphobilinogen Deaminase

In one embodiment the polypeptide of interest of the invention may be porphobilinogen deaminase, (also known as porphobilinogen ammonia-lyase (polymerizing)), E.C. 4.3.1.8. (Waldenström 1937, J. Acta. Med. Scand. Suppl. 8). Porphobilinogen deaminase is the third enzyme in the heme biosynthetic pathway. E.C. 4.3.1.8 has been transferred to E.C. 2.5.1.61, so porphobilinogen deaminase (PBGD) is now placed under this E.C. number.

Porphobilinogen deaminase catalyzes the reaction of 4 porphobilinogen+$H_2O$=hydroxymethylbilane+4 $NH_3$.

PBDG is important in relation to Acute intermittent *porphyria* (AIP), which is an autosomal dominant disorder in man caused by a defect (50% reduction of activity) of PBDG (see WO01/07065 for further details in relation to this).

Porphobilinogen deaminase is in short known as PBGD and in the context of the present invention these two terms may be used inter-changeably with one another.

For recombinant expression of PBGD a host cell may in particular be a yeast cell or an *E. coli* cell.

For a detailed example of construction of a recombinant *E. coli* cell reference is made to example 1 of WO01/07065 and for construction of recombinant HeLa cells and NIH 3T3 cells capable of expressing mouse PBGD reference is made to example 6 of WO01/07065.

The term "recombinant porphobilinogen deaminase (rPBGD)" denotes herein a recombinant produced PBGD. In the following, this enzyme and the recombinant human form will be termed "PBGD" and "rhPBGD", respectively. Within this term is also included an enzymatically equivalent part or analogue of PBGD. One example of an enzymatically equivalent part of the enzyme could be a domain or subsequence of the enzyme which includes the necessary catalytic site to enable the domain or subsequence to exert substantially the same enzymatic activity as the full-length enzyme or alternatively a gene coding for the catalyst. The term "substantially the same enzymatic activity" refers to an equivalent part or analogues enzyme having at least 50%, preferably at least 60%, more preferably at least 70%, more preferably at least 75%, more preferably at least 80%, more preferably at least 85%, more preferably at least 90%, more preferably at least 95% and most preferably at least 97%, at least 98% or at least 99% of the activity of natural human rhPBGD measured in the rhPBGD activity assay described in example 2 of WO 03/002731. An example of an enzymatically equivalent analogue of the enzyme could be a fusion protein which includes the catalytic site of the enzyme in a functional form, but it can also be a homologous variant of the enzyme derived from another species. Also, completely synthetic molecules that mimic the specific enzymatic activity of the relevant enzyme would also constitute "enzymatic equivalent analogues".

An example of PBGD which may be used in the present invention includes any of those shown in Sequence 1-10 of the present application, or in Genebank no. X04217, X04808 or M95623.

Aryl Sulfatase

In another embodiment of the present invention the polypeptide of interest may be an arylsulfatase A.

Arylsulfatase A catalyzes the reaction of a cerebroside 3-sulfate+H2O=a cerebroside+sulphate.

ASA has been purified from a variety of sources including human liver, placenta, and urine. It is an acidic glucoprotein with a low isoelectric point. Above pH 6.5, the enzyme exists as a dimer with a molecular weight of approximately 110 kDa. ASA undergoes a pH-dependent polymerisation forming an octamer at pH 4.5. In human urine, the enzyme consists of two nonidentical subunits of 63 and 54 kDa. ASA purified from human liver, placenta, and fibroblasts also consist of two subunits of slightly different sizes varying between 55 and 64 kDa. As in the case of other lysosomal enzymes, ASA is synthesised on membrane-bound ribosomes as a glycosylated precursor. It then passes through the endoplasmic reticulum and Golgi, where its N-linked oligosaccharides are processed with the formation of phosphorylated and sulfated oligosaccharide of the complex type (Waheed A et al. Biochim Biophys Acta. 1985, 847, 53-61, Braulke T et al. Biochem Biophys Res Commun. 1987, 143, 178-185). In normal cultured fibroblasts, a precursor polypeptide of 62 kDa is produced, which translocates via mannose-6-phosphate receptor binding (Braulke T et al. J Biol Chem. 1990, 265, 6650-6655) to an acidic prelysosomal endosome (Kelly B M et al. Eur J Cell Biol. 1989, 48, 71-78).

The arylsulfatase A may in particular be of human origin. The length (18 amino acids) of the human ASA signal peptide is based on the consensus sequence and a specific processing site for a signal sequence. Hence, from the deduced human ASA cDNA (EMBL GenBank accession numbers 304593 and X521151) the cleavage of the signal peptide should be done in all cells after residue number 18 (Ala), resulting in the mature form of the human ASA. In the following, recombinant arylsulfatase A will be abbreviated rASA, the mature form of arylsulfatase A including the mature form of human ASA will be termed "mASA" and the mature recombinant human ASA will be termed "mrhASA".

A protein modification has been identified in two eukaryotic sulfatases (ASA and arylsulfatase B (ASB)) and for one from the green alga *Volvox carteri* (Schmidt B et al. Cell. 1995, 82, 271-278, Selmer T et al. Eur J Biochem. 1996, 238, 341-345). This modification leads to the conversion of a cysteine residue, which is conserved among the known sulfatases, into a 2-amino-3-oxopropionic acid residue (Schmidt B et al. Cell. 1995, 82, 271-278). The novel amino acid derivative is also recognised as C*-formylglycin (FGly). In ASA and ASB derived from MSD cells, the Cys-69 residue is retained. Consequently, it is proposed that the conversion of the Cys-69 to FGly-69 is required for generating catalytically active ASA and ASB, and that deficiency of this protein modification is the cause of MSD. Cys-69 is referred to the precursor ASA which has an 18 residue signal peptide. In the mASA the mentioned cysteine residue is Cys-51. Further investigations have shown that a linear sequence of 16 residues surrounding the Cys-51 in the mASA is sufficient to direct the conversion and that the protein modification occurs after or at a late stage of co-translational protein translocation into the endoplasmic reticulum when the polypeptide is not yet folded to its native structure (Dierks T et al. Proc Natl Acad Sci. 1997, 94, 11963-1196, Wittke, D. et al. (2004), Acta Neuropathol. (Berl.), 108, 261-271).

Multiple forms of ASA have been demonstrated on electrophoresis and isoelectric focusing of enzyme preparations from human urine, leukocytes, platelets, cultured fibroblasts and liver. Treatment with endoglycosidase H, sialidase, and alkaline phosphatase reduces the molecular size and complexity of the electrophoretic pattern, which suggests that much of the charge heterogeneity of ASA is due to variations in the carbohydrate content of the enzyme.

The arylsulfatase A may in particular be a form of arylsulfatase A, which is capable of crossing the blood brain barrier and/or a form of rASA, which possesses specific tags for entry into target cells within the brain. In particular, it may be a rASA, which is efficiently endocytosed in vivo via the mannose-6-phosphate pathway.

Thus the ASA may in particular be covalently bound to a so-called tag, peptides or proteins as vehicles or toxins as vehicles which are capable of increasing and/or facilitating transport of ASA over the blood-brain barrier and/or across cellular membranes in general (Schwarze et al., Trends Cell Biol. 2000; 10(7): 290-295; Lindgren et al., Trends Pharmacol. Sci. 2000; 21(3): 99-103). An ASA molecule containing such peptide sequences can be produced by expression techniques. The protein transduction process is not cell type specific and the mechanism by which it occurs is not fully elucidated, however, it is believed that it takes place by some sort of membrane perturbation and penetration process that is receptor independent. A partially unfolded state of the molecule may facilitate the process but is not essential.

An example of a suitable tag includes but is not limited to the mannose-6-phosphate tag.

Examples of peptides or proteins as vehicle include but are not limited to so-called protein-transducing domains. Examples of suitable protein-transducing domains include but are not limited to those mentioned in WO 2005/073367, which is incorporated herein by reference. Hence the protein-transducing domain may be the 11 residue basic peptide from the HIV TAT protein-YGRKKRRQRRR (Schwarze et al., Trends Cell Biol. 2000; 10(7): 290-295), a synthetic version of TAT-YARAAARQARA that confers more alpha-helicity and amphipathic nature to the sequence (Ho et al., Cancer Res. 2001; 61(2):474-477), a synthetic leader peptide composed of poly-R or a mixture of basic -R and -K residues in combination with other amino acids and peptides based on hydrophobic signal sequence moieties from either beta-3 integrin or Kaposi's sarcoma FGF (Dunican et al. Biopolymers 2001; 60(1): 45-60).

Examples of suitable toxins as vehicles include but are not limited to those described in WO 2005/073367, which is incorporated herein by reference.

The ASA may in particular comprise a nucleic acid sequence, which encodes:
(a) the amino acid sequence of SEQ ID NO:2 in WO 2005/073367;
(b) a portion of the sequence in (a), which is enzymatically equivalent to recombinant human arylsulfatase A
(c) an amino acid sequence analogue having at least 75% sequence identity to any one of the sequences in (a) or (b) and at the same time comprising an amino acid sequence, which is enzymatically equivalent to recombinant human arylsulfatase A.

In the present context, an amino acid sequence or a portion of an amino acid sequence which is a polypeptide capable of hydrolysing an amount of the arylsulfatase A substrate pNCS at 37° C. a rate corresponding to a specific activity of at least 20 U/mg polypeptide (preferably 50 U/mg polypeptide) when determined in an assay for measuring arylsulfatase A activity as described in example 1 of WO 2005/073367, and/or a polypeptide, which is capable of hydrolysing at least 40% of labelled arylsulfatase A substrate, fx. 14C palmitoyl sulfatide, loaded into MLD fibroblasts, when assayed by incubation at a dose level of 25 mU/ml in an assay as described in example 2 of WO 2005/073367.

The ASA may in another embodiment in particular comprise:
(a) the nucleic acid sequence of SEQ ID NO:1 in WO 2005/073367
(b) a portion of the sequence in (a), which encodes an amino acid sequence, which is enzymatically equivalent to recombinant human arylsulfatase A
(c) a nucleic acid sequence analogue having at least 75% sequence identity to any one of the sequences in (a) or (b) and at the same time encoding an amino acid sequence, which is enzymatically equivalent to recombinant human arylsulfatase A It may be preferred that the degree of sequence identity between the above mentioned nucleic acid sequence and SEQ ID NO: 1 of WO 2005/073367 is at least 80%, such as at least 85%, at least 90%, at least 95%, at least 97%, at least 98%, or at least 99%. It may be equally preferred that the degree of sequence identity between the amino acid sequence encoded by the above mentioned nucleic acid sequence and SEQ ID NO: 2 WO 2005/073367 is at least 80%, such as at least 85%, at least 90%, at least 95%, at least 97%, at least 98%, or at least 99%.

For the purpose of the present invention it is preferred that the arylsulfatase A is a recombinant enzyme, particularly preferred is recombinant human arylsulfatase A (rhASA).

It is preferred that rASA is produced in a mammalian cell or cell line and that said mammalian cell or cell line produces a glycoform of rASA, which is efficiently endocytosed in vivo via the mannose-6-phosphate receptor pathway. Specifically, the preferred glycoform of rASA comprises an amount of exposed mannose-6-phosphate, which allows efficient endocytosis of rASA in vivo via the mannose-6-phosphate pathway.

In a particular embodiment at least one of the produced glycoforms of rASA is similar to a glycoform produced in CHO cells.

The post translational modification of the cysteine residue in position 51 in the mature human arylsulfatase A is relevant for the activity of the enzyme. Accordingly, in a preferred embodiment of the present invention production of the arylsulfatase A or its equivalent occurs at a rate and under conditions, which result in a product comprising an isoform of the enzyme in which the amino acid corresponding to Cys-69 in SEQ ID NO: 2 of WO 2005/073367 is converted to Formylglycine, corresponding to Fgly-51 in SEQ ID NO: 3 of WO 2005/073367. SEQ ID NO: 4 of WO 2005/073367 represents mature human arylsulfatase A after cleavage of the 18 amino acid signal peptide but prior to modification of C-51.

Thus in another embodiment of the present invention the ASA or its enzymatical equivalent may be selected from the group consisting of
(a) the amino acid sequence of SEQ ID NO:3 of WO 2005/073367;
(b) a portion of the sequence in (a), which is enzymatically equivalent to recombinant human arylsulfatase A
(c) an amino acid sequence analogue having at least 75% sequence identity to any one of the sequences in (a) or (b) and at the same time being enzymatically equivalent to recombinant human arylsulfatase A.

It may be preferred that the degree of sequence identity between the enzyme produced according to the invention and SEQ ID NO: 3 of WO 2005/073367 or SEQ ID NO: 4 of WO 2005/073367 is at least 80%, such as at least 85%, at least 90%, at least 95%, at least 97%, at least 98%, or at least 99%.

For the biological activity and the effects of the enzyme in vivo requires to be optimal it is an advantage if an adequate amount of the enzyme has acquired a glycosylation pattern as described above and has been modified post translationally at position 51. Thus at least 50%, 60%, 70%, 80%, 90%, 95% or 98% of the ASA of the present invention may be in the above described glycoform/isoform.

The ASA of the present invention may in terms of its structure be different from the rASA according to SEQ ID NO: 3 of 2005/073367. It may be an advantage that the sequence of amino acid residues surrounding the Cys-51 is identical or has a high degree of sequence identity to the corresponding sequence in SEQ ID NO: 3. Thus, it may be preferred that a linear sequence of 20 amino acids, such as 19, 18, 17, 16, 15, 14, 13, 12, 11, 10, 9, 8, 7, 6, 5 or 4 amino acid residues surrounding the Cys-51 in the arylsulfatase A is identical or at least 90% identical, such as 95%, 96%, 97%, 98%, or 99% identical to the corresponding sequence in SEQ ID NO: 3 of 2005/073367. As the active form of rASA within the lysosymes is an octamer the ASA of the present invention may in particular be a rASA which is an octamer or assembles into an octamer under physiological conditions.

The enzyme activity of ASA, which is to be understood as the catalytic activity of the rASA, may be measured in an enzyme assay based on the rASA mediated hydrolysis of either a detectable substrate or a substrate, which leads to a detectable end product. In a preferred aspect the assay is based on hydrolysis of the synthetic, chromogenic substrate, para-Nitrocatechol sulphate (pNCS) which has an end product, para-Nitrocatechol (pNC) that absorbs light at 515 nm.

Lysosomal Alpha-Mannosidase

In yet another embodiment the polypeptide of interest may be a lysosomal alpha-mannosidase (LAMAN). Lysomal alpha-mannosidase belongs to EC 3.2.1.24 and is an exoglycosidase which hydrolyses the terminal, non-reducing alpha-D-mannose residues in alpha-D-mannosides from the non-reducing end during the ordered degradation of N-linked glycoproteins (Aronson and Kuranda FASEB J 3:2615-2622. 1989). In the context of the present invention the term lysosomal alpha-mannosidase may be used interchangeably with the short term LAMAN.

The LAMAN of the present invention may in particular be of human origin. The human enzyme is synthesised as a single polypeptide of 1011 amino acids with a putative signal peptide of 49 residues that is processed into three main glycopeptides of 15, 42, and 70 kD (Nilssen et al. Hum. Mol. Genet. 6, 717-726. 1997).

The gene coding for LAMAN (MANB) is located at chromosome 19 (19cen-q12), (Kaneda et al. Chromosoma 95:8-12. 1987). MANB consists of 24 exons, spanning 21.5 kb (Gen Bank accession numbers U60885-U60899; Riise et al. Genomics 42:200-207. 1997). The LAMAN transcript is >>3,500 nucleotides (nts) and contains an open reading frame encoding 1,011 amino acids (GenBank U60266.1).

The cloning and sequencing of the human cDNA encoding LAMAN has been published in three papers (Nilssen et al. Hum. Mol. Genet. 6, 717-726. 1997; Liao et al. J. Biol. Chem. 271, 28348-28358. 1996; Nebes et al. Biochem. Biophys. Res. Commun. 200, 239-245. 1994). Curiously, the three sequences are not identical. When compared to the sequence of Nilssen et al (accession # U60266.1) a TA to AT change at positions 1670 and 1671 resulting in a valine to aspartic acid substitution was found by Liao et al. and Nebes et al.

In a most preferred embodiment, the lysosomal alpha mannosidase comprises the amino acid sequence of SEQ ID NO.: 1 of WO 2005/094874.

For practical and economical reasons it is preferred that the LAMAN of the present invention is produced recombinant. By recombinant production it may also be possible to obtain a preparation of the enzyme wherein a large fraction contains mannose-6-phosphate. Recombinant production may be achieved after transfection of a cell using a nucleic acid sequence comprising the sequence of SEQ ID NO: 2 of WO 2005/094874.

The alpha-mannosidase is preferably made in a mammalian cell system as this will result in a glycosylation profile, which ensures efficient receptor mediated uptake in cells of for instance visceral organs of the body. In particular, it has been found that production of the enzyme in CHO, COS or BHK cells ensures adequate post-translational modification of the enzyme by addition of mannose-6-phosphate residues. In addition a correct sialylation profile is obtained. Correct sialylation is known to be important in order to prevent uptake by the liver, because of exposed galactose residues.

In even more preferred embodiments the mammalian cell system is therefore selected from the group comprising CHO, COS cells or BHK cells (Stein et al. J Biol Chem. 1989, 264, 1252-1259). It may further be preferred that the mammalian cell system is a human fibroblast cell line.

In a most preferred embodiment, the mammalian cell system is a CHO cell line.

In another embodiment the lysosomal alpha-mannosidase may be a preparation of lysosomal alpha-mannosidase wherein a fraction of said preparation consists of lysosomal alpha mannosidase having one or more N-linked oligosaccharides carrying mannose 6-phosphate groups.

It is further preferred that a fraction of a preparation of said lysosomal alpha-mannosidase is capable of binding to mannose 6-phosphate receptors.

The ability of the enzyme to bind to mannose-6-phosphate receptors may be determined in an in vitro assay as described in example 1 of WO 2005/094874. Here, binding of the enzyme to a MPR affinity 300 Matrix provides a measure of its ability to bind to mannose-6-phosphate receptors. In a preferred embodiment of the invention binding of the enzyme to mannose-6-phosphate receptors occurs in vitro.

In more preferred embodiments of the invention this fraction corresponds to from 1 to 75% of the activity of a preparation of lysosomal alpha-mannosidase, such as from 2 to 70%, such as from 5 to 60%, such as from 10 to 50% such as from 15 to 45%, such as from 20 to 40%, such as from 30 to 35%.

Accordingly, it is preferred that the lysosomal alpha-mannosidase has a content of mannose 6-phosphate residues allowing mannose 6-phosphate dependent binding of from 2 to 100%, 5 to 95%, 10 to 90%, 20 to 80%, 30 to 70% or 40 to 60% of the amount of enzyme to a Man-6-P-receptor matrix. At present, the degree of phosphorylation has been analysed in several batches of enzyme and, typically, from 30 to 45% of the enzyme is phosphorylated and binds the affinity matrix.

It is further preferred that a fraction constituting from 2-100%, 5-90%, 10-80%, 20-75%, 30-70%, 35-65% or 40-60% of the amount of said lysosomal alpha-mannosidase binds to the Man-6-P-receptor with high affinity. Theoretically, two mannose 6-phosphate groups must be positioned close to each other in order for the enzyme to bind a Man-6-P-receptor with high affinity. Recent observations suggest that the distance between the phosphorylated mannose residues must be 40 Å or less in order to obtain high affinity binding. In the human lysosomal alpha-mannosidase according to SEQ ID NO: 1 of WO 2005/094874 the two mannose 6-phosphate residues may be situated at the asparagines residues in positions 367 and 766. Accordingly, it is preferred that the medicament according to the present invention comprises lysosomal alpha-mannosidase, a fraction of which carries mannose 6-phosphate groups at both of these asparagine residues.

Preferably, the alpha-mannosidase is made by recombinant techniques. In a further embodiment, the alpha-mannosidase is of human origin (hLAMAN) and still more preferred a mature human alpha-mannosidase (mhLAMAN) or a fragment thereof. The fragment may be modified, however the active sites of the enzyme should be preserved.

It is to be expected that, in preparations of alpha-mannosidase according to the present invention, one fraction of the enzyme is represented by its precursor form, while other fractions represent the proteolytically processed forms of approximately 55 and 70 kDa.

Galactocerebrosidase

In another embodiment the polypeptide of interest may be a galactocerebrosidase, which may be shortended to GALC. Galactocerebrosidase belongs to E.C. 3.1.6.46 and are enzymes capable of catalysing the reaction of D-galactosyl-N-acylsphingosine+H2O=D-galactose+N-acylsphingosine, thus GALC catalyzes the degradation of galactolipids in for example myelin.

The GALC enzyme derived from humans is a glycosylated lysosomal enzyme comprising 643 amino acids and with a molecular weight of 72.8 kDa. The GALC of the present invention may in particular be of human origin. In a further embodiment the GALC may be expressed recombinant in one of the previously mentioned host cells. The host cell for recombinant expression of GALC may in particular be a CHO cell.

In the description and in the claims reference is made to the following amino acid and nucleic acid sequences:

| Sequence description | Sequence identifier |
|---|---|
| PBGD coding sequence 1 | SEQ ID NO.: 1 |
| PBGD coding sequence 2 | SEQ ID NO.: 2 |
| PBGD coding sequence 3 | SEQ ID NO.: 3 |
| PBGD coding sequence 4 | SEQ ID NO.: 4 |
| PBGD coding sequence 5 | SEQ ID NO.: 5 |
| PBGD coding sequence 6 | SEQ ID NO.: 6 |
| PBGD coding sequence 7 | SEQ ID NO.: 7 |
| PBGD coding sequence 8 | SEQ ID NO.: 8 |
| PBGD coding sequence 9 | SEQ ID NO.: 9 |
| PBGD coding sequence 10 | SEQ ID NO.: 10 |
| PBGD coding sequence, GenBank Acc. No. X04217 | SEQ ID NO.: 11 |
| PBGD coding sequence, GenBank Acc. No. X04808 | SEQ ID NO.: 12 |
| PBGD coding sequence, GenBank Acc. No. M95623 | SEQ ID NO.: 13 |
| PBGD aa sequence from coding sequence, GenBank Acc. No. M95623, Constitutive form | SEQ ID NO.: 14 |
| PBGD aa sequence from coding sequence, GenBank Acc. No. M95623, Erythropoietic form | SEQ ID NO.: 15 |
| ASA coding sequence Genbank Acc. No. J04593 | SEQ ID NO.: 16 |
| ASA coding sequence SEQ ID NO.: 1 of WO 2005/073367 | SEQ ID NO.: 17 |
| ASA aa sequence SEQ ID NO.: 2 of WO 2005/073367 | SEQ ID NO.: 18 |
| ASA aa sequence SEQ ID NO.: 3 of WO 2005/073367 | SEQ ID NO.: 19 |
| ASA aa sequence SEQ ID NO.: 4 of WO 2005/073367 | SEQ ID NO.: 20 |
| LAMAN aa sequence SEQ ID NO.: 1 of WO 2005/094874 | SEQ ID NO.: 21 |
| LAMAN coding sequence SEQ ID NO.: 1 of WO 2005/094874 | SEQ ID NO.: 22 |
| Galactocerebrosidase coding sequence | SEQ ID NO.: 23 |
| Galactocerebrosidase aa sequence | SEQ ID NO.: 24 |

With reference to these sequences the polypeptide of interest, according to preferred embodiments of the invention, comprises an amino acid selected from the group consisting of:
  i) an amino acid sequence as defined by any of SEQ ID NO.s: 14, 15, 18, 19, 20, 21 and 24;
  ii) a functionally equivalent part of an amino acid sequence as defined in i); and
  iii) a functionally equivalent analogue of an amino acid sequence as defined in i) or ii), the amino acid sequence of said analogue being at least 75% identical to an amino acid sequence as defined in i) or ii).

In particular embodiments the analogue in iii) is at least 80% identical to a sequence as defined in i) or ii), such as at least 85%, at least 90%, at least 95%, at least 98%, at least 99%, or such as at least 99.5% identical to a sequence as defined in i) or ii).

Further, the polypeptide of interest may be obtained by recombinant expression using a nucleic acid sequence comprising a sequence selected from the group consisting of:
  i) a nucleic acid sequence as defined by any of SEQ ID NO.s: 1-13, 16, 17, 22 and 23;
  ii) a nucleic acid sequence which is at least 75% identical to a nucleic acid sequence as defined in i).

For recombinant production of the polypeptide it may further be preferred that the acid sequence in ii) is at least 80% identical to a sequence as defined in i), such as at least 85%, at least 90%, at least 95%, at least 98%, at least 99%, or such as at least 99.5% identical to a sequence as defined in i).

Composition Comprising a Polypeptide of Interest

The following description of a composition comprising a polypeptide of interest relates both to a composition comprising a polypeptide which is concentrated according to a method of the present invention and it also relates to a composition of the present invention comprising at least 10 mg/ml polypeptide of interest.

The present invention also relates to a composition comprising at least 10 mg/ml polypeptide of interest, wherein the polypeptide of interest may be any polypeptide according to the present invention, such as in particular rhPBGD, aryl sulfatase, alpha-mannosidase or galactocerebrosidase. Said composition may in particular comprise at least 25 mg/ml polypeptide of interest, such as at least 50 mg/ml or at least 75 mg/ml or at least 100 mg/ml polypeptide of interest. Thus said composition may in particular comprise between 10-1000 mg/ml polypeptide of interest, such as between 10-500 mg/ml or between 10-300 mg/ml or between 10-200 mg/ml or between 25-500 mg/ml or between 25-400 mg/ml or between 40-400 mg/ml or between 40-300 mg/ml or between 50-400 mg/ml or between 50-300 mg/ml or between 75-400 mg/ml or between 75-300 mg/ml or between 100-200 mg/ml or between 100-150 mg/ml polypeptide of interest.

The composition comprising a polypeptide of interest may in particular be an aqueous solution.

Besides comprising a high concentration of polypeptide of interest said composition may in particular further comprise no aggregates of the polypeptide of interest or at least only very few aggregates. Hence the amount of polypeptide of interest present as aggregates may in particular constitute less than 5 w/w % of the total amount of polypeptide of interest in the composition. In particular said aggregates may constitute less than 4 w/w %, such as less than 3 w/w %, or less than 2 w/w %, or less than 1 w/w %, or less than 0.5 w/w %, or less than 0.1 w/w % of the total amount of polypeptide of interest. In the present context the term "aggregates" means any form of the polypeptide of interest which is not monomeric. Thus the term encompasses any dimer or multimer of the polypeptide of interest.

Furthermore, it is an advantage if said composition comprises only the polypeptide of interest or at least only minor traces of other proteins, i.e. proteins different from polypeptide of interest. Hence in a particular embodiment said composition comprises less than 1 w/w %, such as less than 0.5 w/w %, or less than 0.1 w/w %, or less than 0.05 w/w %, or less than 0.01 w/w % other proteins than the polypeptide of interest.

A range of factors affect the stability and activity of polypeptides and the composition comprising a polypeptide of interest may therefore in particular be optimized to keep the polypeptide of interest as stable as possible.

The pH generally affects the stability of a polypeptide of interest, thus the pH of a composition comprising a polypeptide of interest may in particular be in the range of 7.5-8.5, such as in particular between pH 7.7-8.2, more particularly between pH 7.8-8.0 or between pH 7.85-7.95, such as pH 7.8 or pH 7.9. This may in particular be the case if the polypeptide of interest is PBGD.

Thus the composition comprising a polypeptide of interest may in particular comprise a buffer capable of keeping the composition within the described pH range. Examples of such buffers include but are not limited to TRIS-HCL, Na-Citrate and $Na_2HPO_4$. The concentration of such a buffer may depend on the choice of the particular buffer and the presence of other components in the composition. If the buffer is $Na_2HPO_4$ the concentration of $Na_2HPO_4$ may be in the range of 0.5-15 mM, such as in the range of 1-10 mM, or in the range of 1.5-7.5 mM, such as in the range of 1.83-7.4 mM, or in the range of 1.5-3 mM, such as in the range of 1.83-3.7 mM, or in the range of 1.83-2.45 mM, or in the range of 3.5-7.5 mM, such as in the range of 3.6-7.4 mM, or in the range of 5.4-7.4 mM, such as 1.84 mM, or 2.45 mM, or 3.67 mM or 5.51 mM or 7.34 mM.

If the buffer is TRIS-HCL the concentration of TRIS-HCL may in particular be in the range of 2-50 mM, such as 2-40 mM, or 2-30 mM, or 2-20 mM, or 2-10 mM, or 5-25 mM, or 5-20 mM, or 8-12 mM, or 9-11 mM, e.g. 10 mM.

Examples of other compounds which the composition comprising a polypeptide of interest may comprise include but are not limited to amino acids, sugars, alcohols and detergents. Examples of such suitable compounds include but are not limited to glycine, mannitol, sucrose, L-serine, Tween 80 or a combination of one or more of said compounds. The concentration of these compounds depend on the particular compound, but for glycine the concentration may in particular be in the range of 1-200 mM, such as in the range of 5-190 mM, or in the range of 10-180 mM, or in the range of 10-170 mM, or in the range of 20-160 mM, or in the range of 20-150 mM, or in the range of 25-125 mM, or in the range of 5-100 mM, or in the range of 5-90 mM, or in the range of 5-80 mM, or in the range of 5-70 mM, or in the range of 5-60 mM, or in the range of 10-100 mM, or in the range of 10-90 mM, or in the range of 10-80 mM, or in the range of 10-70 mM, or in the range of 10-60 mM, or in the range of 12-60 mM, or in the range of 12-55 mM, or in the range of 13.5-54 mM, or in the range of 10-30 mM, such as in the range of 13.5-27 mM, or in the range of 13.5-18 mM, or in the range of 25-55 mM, such as in the range of 27-54 mM, or in the range of 40-55, such as in the range of 40.5-54 mM, such as 12.5, 13, 13.5, 14, 14.5, 17, 17.5, 18, 18.5, 19, 25, 26, 27, 28, 29, 30, 39.5, 40, 40.5, 41, 41.5, or 53, 53.5, 53, 54.5 or 55 mM.

The concentration of mannitol may in particular be in the range of 50-1000 mM, such as in the range of 50-900 mM, or in the range of 50-800 mM, or in the range of 50-700 mM, or in the range of 50-600 mM, or in the range of 100-900 mM, or in the range of 100-800 mM, or in the range of 100-700 mM, or in the range of 100-600 mM, or in the range of 100-500 mM, or in the range of 120-525 mM, or in the range of 125-500 mM, or in the range of 100-300 mM, such as in the range of 120-275 mM, or in the range of 120-170 mM, or in the range of 200-600 mM, such as in the range of 225-550 mM, or in the range of 240-510 mM, or in the range of 370-525 mM, such as 120, 125, 130, 160, 165, 166.7, 170, 175, 200, 221, 225, 250, 275, 300, 365, 370, 375, 380, 385, 490, 495, 500, 505 or 510 mM.

The concentration of sucrose may in particular be in the range of 1-200 mM, such as in the range of 5-190 mM, or in the range of 10-180 mM, or in the range of 10-170 mM, or in the range of 20-160 mM, or in the range of 20-150 mM, or in the range of 25-125 mM, or in the range of 5-100 mM, or in the range of 5-90 mM, or in the range of 5-80 mM, or in the range of 5-70 mM, or in the range of 5-60 mM, or in the range of 10-100 mM, or in the range of 10-90 mM, or in the range of 10-80 mM, or in the range of 10-70 mM, or in the range of 10-60 mM, or in the range of 12-60 mM, or in the range of 12-55 mM, or in the range of 13.5-54 mM, or in the range of 10-30 mM, such as in the range of 13.5-27 mM, or in the range of 13.5-18 mM, or in the range of 25-55 mM, such as in the range of 27-54 mM, or in the range of 40-55, such as in the range of 40.5-54 mM, such as 12.5, 13, 13.5, 14, 14.5, 17, 17.5, 18, 18.5, 19, 25, 26, 27, 28, 29, 30, 39.5, 40, 40.5, 41, 41.5, or 53, 53.5, 53, 54.5 or 55 mM. If sucrose is included in a composition which also comprises mannitol the concentration of mannitol may in particular be lowered corresponding to the concentration of sucrose; i.e. the concentration of mannitol and sucrose together may in particular be the same as the concentration of mannitol if this was to be used alone.

The concentration of Tween 80 may in particular be in the range of 0.001-1 w/v %, such as in the range of 0.005-1 w/v %, or in the range of 0.01-1 w/v %, or in the range of 0.001-0.5 w/v %, or in the range of 0.005-0.5 w/v %, or in the range of 0.01-0.5 w/v %, or in the range of 0.05-0.4 w/v %, or in the range of 0.05-0.3 w/v %, or in the range of 0.05-0.2 w/v %, or in the range of 0.075-0.4 w/v %, or in the range of 0.075-0.3 w/v %, or in the range of 0.075-0.2 w/v %, or in the range of 0.09-0.2 w/v %, such as 0.075, 0.08, 0.09, 0.1, 0.125, 0.15, 0.175 or 0.2 w/v %.

The composition comprising a polypeptide of interest, wherein the polypeptide in particular may be a PBGD, an aryl sulfatase, a lysosomal alpha-mannosidase or a galactocerebrosidase, may in particular comprise a combination of one or more of the above-mentioned compounds. A suitable example of such a composition may be one which besides the polypeptide of interest comprises $Na_2HPO_4$, glycine and mannitol. The pH of the composition and the concentration of the different compounds may be as described above. Hence said composition may in one embodiment comprise 0.5-15 mM $Na_2HPO_4$, 1-200 mM glycine, 50-1000 mM mannitol and a pH in the range of 7.5-8.5. Any combination of the above mentioned concentrations of compounds and pH are encompassed by the present invention. A specific example of a suitable combination of other compounds and pH in the composition comprising a polypeptide of interest is one which comprises 3.67 mM $Na_2HPO_4$, 27 mM glycine, 250 mM mannitol and has a pH in the range of 7.7 to 7.9.

Other examples of suitable compositions include, but are not limited to any of the following 1.84 mM $Na_2HPO_4$, 13.5 mM glycine, 125 mM mannitol and pH in the range of 7.7 to 7.9.

2.45 mM $Na_2HPO_4$, 18 mM glycine, 167 mM mannitol and pH in the range of 7.7 to 7.9.

5.51 mM $Na_2HPO_4$, 40.5 mM glycine, 375 mM mannitol and pH in the range of 7.7 to 7.9.

7.34 mM $Na_2HPO_4$, 54 mM glycine, 500 mM mannitol and pH in the range of 7.7 to 7.9.

3.67 mM $Na_2HPO_4$, 27 mM glycine, 220 mM mannitol, 30 mM sucrose and pH in the range of 7.7 to 7.9.

3.67 mM $Na_2HPO_4$, 245 mM mannitol, 32 mM sucrose and pH in the range of 7.7 to 7.9.

3.67 mM $Na_2HPO_4$, 27 mM L-serine, 250 mM mannitol and pH in the range of 7.7 to 7.9.

10 mM TRIS-HCl, 27 mM glycine, 250 mM mannitol and pH in the range of 7.7 to 7.9.

3.67 mM NaCitrat, 27 mM glycine, 250 mM mannitol and pH in the range of 7.7 to 7.9.

3.67 mM $Na_2HPO_4$, 27 mM glycine, 220 mM mannitol, 29 mM sucrose, 0.1% (w/v) Tween 80 and pH in the range of 7.7 to 7.9.

3.67 mM $Na_2HPO_4$, 27 mM glycine, 220 mM mannitol, 29 mM sucrose, 0.1% (w/v) Tween 80 and pH in the range of 7.7 to 7.9.

The composition comprising a polypeptide of interest may in particular be used for therapeutic applications in mammals. Thus the composition comprising a polypeptide of interest may in particular be isotonic with regard to the tissue of mammals, e.g. it may in particular have an osmolality in the range of 200-400 mOsm/kg, such as in the range of 250-350 mOsm/kg or in the range of 275-325 mOsm/kg or in the range of 295-305 mOsm/kg, such as 295 mOsm/kg or 300 mOsm/kg or 305 mOsm/kg.

Method of Concentrating a Polypeptide of Interest

The method of the present invention comprises the steps of a) centrifugation and/or filtration of a composition comprising a polypeptide of interest and b) concentrating the composition from step a). The inventors of the present invention have found that by centrifugation and/or filtrating a composition comprising a polypeptide of interest prior to concentrating said composition it is possible to obtain a composition comprising a highly concentrated polypeptide of interest without any or with at least only few aggregates of the polypeptide of interest. Furthermore, it is generally an advantage for therapeutic applications of a polypeptide that the amount of polypeptide aggregates is reduced, e.g. as they may increase the risk of eliciting an immune response towards the polypeptide.

For administration of a polypeptide subcutaneously it is an advantage that the polypeptide composition has a high activity in a small volume as only small volumes can be injected subcutaneously.

Proteins or polypeptides may in general form aggregates when they are concentrated. Thus it is an advantage that when the method of the present invention is used to concentrate a polypeptide of interest it does not cause a high rate of polypeptide aggregate formation. As shown in the examples the amount of PBGD aggregates in the composition obtained by the concentration method of the present invention is similar to that of a non-concentrated PBGD composition.

In a particular embodiment step a) of the method is performed prior to step b).

Step a) Centrifugation and/or Filtration

The inventors of the present invention have found that prior to concentrating a composition comprising a polypeptide of interest it is an advantage to pre-treat the composition by centrifugation and/or filtration of the composition as by this pre-treatment many or most of the polypeptide aggregates are removed.

When the concentration of the composition in step b) is performed by a method which relies on the use of a filter or membrane, such as ultrafiltration, the presence of aggregates may block the filter or membrane so that small molecules and liquid are not able to cross the filter or membrane. This may decrease the speed by which the composition is concentrated and/or completely block any further concentration.

Hence for this type of concentration the pre-treatment according to step a) is an advantage as removal of the aggregates makes it possible to obtain compositions of a polypeptide of interest which are more concentrated than if said composition were not been pre-treated.

When the concentration of the composition in step b) is performed by a method which is based on the removal of water, such as freeze-drying or evaporation, the pre-treatment in step a) has the advantage that it reduces the amount of aggregates present in the concentrated composition.

Step a) may be performed by one of the following three alternatives:

Centrifugation,

Filtration, or

Centrifugation and filtration.

If step a) comprises both centrifugation and filtration it is an advantage to perform the centrifugation prior to the filtration as the inventors of the present invention have found that the centrifugation removes most of large aggregates and the filtration subsequently removes the remaining smaller aggregates.

Centrifugation

To be able to remove the aggregates the composition comprising a polypeptide of interest may be centrifuged at a force in the range of 1500-3000 g, such as in the range of 1800-2500 g, or in the range of 2000-2300 g.

Typically the composition may be centrifuged for 10-60 minutes, such as for 15-50 minutes or for 20-40 minutes.

As the temperature may affect the stability of the polypeptide of interest the centrifugation may be performed at a temperature in the range of 2-20° C., such as from 3-15° C. or in the range of 3-10° C., or in the range of 3-8° C., such as at 4° C. or 5° C. or 6° C.

The centrifugation results in that the polypeptide of interest aggregates sediment, i.e. they form a pellet, while the individual polypeptide of interest molecules stays in the solution. So it is the supernatant of the centrifuged composition which is subsequently used in the method of the present invention.

Filtration

The composition comprising a polypeptide of interest may be filtered through a filter having a pore-size in the range of 0.20-5 µm, such as in the range of 0.2-2.5 µm.

Besides the pore-size of the filter also the material of which the filter is made of may affect filtration of polypeptide of interest. Examples of suitable membrane filters include but are not limited to polyethersulfone (PES), cellulose acetate, regenerated cellulose and polyvinylidene flouride (PVDF).

When molecules such as proteins are filtered it is usually the small molecules which are removed thus after filtration the polypeptide of interest may generally be present in the retentate. Hence it is generally the retentate from the filtration which is used in the subsequent steps of the present invention.

Step b) Concentrating

In principle any method of concentrating the polypeptide of interest composition may be used in step b) of the present invention.

Examples of such suitable methods include but are not limited to ultrafiltration and concentration by removal of water.

Ultrafiltration

Ultrafiltration is a separation method in which hydraulic pressure is used to force molecules and solvent across a membrane comprising pores of a particular size, also known as the cut-off size of value. Only molecules which have a molecular weight smaller than the cut-off value of the membrane are able to cross the membrane while those with a larger molecular weight do not cross the membrane and form the so called retentate. The molecules present in the retentate are thereby concentrated as the solvent flows across the membrane.

In a particular embodiment the concentration of the solution or composition comprising a polypeptide of interest may be performed by Tangential flow filtration (TFF). This method is in particular useful for large-scale concentration, i.e. for concentration of solutions with a volume from one liter to several hundreds of liters. Thus this method is in particular useful for production of concentrated solutions of a polypeptide of interests on an industrial scale.

The TFF technique is based on the use of a particular apparatus which causes the solution which is to be filtrated to flow across a semi-permeable membrane; only molecules which are smaller than the membrane pores will pass through the membrane, forming the filtrate, leaving larger matter to be collected (retentate). With the TFF method two different pressures are applied; one to pump the solution into the system and to circulate it in the system (inlet pressure), and another pressure is applied over the membrane (membrane pressure) to force the small molecules and the solvent across the membrane. The inlet pressure may typically be in the range of 1-3 bar, such as between 1.5-2 bar. The membrane pressure may typically be larger than 1 bar.

The concentrated composition of a polypeptide of interest may be collected as the retentate when TFF is used to concentrate the composition.

Membranes useful for TFF may typically be made of regenerated cellulose or polyethersolufone (PES).

The pore-size of the membrane may typically have a molecular weight cut-off which is smaller than 10.000 Mw, such as in the range of 10-10.000 Mw.

In another embodiment the concentration of the composition comprising a polypeptide of interest may be performed by the use of a centrifugal device. The principle of this method is that the solution is filtrated over a membrane by the application of a centrifugal force over the membrane. Such membranes are often characterized by a molecular weight (Mw) cut-off, i.e. this is the maximum molecular size of compounds which are able to cross the membrane and compound with a molecular size larger than this will not cross the membrane. The Mw cut-off of the membranes used in the present invention may in particular be smaller than 30.000 Mw, such as between 10-30.000 Mw.

The membrane may in particular be made of polyethersulfone (PES) or regenerated cellulose.

Examples of such suitable commercial filter devices may be Centricon Plus-80 or Centricon Plus-15.

The concentration may typically be performed by centrifugation at 2000-4500 g, such as between 2500-4000 g, or between 2750-3500 g, or between 3000-3500 g, such as at 3000 g or 3100 g or 3200 g or 3300 g or 3400 g or 3500 g.

Typically the centrifugation may be run for several hours, e.g. for more than one hour, such as for 1-10 hours.

To minimize any negative effects on the stability of the polypeptide of interest the centrifugation may in particular be performed at a temperature in the range of 2-20° C., such as in the range of 3-15° C. or in the range of 3-10° C. or in the range of 3-6° C.

Concentrating by Removal of Water

The principle of concentration by removal of water is usually that all, or most, of the water is removed to obtain a solid, and then subsequently diluting or dissolving this solid in a volume of water which is less than what it was previously diluted or dissolved in. However, it may in principle be performed by just removing the necessary amount of water to obtain the desired concentration without subsequently re-diluting or re-dissolving the compound.

Examples of suitable methods of concentrating by removal of water include freeze-drying and evaporation.

Both for freeze-drying and evaporation the three most relevant parameters is the temperature, pressure and the time.

The method of freeze-drying may be comprise the following three or four steps; a freezing-phase, a primary drying phase and a secondary drying phase and optionally a step of annealing after the freezing phase. Freeze-drying may in particular be performed as described with regard to freeze-drying included as a further step of the method of the present invention.

Further Steps

The polypeptide of interest may derive from a natural source, i.e. from cells naturally expressing the polypeptide of interest, or it may in particular be expressed recombinant.

Independent of where the polypeptide of interest derives from it may have been purified before being subjected to a method of the present invention.

Such "purification" may in particular include but is not limited to removal of cell debris, removal of other proteins than polypeptide of interest and removal of other components which may be present in the source from which the polypeptide of interest is derived. Thus in a particular embodiment of the present invention the composition comprising a polypeptide of interest comprises less than 5 w/w %, or less than 1 w/w % or less 0.5 w/w % or less than 0.1 w/w % or less than 0.05 w/w % or less than 0.01 w/w % other proteins than the polypeptide of interest.

Thus other proteins which are expressed by e.g. a host cell may be removed from the composition comprising a polypeptide of interest before it is used in a method of the present invention.

Thus in a particular embodiment the method of the present invention may comprise one or more of following steps prior to step a):

i) recombinant expression of a polypeptide of interest
ii) purification of polypeptide of interest composition by one or more steps of chromatography
iii) exchange of the formulation buffer Recombinant expression of a polypeptide of interest may in particular be performed as described previously with regard to the polypeptide of interest.

If the polypeptide of interest is PBGD examples of suitable types of chromatography include but are not limited to affinity chromatography, Ion Exchange Chromatography (IEC) and chromatography on a hydroxyapatite column. In principle any combination of these chromatography methods may be used. The inventors of the present invention have previously found for PBGD that it is an advantage to perform at least the step of affinity chromatography and if this is combined with any of the other methods of chromatography it is an advantage to perform the step of affinity chromatography prior to the other chromatography steps (see e.g. WO 03/002731).

For the embodiment where the polypeptide of interest is PBGD examples of commercially available affinity chromatography columns include affinity coupling, group specific affinity, and metal chelate affinity columns.

The product catalogue 2001 of the company Amersham Pharmacia Biotech gives examples of affinity coupling columns such as columns comprising immobilising ligands containing —$NH_2$ and columns comprising ligands containing primary amino groups.

Metal chelate affinity columns are specially preferred for purifying proteins via metal ion complex formation with exposed histidine groups. Example 3 of WO01/07065 describes construction of a recombinant human Porphobilinogen deaminase with a "His-Tag" (rhPBGD-His). In order to purify rhPBGD-His it is preferred to use a metal chelate affinity column, such as a column having a cobalt metal affinity resin.

Examples of other suitable methods of affinity chromatography include but are not limited to columns having porcine heparin as ligand or columns having 1-Amino-4-[[4-[[4-chloro-6-[[3 (or 4)-sulfophenyl]amino]-1,3,5-triazin-2-yl]amino]-3-sulfophenyl]amino]-9,10-dihydro-9,10-dioxo-2-anthracenesulfonic acid, also known as Cibracon Blue 3G, as ligand and using Triazine coupling as the ligand coupling method. A commercially available example of the latter is Blue Sepharose 6 Fast Flow (FF) from Amersham Pharmacia Biotech. Accordingly, a preferred embodiment of the invention relates to the process, as described herein, wherein the affinity chromatography column of step (i) is a column using a triazine coupling as ligand coupling method, and more preferably wherein the ligand is Cibacron Blue 3G.

The term "Ion Exchange Chromatography (IEC)" should herein be understood according to the art as a column separating molecules such as proteins on the basis of their net charge at a certain pH by electrostatic binding to a charged group on the column. Ion exchange denotes the absorption of ions of one type onto a column in exchange for others which are lost into solution.

Examples of suitable IEC columns are columns such as a Q Sepharose column, a Q SP Sepharose column, or a CM Sepharose column, it may in particular be a DEAE Sepharose column.

An example of a suitable hydroxyapatite column is a ceramic hydroxyapatite column. Hydroxyapatite ($Ca_5(PO_4)3OH)_2$ is a form of calcium phosphate that can be used for the separation and purification of proteins, enzymes, nucleic acids, viruses, and other macromolecules. Ceramic hydroxyapatite is a spherical, macroporous form of hydroxyapatite. CHT Type I (Bio-Rad) is an example of a suitable commercially available ceramic hydroxyapatite chromatography column.

In one embodiment the method of the present invention may comprise the following steps prior to step a):
  i) recombinant expression of PBGD
  ii) subjecting the PBGD composition from step i) to affinity chromatography
  iii) subjecting the PBGD composition of step ii) to ion exchange chromatography In a further embodiment the method of the present invention may comprise the following steps prior to step a):
  i) recombinant expression of PBGD
  ii) subjecting the PBGD composition from step i) to affinity chromatography
  iii) subjecting the PBGD composition from step ii) to ion exchange chromatography
  iv) subjecting the PBGD composition from step iii) to a hydroxyapatite column Both of these methods may optionally include a further step of dilution of diafiltration of the PBGD composition obtained from step ii). Thus said step should be after step ii) and before iii), i.e. a step iia). Step iia) has the purpose of reducing the concentration of salts to suitable conductivity, e.g. <10 mS/cm. This may in particular be relevant if DEAE Sepharose is used as resin in the ion exchange chromatography step, i.e. step iii), as this may facilitate binding of the captured PBGD to the DEAE Sepharose resin. Dilution may be obtained by addition of purified water directly or by ultrafiltration against purified water.

The recombinant expression of PBGD, step i) may be performed by any of the methods described above.

Examples of suitable affinity chromatography columns in step ii) may be any of the above mentioned.

Examples of suitable methods of performing ion exchange chromatography in step iii) may be any of the above mentioned.

Examples of suitable hydroxyapatite chromatography columns in step iv) may be any of the above mentioned.

In a particular embodiment the affinity chromatography column may be a column using a triazine coupling as ligand coupling method, and in particular such a method wherein the ligand is Cibacon Blue 3G. This may in particular be a Blue Sepharose 6 Fast Flow column, and the ion exchange chromatography column may be DEAE Sepharose column, and in the embodiment wherein the method also comprises a step iv) this column may in particular be a ceramic hydroxyapatite column.

The method of the present invention may also comprise further steps after step b) of the method. Such steps include but are not limited to one or more of the following:
  freeze-drying the composition comprising a concentrated polypeptide of interest,
  changing the buffer of the composition comprising a concentrated polypeptide of interest,
  sterile filtration of the composition comprising a concentrated polypeptide of interest
  evaporation Different freeze-driers, volume of solutions to be freeze-dried and other parameters may be used in the method of the present invention. An example of a suitable freeze-dryer includes but is not limited to a Lyostar (FTM-systems) freeze-drier as used the examples of the present invention, where the solutions comprising a concentrated polypeptide of interest, i.e. in this case PBGD, were filled in 2 and 6 ml injection glass vials (type 1) and stoppered with rubber stoppers (chlorobutyl). The freeze-drying may be performed by the following three steps;
  i) freezing,
  ii) primary drying, and
  iii) secondary drying.

Step i) freezing may in particular be performed by first loading a sample in ambient temperature and cooling it to 0° C. and keeping it at 0° C. for 30 minutes, before lowering the temperature by 1° C. per minute to −40° C. and keeping it at −40° C. for 30 minutes.

Step ii) primary drying may in particular be performed by drawing the vacuum pressure 126 mTorr, raising the temperature by 1° C. per minute to 0° C. and keeping the sample at 0° C. for 360 minutes Step iii) secondary drying may in particular be performed by drawing the full vacuum simultaneously with raising the temperature by 0.5° C. per minute to +30° C. and keeping the sample at +30° C. for 360 minutes.

After the secondary drying the sample may further be closed under vacuum or closed after filling with nitrogen.

An example of a suitable freeze-drying method includes the one described in the examples of the present invention.

The freeze-drying may in further embodiment comprise an annealing step prior to the primary drying phase. The inventors of the present invention have found that inclusion of an annealing step in the freeze-drying method improves the visual appearance, as visualised by fewer cracks, and/or results in a shorter reconstitution time of the freeze-dried product compared to when the same method of freeze-drying is used but without the annealing step. It is an advantage that the time for reconstitution of a freeze-dried product is reduced, especially if it is to be used as a pharmaceutical which is administered as a solution. An improved visual appearance is usually also regarded as an advantage for most products.

Thus the freeze-drying may comprise the following steps:
  i) freezing
  ii) annealing
  iii) primary drying
  iv) secondary drying.

The freezing, primary drying and secondary drying steps may in particular be performed as described above. The annealing step, i.e. step ii) may in particular be performed by after 30 minutes of freezing, raising the temperature at e.g. a rate of 2° C. per minute to −10° C. or −20° C. and keeping this temperature for 120 or 420 minutes and then lowering the temperature e.g. a rate of 2° C. per minute to −40° C. at which temperature the sample may be kept at 60-90 minutes before start of the step of primary drying.

Changing the buffer of the composition comprising a concentrated polypeptide of interest may in particular be performed by a) diluting, e.g. 5-15 times, the composition comprising a concentrated polypeptide of interest in a buffer or formulation, b) concentrating the diluted composition again and performing the steps a) and b) a sufficient number of times so that amount of the excipients in the buffer or formulation present in the composition before these steps constitute less than e.g 5 v/v % or less than 1 v/v % of excipients in the buffer or formulation present in said composition after said steps were performed.

In particular the composition comprising a polypeptide of interest obtained from step b) of the present invention may in particular further comprise a step of sterile filtration of said composition and/or a step of freeze-drying the composition.

Sterile filtration is generally performed by filtration of the composition through a filter with a pore-size of 0.22 μm or 0.20 μm. Freeze-drying may in particular be performed as described above.

The present invention also relates to a freeze-dried composition obtained by a method of the present invention.

Subcutaneous Injection

The present invention also relates to the use of a composition comprising in the range of 50-300 mg/ml polypeptide of interest for the manufacture of a medicament for subcutaneous injection into a mammal.

The polypeptide of interest may be any polypeptide of interest according to the present invention, including but not limited to PBGD, aryl sulfatase A, lysosomal alpha-mannosidase and galactocerebrosidase.

The term subcutaneous is often shortened to s.c. and the two terms may be used interchangeably in the context of the present invention.

When injection is performed subcutaneously it is usually not possible to inject more than 1.5 mL due to physiologically restraints.

As the patient usually needs a certain amount of the particular polypeptide of interest there is a correlation between the volume of the composition comprising a polypeptide of interest which needs to be administered to the patient and of the concentration of polypeptide of interest in said composition.

It is therefore an advantage of the present invention that the composition comprising a polypeptide of interest comprises a high concentration of the polypeptide of interest and that this high concentration of the polypeptide of interest can be obtained without the formation of large amounts of polypeptide aggregates. The use of such concentrated polypeptide of interest compositions makes it possible to inject a smaller volume of said composition and at the same time ensure that the patient receives an adequate amount of the polypeptide of interest; thus making it easier to administer the polypeptide of interest subcutaneously.

The above-mentioned composition comprising a polypeptide of interest may in particular comprise between 75-250 mg/ml, such as between 75-200 mg/ml or between 75-150 mg/ml or between 100-150 mg/ml or between 100-125 mg/ml or between 125-150 mg/ml of polypeptide of interest.

As described above the volume of composition comprising a polypeptide of interest which it is necessary to inject into the patient to ensure that the patient receives an adequate amount of the polypeptide of interest correlates with the concentration of the polypeptide of interest in said composition.

Thus the volume of such a composition will generally be adjusted according to the concentration of the polypeptide of interest in the composition. However, the volume may generally be in the range of 0.1-1.5 ml, such as in the range of 0.1-1.5 ml or in the range of 0.5-1.5 ml or in the range of 0.5-1.5 ml or in the range of 0.75-1.5 ml or in the range of 0.75-1.5 ml or in the range of 1-1.5 ml or in the range of 1-1.5 ml.

The amount of polypeptide of interest which it is relevant to administer to a patient generally depends on the weight of the individual and the particular polypeptide of interest.

In one embodiment the present invention relates to a method of treating a mammal for Acute Intermittent *Porphyria* comprising subcutaneous injection of a composition of 50-300 mg/ml PBGD.

Administration of PBGD may in particular be useful for the treatment of Acute Intermittent *Porphyria*. However, it is contemplated that administration of PBGD also may be useful for the treatment of other *porphyrias*, such as *Hereditary coproporphyria* or *Variegata porphyria*. *Porphyria* is a term used to collectively describe a number of diseases caused by different deficiencies in the heme biosynthetic pathway. Hence it is contemplated that administration of PBGD, e.g. in combination with other therapeutics, to a patient suffering from any type of *porphyria* may help to increase the overall turnover of the different intermediates in the pathway. For example Meissner P N et al., 1986, European Journal of Clinical Investigation, vol. 16, 257-261; Hift R J et al., 1997, S. Afr. Med. J., vol. 87, 718-27 and Meissner P et al., 1993, J. Clin. Invest., vol. 91, 1436-44 describe accumulation of ALA and PBG in *Hereditary coporphyria* and *Variegata porphyria*. In theses diseases the accumulation of ALA and PBG results from enzymatic defects that are located four and five steps downstream form the conversion of ALA to PBG, respectively. In the two most recent papers it is described how the porphyrinogen which accumulates in patients with *Variegata porphyria* is capable of inhibiting PBG-deaminase.

In a further embodiment the present invention relates to a method of treating a mammal for metachromatic leukodystrophy comprising subcutaneous injection of a composition of 50-300 mg/ml aryl sulfatase A.

Metachromatic leukodystrophy (MLD) is caused by an autosomal recessive genetic defect in the lysosomal enzyme Arylsulfatase A (ASA), resulting in a progressive breakdown of membranes of the myelin sheath (demyelination) and accumulation of galactosyl sulphatide (cerebroside sulphate) in the white matter of both the central nervous system (CNS) and the peripheral nervous system. In histologic preparations, galactosyl sulphatide forms spherical granular masses that stain metachromatically. Galactosyl sulphatide also accumulates within the kidney, gallbladder, and certain other visceral organs and is excreted in excessive amounts in the urine.

Galactosyl sulfatide is normally metabolised by the hydrolysis of 3-O-sulphate linkage to form galactocerebroside through the combined action of the lysosomal enzyme arylsulfatase A (EC 3.1.6.8) (Austin et al. Biochem J. 1964, 93, 15C-17C) and a sphingolipid activator protein called saposin B. A profound deficiency of arylsulfatase A occurs in all tissues from patients with the late infantile, juvenile, and adult forms of MLD (see below). In the following, the arylsulfatase A protein will be termed "ASA". A profound deficiency of ASA occurs in all tissues from patients with MLD.

In yet another embodiment the present invention relates to a method of treating a mammal for the lysosomal storage disorder alpha-mannosidosis comprising subcutaneous injection of a composition of 50-300 mg/ml lysosomal alpha-mannosidase.

Alpha-mannosidosis is a recessive, autosomal disease that occurs world wide with a frequency of between 1/1,000,000 and 1/500,000. Mannosidosis is found in all ethnic groups in Europe, America, Africa and also Asia. It is detected in all countries with a good diagnostic service for lysosomal storage disorders, at a similar frequency. They are born apparently healthy; however the symptoms of the diseases are progressive. Alpha-mannosidosis displays clinical heterogeneity, ranging from very serious to very mild forms. Typical clinical symptoms are: mental retardation, skeletal changes, impaired immune system resulting in recurrent infections, hearing impairment and often the disease is associated with a typical facial characteristics such as a coarse face, a prominent forehead, a flattened nasal bridge, a small nose, and a broad mouth. In the most severe cases (mannosidosis type I) the children suffer from hepatosplenomegaly, and they die during the first years of life. Possibly this early death is caused by severe infections due to the immunodeficiency caused by the disease. In milder cases (mannosidosis type 2) the patients usually reach adult age. The skeletal weaknesses of the patients result in the needs of wheeling chairs at age 20 to 40. The disease causes a diffuse dysfunction of the brain often resulting in weak mental performances that excludes anything but the most basic skills of simple reading and writing. These problems associated with hearing inabilities and other clinical manifestations preclude the patient from an independent life, the consequence being that life long caretaking is needed.

In yet another embodiment the present invention relates to a method of treating a mammal for Krabbe disease comprising subcutaneous injection of a composition of 50-300 mg/ml galactosylcerebrosidase.

In humans a deficiency in the GALC enzyme results in an autosomal inherited genetic Lysosomal Storage disease known as Krabbe disease or Globoid Cell Leukodystrophy. The enzyme is generally expressed in the testis, kidneys, placenta, liver and brain of human beings and a deficiency in the GALC enzyme generally results in a disorder in the myelin metabolism and in the central and peripheral nervous systems (the CNS and PNS, respectively).

Krabbe disease has been observed in humans of any age, nationality and sex.

It should be noted that embodiments and features described in the context of one of the aspects of the present invention also apply to the other aspects of the invention. In particular, all of the embodiments described for the composition comprising a polypeptide of interest, such as the presence of further compounds, buffers and pH also apply to the composition comprising a polypeptide of interest used in the present applications.

When an object according to the present invention or one of its features or characteristics is referred to in singular this also refers to the object or its features or characteristics in plural. As an example, when referring to "a polypeptide" it is to be understood as referring to one or more polypeptides.

Throughout the present specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All patent and non-patent references cited in the present application, are hereby incorporated by reference in their entirety.

The invention will now be described in further details in the following non-limiting Experimental sections.

EXPERIMENTAL

Materials
rhPBGD

The rhPBGD used in the following experiments were obtained according to process 2 in example 1 of WO 03/002731, where process 2 is the process which includes step IV, i.e. the ceramic hydroxyapatite chromatography step.

Formulation Buffer

The recombinant and purified rhPBGD was present in the following aqueous formulation buffer:
3.67 mM $Na_2HPO_4$
27 mM Glycine
250 mM Mannitol
and a pH of 7.9

The formulation buffer was then sterile-filtered trough a 0.22 µm filter.

Methods
Freeze-Drying

The freeze-drying of the purified rhPBGD solutions were performed in a Lyostar (FTM-systems) freeze-drier according to the following schedule:

| Freezing phase | 0° C. | 30 min | 760 Torr |
|---|---|---|---|
| | 0° C. to −40° C. | 1° C./min | 760 Torr |
| | −40° C. | 30 min | 760 Torr |
| Primary drying | −40° C. to 0° C. | 1° C./min | 169 mTorr |
| | 0° C. | 240 min | 169 mTorr |
| Secondary drying | 0° C. to 30° C. | 10° C./60 min, 180 min | 20 mTorr |
| | 30° C. | 720 min | 20 mTorr |

Visual Observation (Clarity and Colour)

The liquid was visually studied with respect to colour, clarity and precipitates according to the scheme below.
Colour: 1: No colour; 2: Slightly yellow; 3: Yellow
Clarity: 1: Clear; 2: Slightly turbid; 3: Turbid Other remarks: Other observations from the operator were in some instances included here (e.g. precipitates, undissolved material etc)

pH-Measurement

The pH-meter (Metrohm 691 pH Meter) and electrode (combined LL pH electrode) were calibrated with 3 standard reference solutions (Merck) in the range 4.00 to 9.00. The liquid was finally analysed.

Protein Concentration

Protein concentration in extract, in-process samples, bulk drug substance and final product was determined by a method that utilizes principles of the reduction of $Cu^{2+}$ to $Cu^+$ by protein in an alkaline medium (the Biuret reaction). The $Cu^+$ ions were then reacted with a reagent containing bicinchoninic acid resulting in a highly sensitive and selective colorimetric detection.

Purity

Recombinant human Porphobilinogen Deaminase (rhPBGD) and rhPBGD variants were separated according to their ability to adsorb and desorb to silica based stationary media depending on the percentage of organic modifier (acetonitrile) in the mobile phase.

rhPBGD Activity

Porphobilinogen deaminase (PBGD) catalyzes the addition of 4 molecules of porphobilinogen (PBG) to form a linear tetramer, preuroporphyrinogen, which is released from the enzyme and in vivo circularized to uroporphyrinogen III by the action of Uroporphyrinogen III synthase. Preuroporphyrinogen can be chemically oxidized with benzoquinone to form uroporphyrin, which absorbs light at 405 nm.

The analyses were performed on one single vial on each test occasion. For the determination of rhPBGD activity and protein concentration the tests were performed in duplicate and triplicate respectively, for each vial.

Osmolality

One vial of freeze-dried rhPBGD was resuspended in 1.00 ml MilliQ-water. The vial of frozen aqueous solution of rhPBGD was thawed. The osmometer (Vapro osmometer) was calibrated with 3 standard solutions in the range 100-1000 mOsm/kg (100, 290, 1000 mOsm/kg). The liquid was then analyzed.

Example 1

Concentrating with Centrifugal Filter Devices

Frozen PBGD-bulk solution (7 mg/mL rhPBGD, 3.67 mM $Na_2HPO_4$, 27 mM glycine, 250 mM Mannitol, pH 7.9) was thawed in a water-bath at 20° C., centrifuged at 3200 g for 10 min and thereafter sterile-filtrated by 0.20 μm-PES filters (Nalgene Polyethersulfone filters). The PBGD-bulk solution was concentrated to 100 mg/ml by running the Centrifugal Filter Devices Centricon Plus-80 (Mw cut-off 30000) and Centricon Plus-15 (Mw cut-off 30000) at 3200 g for several hours. The concentrated solution, i.e. the retentate, was sterile-filtrated by 0.22 μm-filters (Millex GV) and finally a part of this solution was diluted with sterile formulation buffer to get 50 mg/ml. The 5 mg/ml-solution was prepared by directly diluting the recombinant and purified hPBGD with sterile formulation buffer.

The 5 mg/mL, 50 mg/mL and 100 mg/mL rhPBGD were then freeze-dried as described above. Several vials of each the above-mentioned freeze-dried rhPBGD solutions with 5, 50 and 100 mg/mL rhPBGD and of the aqueous 5 mg/mL rhPBGD solution were stored at 40° C.±2° C., 75%±5% relative humidity (RH). The vials were stored protected from light in a well sealed secondary package (paper box).

At the indicated time points (i.e. time of storage) a vial of each freeze-dried samples were resuspended in 1.00 mL Millipore water.

Each of the resuspended vials and the aqueous vial of rhPBGd were then visually observed with regard to colour, clarity and precipitates, and the pH, protein concentration, purity and rhPBGD activity were measured as described above.

The results are given in the following tables 1-4:

TABLE 1

Freeze-dried product, 5 mg/mL

| Time-point (month) | Activity (U/ml) | Concentration (mg/ML) | Specific activity (U/mg) | Purity (%) | Visual observation |
|---|---|---|---|---|---|
| 0 | 93.2 | 4.3 | 21.5 | 99.6 | Colour: 1, clarity: 1 |
| 0.5 | 81.0 | 5.2 | 15.6 | ND | Colour: 1, clarity: 1 |
| 1 | 76.6 | 5.9 | 13.1 | 99.9 | Colour: 1, clarity: 1 |
| 1.5 | 87.0 | 5.5 | 15.9 | 99.7 | Colour: 1, clarity: 1 |
| 2 | 53.3 | 4.7 | 11.4 | 99.6 | Colour: 1, clarity: 1 |
| 3 | 50.8 | 4.8 | 10.7 | 99.6 | Colour: 1, clarity: 1 |
| 6 | 34.3 | 5.3 | 6.5 | 99.6 | Colour: 1, clarity: 1 |

TABLE 2 freeze-dried product; 50 mg/ml

| Time-point (month) | Activity (U/ml) | Concentration (mg/ML) | Specific activity (U/mg) | Purity (%) | Visual observation |
|---|---|---|---|---|---|
| 0 | 888 | 41.4 | 21.5 | 99.1 | Colour: 2, clarity: 1 |
| 0.5 | 842 | 50.6 | 16.6 | ND | Colour: 2, clarity: 1 |
| 1 | 746 | 50.6 | 14.8 | 100 | Colour: 2, clarity: 1 |
| 2 | 640 | 52.9 | 12.1 | 100 | Colour: 2, clarity: 1 |
| 3 | 634 | 49.0 | 12.9 | 100 | Colour: 2, clarity: 1 |
| 6 | 422 | 43.0 | 9.8 | 100 | Colour: 2, clarity: 1 |

TABLE 3

Freeze-dried product; 100 mg/ml

| Time-point (month) | Activity (U/ml) | Concentration (mg/ML) | Specific activity (U/mg) | Purity (%) | Visual observation |
|---|---|---|---|---|---|
| 0 | 1944 | 83.7 | 23.2 | 99.1 | Colour: 3, clarity: 1 |
| 1 | 1470 | 98.7 | 14.9 | 100 | Colour: 3, clarity: 1 |
| 2 | 1282 | 94.8 | 13.5 | 100 | Colour: 3, clarity: 1 |
| 3 | 1253 | 82.6 | 15.2 | 100 | Colour: 3, clarity: 1 |
| 6 | 739 | 75.5 | 9.8 | 100 | Colour: 3, clarity: 1 |

TABLE 4

Aqueous product; 5 mg/ml

| Time-point (month) | Activity (U/ml) | Concentration (mg/ML) | Specific activity (U/mg) | Purity (%) | Visual observation |
|---|---|---|---|---|---|
| 0 | 95.6 | 4.0 | 23.7 | 99.1 | Colour: 1, clarity: 1 |
| 0.5 | 48.1 | 5.4 | 8.9 | ND | Colour: 1, clarity: 1 |

TABLE 4-continued

Aqueous product; 5 mg/ml

| Time-point (month) | Activity (U/ml) | Concentration (mg/ML) | Specific activity (U/mg) | Purity (%) | Visual observation |
|---|---|---|---|---|---|
| 1 | 28.6 | 5.9 | 4.8 | 96.1 | Colour: 1, clarity: 1 |
| 1.5 | 12.3 | 5.6 | 2.2 | 91.4 | Colour: 1, clarity: 1 |
| 2 | 4.5 | 4.4 | 1.0 | 90.7 | Colour: 1, clarity: 1 |
| 3 | 7.1 | 3.1 | 2.3 | 87.3 | Colour: 2, clarity: 2 |
| 6 | 4.4 | 2.1 | 2.1 | 58.1 | Colour: 2, clarity: 2 |

Example 2

Concentrating a rhPBGD Composition by Centrifugal Filter Devices

Frozen PBGD-bulk solution (7 mg/mL rhPBGD, 167 mM $Na_2HPO_4$, 27 mM glycine, 250 mM Mannitol, pH 7.9) was thawed in a water-bath at 20° C., centrifuged at 3200 g for 10 min and thereafter sterile-filtrated by 0.20 μm-PES filters (Nalgene Polyethersulfone filters). The PBGD-bulk solution was concentrated to 100 mg/ml by running the Centrifugal Filter Devices Centricon Plus-80 (Mw cut-off 30000) and Centricon Plus-15 (Mw cut-off 30000) at 3200 g for several hours. The concentrated solution, i.e. the retentate, was sterile-filtered by 0.22 μm-filters (Millex GV) and diluted with sterile filtered formulation buffer (see above) to get solutions of lower concentrations. A fraction in volume of each concentration was freeze-dried as described above.

The different concentrations of freeze-dried rhPBGD and aqueous solution of rhPBGD were stored at 5° C.±3° C. or at −20° C.±5° C. (ambient relative humidity (RH)). All vials were stored protected from light in a well-sealed secondary package (paper box).

At the indicated time points (i.e. time of storage) a vial of each freeze-dried samples were resuspended in 1.00 mL Millipore water and then tested together with the aqueous solution of rhPBGD by visually observing the colour, clarity and precipitates, and by measuring pH, protein concentration, purity, osmolality and rhPBGD activity.

The results are given in the following tables 5-19:

TABLE 5

Aqueous product; 11 mg/ml; Storage temp.: +5° C.

| Time-point (month) | Protein conc. (mg/ml) | Activity (U/ml) | Specific activity (U/mg) | Purity (%) | PH | Osmolality (mOsm/kg) | Visual observation Colour 1-3 Clarity 1-3 Solution Aggregates |
|---|---|---|---|---|---|---|---|
| 0 | 10.9 | 255.0 | 23.4 | 100.0 | 7.80 | 290 | Colour: 2 Clarity: 1 Clear None/few |
| 1 | 9.5 | 216.8 | 22.8 | 100.0 | 7.81 | 305 | Colour: 2 Clarity: 1 Clear None/few |
| 2 | 10.9 | 230.2 | 21.1 | 98.0 | 7.80 | 300 | Colour: 2 Clarity: 1 Clear None/few |
| 3 | 11.2 | 226.6 | 20.2 | 100.0 | 7.76 | 290 | Colour: 2 Clarity: 1 Clear Few |
| 6 | 14.7 | 271.1 | 18.4 | 100.0 | 7.77 | 300 | Colour: 2 Clarity: 1 Clear Several |

TABLE 6

Aqueous product: 11 mg/ml; Storage temp: −20° C.

| Time-point (month) | Protein conc. (mg/ml) | Activity (U/ml) | Specific activity (U/mg) | Purity (%) | PH | Osmolality (mOsm/kg) | Visual observation Colour 1-3 Clarity 1-3 Solution Aggregates |
|---|---|---|---|---|---|---|---|
| 0 | 10.4 | 236.1 | 22.6 | 100 | 7.80 | 290 | Colour: 2 Clarity: 1 Clear None |

TABLE 6-continued

Aqueous product: 11 mg/ml; Storage temp: −20° C.

| Time-point (month) | Protein conc. (mg/ml) | Activity (U/ml) | Specific activity (U/mg) | Purity (%) | PH | Osmolality (mOsm/kg) | Visual observation Colour 1-3 Clarity 1-3 Solution Aggregates |
|---|---|---|---|---|---|---|---|
| 1 | 11.7 | 270.3 | 23.1 | 100 | 7.81 | 302 | Colour: 2 Clarity: 1 Clear None |
| 2 | ND | ND | ND | ND | ND | ND | ND |
| 3 | 12.4 | 247.7 | 20.0 | 100 | 7.77 | 288 | Colour: 2 Clarity: 1 Clear None |
| 6 | 13.4 | 291.5 | 21.8 | 100 | 7.77 | 301 | Colour: 2 Clarity: 1 Clear None |

TABLE 7

Freeze-dried product, 11 mg/ml; Storage temp.: +5° C.

| Time-point (month) | Protein conc. (mg/ml) | Activity (U/ml) | Specific activity (U/mg) | Purity (%) | pH | Osmolality (mOsm/kg) | Visual observation Colour 1-3; Clarity 1-3; Solution; Aggregates |
|---|---|---|---|---|---|---|---|
| 0 | 10.9 | 230.0 | 21.2 | 100.0 | 7.80 | 290 | Colour: 2 Clarity: 1 Clear None |
| 1 | ND | ND | ND | ND | ND | ND | ND |
| 2 | ND | ND | ND | ND | ND | ND | ND |
| 3 | 13.3 | 269.3 | 20.2 | 100.0 | 7.74 | 282 | Colour: 2 Clarity: 1 Clear None |
| 6 | 14.7 | 237.9 | 16.2 | 100.0 | 7.76 | 290 | Colour: 2 Clarity: 1 Clear None |

TABLE 8

Aqueous product, 17 mg/ml; Storage temp.: +5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 18.0 | 471.0 | 26.1 | 100.0 | 7.80 | 298 | Colour: 2 Clarity: 1 Clear None/few |
| 1 | 17.5 | 360.4 | 20.6 | 100.0 | 7.81 | 311 | Colour: 2 Clarity: 1 Clear None/few |
| 2 | 18.3 | 397.0 | 21.7 | 100.0 | 7.83 | 302 | Colour: 2 Clarity: 1 Clear None/few |

TABLE 8-continued

Aqueous product, 17 mg/ml; Storage temp.: +5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 3 | 16.6 | 376.5 | 22.7 | 100.0 | 7.77 | 294 | Colour: 2 Clarity: 1 Clear Few |
| 6 | 16.0 | 257.3 | 16.1 | 100.0 | 7.76 | 305 | Colour: 2 Clarity: 1 Clear Several |

TABLE 9

Aqueous product, 17 mg/ml; Storage temp.: −20° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 17.9 | 411.6 | 23.0 | 100.0 | 7.80 | 298 | Colour: 2 Clarity: 1 Clear None |
| 1 | 17.4 | 439.5 | 25.3 | 100.0 | 7.80 | 310 | Colour: 2 Clarity: 1 Clear None |
| 2 | ND | ND | ND | ND | ND | ND | ND |
| 3 | 16.4 | 389.4 | 23.7 | 100.0 | 7.77 | 292 | Colour: 2 Clarity: 1 Clear None |
| 6 | 18.0 | 373.8 | 20.8 | 100.0 | 7.76 | 305 | Colour: 2 Clarity: 1 Clear None |

TABLE 10

Freeze-dried product, 17 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 16.9 | 380.1 | 22.5 | 100.0 | 7.80 | 298 | Colour: 2 Clarity: 1 Clear None |
| 1 | ND | ND | ND | ND | ND | ND | ND |
| 2 | ND | ND | ND | ND | ND | ND | ND |
| 3 | 15.6 | 391.9 | 25.1 | 100.0 | 7.76 | 285 | Colour: 2 Clarity: 1 Clear None |

TABLE 10-continued

Freeze-dried product, 17 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 6 | 16.6 | 341.3 | 20.6 | 100.0 | 7.75 | 297 | Colour: 2 Clarity: 1 Clear None |

TABLE 11

Aqueous product; 36 mg/ml; Storage temp.: +5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 36.0 | 844.4 | 23.4 | 100.0 | 7.81 | 305 | Colour: 2 Clarity: 1 Clear None/few |
| 1 | 35.5 | 778.1 | 21.9 | 100.0 | 7.82 | 314 | Colour: 2 Clarity: 1 Clear None/few |
| 2 | 35.4 | 798.5 | 22.6 | 100.0 | 7.81 | 310 | Colour: 2 Clarity: 1 Clear None/few |
| 3 | 28.9 | 687.9 | 23.8 | 100.0 | 7.77 | 303 | Colour: 2 Clarity: 1 Clear Few |
| 6 | 37.2 | 537.3 | 14.4 | 100.0 | 7.77 | 312 | Colour: 2 Clarity: 1 Clear Several |

TABLE 12

Aqueous product, 36 mg/ml; Storage temp.: −20° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 34.0 | 853.4 | 25.1 | 100.0 | 7.81 | 305 | Colour: 2 Clarity: 1 Clear None |
| 1 | 38.0 | 853.6 | 22.5 | 100.0 | 7.83 | 321 | Colour: 2 Clarity: 1 Clear None |
| 2 | ND | ND | ND | ND | ND | ND | ND |

TABLE 12-continued

Aqueous product, 36 mg/ml; Storage temp.: −20° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 3 | 31.6 | 776.3 | 24.6 | 100.0 | 7.76 | 299 | Colour: 2 Clarity: 1 Clear None |
| 6 | 30.6 | 543.8 | 17.8 | 100.0 | 7.75 | 311 | Colour: 2 Clarity: 1 Clear None |

TABLE 13

Freeze-dried product, 36 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 29.5 | 657.0 | 22.3 | 100.0 | 7.81 | 305 | Colour: 2 Clarity: 1 Clear None |
| 1 | ND | ND | ND | ND | ND | ND | ND |
| 2 | ND | ND | ND | ND | ND | ND | ND |
| 3 | 28.7 | 747.6 | 26.0 | 100.0 | 7.75 | 290 | Colour: 2 Clarity: 1 Clear None |
| 6 | 29.8 | 579.3 | 19.4 | 100.0 | 7.76 | 300 | Colour: 2 Clarity: 1 Clear None |

TABLE 14

Aqueous product, 50 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 46.2 | 780.9 | 16.9 | 96.3 | 7.59 | 317 | Colour: 3 Clarity: 1 Slightly opalescent None |
| 1 | 47.9 | 915 | 19.1 | 90 | 7.58 | 305 | Colour: 3 Clarity: 1 Slightly opalescent None |

TABLE 14-continued

Aqueous product, 50 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 2 | 47.2 | 898.3 | 19.0 | 100 | 7.60 | 318 | Colour: 3 Clarity: 1 Slightly opalescent None |
| 3 | 60.8 | 1102.6 | 18.1 | 100 | 7.72 | 314 | Colour: 3 Clarity: 1 Clear None |
| 6 | 62.5 | 902.8 | 14.4 | 100 | 7.60 | 331 | Colour: 3 Clarity: 2 Clear None |
| 9 | 41.7 | 618.5 | 14.8 | 100 | 7.60 | 336 | Colour: 3 Clarity: 2 Clear None |
| 12 | 50.2 | 540.8 | 10.8 | 97.5 | 7.60 | 329 | Colour: 3 Clarity: 2 Clear None |

TABLE 15

Aqueous product, 50 mg/ml; Storage temp.: −20° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 46.2 | 780.9 | 16.9 | 96.3 | 7.59 | 317 | Colour: 3 Clarity: 1 Slightly opalescent None |
| 1 | 47.2 | 899.1 | 19.0 | 93.7 | 7.58 | 313 | Colour: 3 Clarity: 1 Slightly opalescent None |
| 2 | 53 | 1222.7 | 23.1 | 100.0 | 7.60 | 315 | Colour: 3 Clarity: 1 Slightly opalescent None |
| 3 | 61.2 | 1336.2 | 21.8 | 100.0 | 7.75 | 320 | Colour: 3 Clarity: 1 Slightly opalescent None |
| 6 | 52.2 | 1001.3 | 19.2 | 100.0 | 7.60 | 321 | Colour: 3 Clarity: 1 Slightly opalescent None |
| 12 | 50.4 | 887.9 | 17.6 | 100.0 | 7.60 | 320 | Colour: 3 Clarity: 1 Slightly opalescent None |

TABLE 16

Freeze-dried product, 50 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Cake/solution Aggregates |
|---|---|---|---|---|---|---|---|
| 0 | 42.7 | 759.4 | 17.8 | 100.0 | 7.58 | 292 | Colour: 3 Clarity: 1 Cake: yellow, some cracks Solution: Clear None |
| 1 | 42.6 | 840.4 | 19.7 | 63.1 | 7.58 | 293 | Colour: 3 Clarity: 1 Cake: yellow, some cracks Solution: Clear None |
| 2 | 42.1 | 937.0 | 22.3 | 100.0 | 7.60 | 292 | Colour: 3 Clarity: 1 Cake: yellow, some cracks Solution: Clear None |
| 3 | 47.4 | 1014.7 | 21.4 | 100.0 | 7.75 | 291 | Colour: 3 Clarity: 1 Cake: yellow, some cracks Solution: Clear None |
| 6 | 49.0 | 876.5 | 17.9 | 100.0 | 7.60 | 304 | Colour: 3 Clarity: 1 Cake: yellow, some cracks Solution: Clear None |
| 12 | 51.3 | 945.0 | 18.4 | 100.0 | 7.60 | 308 | Colour: 3 Clarity: 1 Cake: yellow, some cracks Solution: Clear None |

TABLE 17

Aqueous product, 100 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 81.8 | 1705.7 | 20.9 | 99.9 | 7.60 | 350 | Colour: 3 Clarity: 1 Slightly opalescent None |
| 1 | 85.9 | 1942.4 | 22.6 | 96.9 | 7.55 | 352 | Colour: 3 Clarity: 1 Slightly opalescent None |

TABLE 17-continued

Aqueous product, 100 mg/ml; Storage temp.: 5° C.

| Time-point (month) | Protein conc. (mg/ml) | Activity (U/ml) | Specific activity (U/mg) | Purity (%) | PH | Osmolality (mOsm/kg) | Visual observation Colour 1-3 Clarity 1-3 Solution Aggregates |
|---|---|---|---|---|---|---|---|
| 2 | 95.7 | 1690.8 | 17.7 | 96.9 | 7.65 | 357 | Colour: 3 Clarity: 1 Slightly opalescent None |
| 3 | 104.3 | 1671.2 | 16.0 | 100.0 | 7.65 | 350 | Colour: 3 Clarity: 1 Slightly opalescent None |
| 6 | 96.0 | 1642.6 | 17.1 | 100.0 | 7.62 | 360 | Colour: 3 Clarity: 1 Slightly opalescent None |
| 9 | 102.8 | 1270.8 | 12.4 | 100.0 | 7.63 | 352 | Colour: 3 Clarity: 2 Slightly opalescent None |
| 11 | 86.2 | 1140.2 | 13.2 | 100.0 | 7.60 | 353 | Colour: 3 Clarity: 2 Slightly opalescent None |
| 12 | 113.9 | 1550.6 | 13.6 | 100.0 | 7.58 | 350 | Colour: 3 Clarity: 2 Slightly opalescent None |
| 15 | 114.7 | 1160.6 | 10.1 | 98.3 | 7.61 | 350 | Colour: 3 Clarity: 2 Slightly opalescent None |
| 18 | 86.2 | 907.4 | 10.5 | 100.0 | 7.67 | 340 | Colour: 3 Clarity: 2 Slightly opalescent None |

TABLE 18

Aqueous product, 100 mg/ml; Storage temp.: −20° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 0 | 81.8 | 1705.7 | 20.9 | 99.9 | 7.60 | 316 | Colour: 3 Clarity: 1 Slightly opalescent None |
| 1 | 89.3 | 2108.8 | 23.6 | 100.0 | 7.56 | 350 | Colour: 3 Clarity: 1 Slightly opalescent None |
| 2 | 112.0 | 2066.5 | 18.5 | 100.0 | 7.65 | 353 | Colour: 3 Clarity: 1 Slightly opalescent None |

TABLE 18-continued

Aqueous product, 100 mg/ml; Storage temp.: −20° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Solution Aggregates |
|---|---|---|---|---|---|---|---|
| 3 | 100.2 | 2172.4 | 21.7 | 96.7 | 7.65 | 352 | Colour: 3 Clarity: 1 Clear None |
| 6 | 87.5 | 2672.3 | 30.6 | 100.0 | 7.62 | 352 | Colour: 3 Clarity: 1 Clear None |
| 9 | 97.1 | 2040.3 | 21.0 | 100.0 | 7.62 | 353 | Colour: 3 Clarity: 1 Clear None |
| 11 | 104.6 | 2234.0 | 21.4 | 100.0 | 7.60 | 353 | Colour: 3 Clarity: 1 Clear None |
| 12 | 94.5 | 1608.8 | 17.0 | 100.0 | 7.57 | 350 | Colour: 3 Clarity: 1 Slightly opalescent None |
| 15 | 118.0 | 2015.9 | 17.1 | 100.0 | 7.62 | 351 | Colour: 3 Clarity: 1 Slightly opalescent None |
| 18 | 90.6 | 1736.4 | 19.2 | 100.0 | 7.69 | 338 | Colour: 3 Clarity: 1 Slightly opalescent None |

TABLE 19

Freeze-dried product, 100 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Cake/solution Aggregates |
|---|---|---|---|---|---|---|---|
| 0 | 76.0 | 1638.3 | 21.5 | 100.0 | 7.60 | 316 | Colour: 3 Clarity: 1 Cake: Yellow, some cracks Solution: Clear None |
| 1 | 71.6 | 1747.6 | 24.4 | 100.0 | 7.55 | 318 | Colour: 3 Clarity: 1 Cake: Yellow, some cracks Solution: Clear None |
| 2 | 81.6 | 1769.9 | 21.7 | 100.0 | 7.63 | 313 | Colour: 3 Clarity: 1 Cake: Yellow, some cracks Solution: Clear None |

TABLE 19-continued

Freeze-dried product, 100 mg/ml; Storage temp.: 5° C.

| Time-point (month) | Protein conc. (mg/ml) | Activity (U/ml) | Specific activity (U/mg) | Purity (%) | pH | Osmolality (mOsm/kg) | Visual observation Colour 1-3 Clarity 1-3 Cake/solution Aggregates |
|---|---|---|---|---|---|---|---|
| 3 | 84.1 | 1616.6 | 19.2 | 98.2 | 7.65 | 320 | Colour: 3<br>Clarity: 1<br>Cake: Yellow, some cracks<br>Solution: Clear<br>None |
| 6 | 96.7 | 2197.6 | 22.7 | 100.0 | 7.60 | 324 | Colour: 3<br>Clarity: 1<br>Cake: Yellow, some cracks<br>Solution: Clear<br>None |
| 9 | ND | ND | ND | ND | ND | ND | ND |
| 12 | 96.0 | 1978.4 | 20.6 | 100.0 | 7.57 | 322 | Colour: 3<br>Clarity: 1<br>Cake: Yellow, some cracks<br>Solution: Clear<br>None |
| 15 | ND | ND | ND | ND | ND | ND | ND |
| 18 | 80.6 | 1602.6 | 19.9 | 100.0 | 7.75 | 310 | Colour: 3<br>Clarity: 1<br>Cake: Yellow, some cracks<br>Solution: Clear<br>None |

Example 3

Concentrating a rhPBGD Composition by Tangential Flow Filtration (TFF)

The bulk solution of rhPBGD was then thawed for a minimum of three days at 5° C. and in darkness.

The thawed solution was then centrifuged with 200 mL conical centrifuge tubes for approximately 10 minutes at 2200 g.

The solution was then filtered through a series of filters with the following pore-sizes: 5.0 μm; 0.65 μm; 0.45 μm and 0.20 μm before it was concentrated by tangential flow filtration (TFF).

The concentration by TFF was performed with a Millipore Labscale TFF System and Millipore Pellicon® XL Filter with a pump inlet pressure of approximately 20-25 psi and a pressure over the Pellicon® XL Filter of approximately 4-6 psi. The rhPBGD was protected from light during the procedure by covering the sample container of the TFF System by sheets of aluminium foil.

The concentrated rhPBGD solution obtained from the TFF procedure was then buffer-changed against a formulation buffer containing 3.67 mM $Na_2HPO_4 \times 2H_2O$, 27 mM glycin and 220 mM Mannitol prepared in sterile water. This was performed by continuously adding said buffer to the TFF-system and pressing it across the membrane until said buffer has replaced the previous buffer.

The concentrated and buffer-changed rhPBGD solution was then sterile filtered by passing it through a filter with a pore-size of 0.22 μm. This sterile filtration was performed twice with a new filter each time.

The sterile concentrated rhPBGD solution was then placed in vials before it was freeze-dried as described in the method section.

Example 4

The Effect of Different Modes of Freeze-Drying and/or the Amount of Excipients on the Reconstitution Time PBGD was concentrated as described in example 3 and after the exchange of the buffer was the concentration of PBGD determined.

The concentrated PBGD solution was then freeze-dried in a Lyostar (FTM-systems) freeze-dryer. The solutions were filled in 2 and 6 ml injection glass vials (type 1) and stoppered with rubber stoppers (chlorobutyl).

Original Freeze-Drying Cycle:

The samples were loaded in ambient temperature and the shelves were cooled down to 0° C. for 30 minutes. The temperature were lowered to −40° C. (1° C. per minute) and held there for 30 minutes and then the vacuum pressure was drawn to 126 mTorr and the primary drying began by raising the temperature to 0° C. (1° C. per minute). After 360 minutes of primary drying the temperature was raised to +30° C. (0.5° C. per minute) and full vacuum was drawn simultaneously (start of secondary drying). The temperature was held at +30° C. for 360 minutes and the vials were then stoppered under vacuum.

Freeze-Drying with Inclusion of an Annealing Step:

After 30 minutes at −40° C. the temperature was raised with a rate of 2° C. per minute to −10° C. or −20° C. at which temperature they were kept for 120 or 420 minutes before the temperature was lowered again with 2° C. per minute to −40° C. were the samples were kept for 60-90 minutes before start of primary drying.

The results are shown in Table 20 where the short terms used with regard to the excipients and the freeze-drying cycle mean the following:

1× amount of excipients refers to that the PBGD solution comprises 3.67 mM $Na_2HPO_4 \times 2H_2O$, 27 mM glycin and 220 mM Mannitol prepared in sterile water.

1.5× amount excipients refers to that the PBGD solution comprises 5.51 mM $Na_2HPO_4 \times 2H_2O$, 40.5 mM glycin and 375 mM Mannitol prepared in sterile water, i.e. 1.5× of each of the components present in the 1× buffer.

2× excipients refers to that the PBGD solution comprises 7.34 mM $Na_2HPO_4 \times 2H_2O$, 54 mM glycin and 500 mM Mannitol prepared in sterile water, i.e. 2× of each of the components present in the 1× buffer.

The original freeze-drying cycle is as described above.

The annealing freeze-drying cycle is as described above where the annealing step comprises raising the temperature to −10° C. at keeping the sample at this temperature for 120 minutes before lowering it to −40° C. again.

The extended annealing freeze-drying cycle is as described above where the annealing step comprises raising the temperature to −20° C. at keeping the sample at this temperature for 420 minutes before lowering it to −40° C. again.

TABLE 20

| Amount of excipients | Protein concentration (mg/ml) | Reconstitution time for different free-drying cycles | | |
|---|---|---|---|---|
| | | Original | Annealing | Extended annealing |
| 1× | 198 | 600 | 550 | 480 |
| 1× | 175 | 540 | 500 | 450 |
| 1× | 150 | 450 | 480 | 180 |
| 1× | 125 | 330 | 100 | 10 |
| 1× | 100 | 40 | 10 | 10 |
| 1× | 80 | 25 | 10 | 10 |
| 1.5× | 200 | 480 | 40 | 60 |
| 1.5× | 175 | 220 | 10 | 10 |
| 1.5× | 150 | 60 | 10 | 10 |
| 1.5× | 125 | 15 | 10 | 10 |
| 1.5× | 100 | 10 | 10 | 10 |
| 2× | 200 | 120 | | 20 |
| 2× | 175 | 40 | | 20 |
| 2× | 150 | 20 | | 10 |
| 2× | 100 | 10 | | 10 |

Example 5

The Effect of Different Modes of Freeze-Drying and/or the Amount of Excipients on the Appearance of the Freeze-Dried Product Concentrated and freeze-dried solutions of PBGD were prepared as described in example 4 and references to the amount of excipients and the type of freeze-drying cycle has the same meaning as in example 4.

The following results were obtained by visual inspection of the freeze-dried products:

A: Comparison of three products prepared from solutions comprising respectively, 4.6 mg/ml 66.6 mg/ml and 109.4 mg/ml rhPBGD showed that the number of cracks in the freeze-dried product increased as concentration of rhPBGD increased.

B: Comparison of two products, prepared from a solution comprising 150 mg/ml rhPBGD, and comprising 1× and 1.5× amount of excipients showed that the number of cracks in the freeze-dried product was lower for the product which comprised 1.5× amount of excipients than the product comprising 1× amount of excipients.

C: Comparison of two freeze-dried products prepared from a 150 mg/ml rhPBGD solution, comprising 1× and 2× amount of excipients showed that the number of cracks in the freeze-dried product with 2× amount of excipients was lower than the product comprising the 1× amount of excipients.

D: Comparison of three freeze-dried products prepared from a 150 mg/ml rhPBGD solution by using the original, the annealing and the extended annealing freeze-drying cycle showed that the number of cracks in the freeze-dried product was lower in the product which was prepared according to the annealing freeze-drying cycle than in the product prepared according to the original freeze-drying cycle. Furthermore, the number of cracks in the product prepared according to the extended annealing freeze-drying cycle was lower than in the product prepared according to the annealing freeze-drying cycle.

E: Three freeze-dried products were prepared from a 150, 175 and 200 mg/ml, respectively, rhPBGD solution. The freeze-dried products each comprised 1.5× amount of excipients and they were freeze-dried with the annealing cycle. None of the freeze-dried products comprised any cracks.

F: Two freeze-dried rhPBGD products were prepared from a 150 mg/ml rhPBGD solution. One of them comprised 1× amount of excipients and was prepared according to the original freeze-drying cycle, while the other comprised 1.5× amount of excipients and was prepared according to the extended annealing free-drying cycle. The product comprising 1.5× amount of excipients and prepared according to the extended annealing freeze-drying cycle comprised fewer cracks than the product comprising 1× amount of excipients and prepared according to the original freeze-drying cycle.

G: Two freeze-dried rhPBGD products were prepared from a 150 mg/ml rhPBGD solution. One of them comprised 1× amount of excipients and was prepared according to the original freeze-drying cycle, while the other comprised 0.1% Tween 80 in combination with the 1× amount of excipients and was prepared according to the extended annealing freeze-drying cycle. The product comprising the 0.1% Tween 80 in combination with the 1× amount of excipients and which was prepared according to the extended annealing freeze-drying cycle comprised fewer cracks than the product which comprised 1× amount of excipients and which was prepared according to the original freeze-drying cycle.

Example 6

The Effect of Recovery Volume, the Amount of Excipients and the Mode of Freeze-Drying on the Stability of Freeze-Dried rhPBGD Concentrated rhPBGD solutions freeze-dried samples were prepared as described in example 4.

The "bulk solution" is a concentrated solution of PBGD before freeze-drying.

Table 21 shows the results of rhPBGD solutions having the following characteristics with regard to the concentration of rhPBGD, amount of excipients (were the same definitions as in example 4 are used), the mode of freeze-drying (were the same definitions as in example 4 are used) and the ratio of the filling volume (fill. Vol which is the volume of the composition before it is freeze-dried) versus the recovery volume (Rec. vol which is the volume in which the freeze-dried product is resuspended):

Solution 1:
 Approximately 5 mg/ml rhPBGD
 1× amount of excipient
 Original freeze-drying cycle
 Fill.vol=Rec. vol Solution 2:
 Approximately 70 mg/ml rhPBGD
 1× amount of excipient
 Original freeze-drying cycle
 Fill.vol=2×Rec. vol Solution 3:
 Approximately 110 mg/ml rhPBGD
 1× amount of excipient
 Original freeze-drying cycle
 Fill.vol=Rec. vol Solution 4:
 Approximately 70 mg/ml rhPBGD
 1× amount of excipient
 Original freeze-drying cycle
 Fill.vol=1.5×Rec. vol Solution 5:
 Approximately 90 mg/ml rhPBGD
 ⅔× amount of excipient
 Original freeze-drying cycle
 Fill.vol=1.5×Rec. vol Solution 6:
 Approximately 60 mg/ml rhPBGD
 ½× amount of excipient
 Original freeze-drying cycle
 Fill.vol=2×Rec. vol Solution 7:
 Approximately 110 mg/ml rhPBGD
 1× amount of excipient
 Annealing freeze-drying cycle
 Fill.vol=Rec. vol Solution 8:
 Approximately 60 mg/ml rhPBGD
 1× amount of excipient
 Annealing freeze-drying cycle
 Fill.vol=2×Rec. vol Solution 9:
 Approximately 150 mg/ml rhPBGD
 1× amount of excipient
 Annealing freeze-drying cycle
 Fill.vol=Rec. vol Solution 10:
 Approximately 150 mg/ml rhPBGD
 1× amount of excipient
 Original freeze-drying cycle
 Fill.vol=Rec. vol Although not shown in Table 21 the purity was also tested for each time point as was found to 100% in all cases.

For solution 2 at the week 4 and 9 time point and for solution 4 the week 9 time point a wrong recovery volume was used.

TABLE 21

| Solution | Measuring point (week) | Fill. Vol (ml) | Rec. Vol (ml) | pH | Osmolality (mosmol/kg) | Protein concentration (mg/ml) | Activity (U/ml) | Specific activity (U/mg) |
|---|---|---|---|---|---|---|---|---|
| 1 | bulk | | | | | 4.6 | 78 | 17.1 |
| | 0 | 0.67 | 0.67 | 7.54 | 274 | 4.8 | 85 | 17.8 |
| | 2 | 0.67 | 0.67 | 7.22 | 274 | 4.6 | 87 | 19.4 |
| | 4 | 0.67 | 0.67 | 7.78 | 279 | 5.1 | 75 | 14.5 |
| | 7 | 0.67 | 0.67 | 7.87 | 284 | 5.1 | 68 | 13.3 |
| | 9 | 0.67 | 0.67 | 7.67 | 403 | 7.0 | 93 | 13.2 |
| 2 | bulk | | | | | 66.6 | 1129 | 16.9 |
| | 0 | 0.67 | 0.335 | 7.64 | 525 | 113 | 1915 | 16.9 |
| | 2 | 0.67 | 0.335 | 7.63 | 459 | 93.6 | 1593 | 17.0 |
| | 4 | 0.67 | 0.67 | 7.75 | 264 | 64.6 | 1104 | 17.1 |
| | 7 | 0.67 | 0.335 | 7.95 | 451 | 106.4 | 2106 | 19.8 |
| | 9 | 0.67 | 0.67 | 7.59 | 247 | 51.4 | 859 | 16.7 |
| 3 | bulk | | | | | 109.4 | 1491 | 13.6 |
| | 0 | 0.67 | 0.67 | 7.75 | 274 | 99.9 | 1598 | 16.0 |
| | 2 | 0.67 | 0.67 | 7.64 | 269 | 91.4 | 1543 | 16.9 |
| | 4 | 0.67 | 0.67 | 7.68 | 274 | 101.2 | 1825 | 18.0 |
| | 7 | 0.67 | 0.67 | 7.71 | 278 | 103.4 | 2045 | 19.8 |
| | 9 | 0.67 | 0.67 | 7.67 | 274 | 88.3 | 1656 | 18.8 |
| 4 | bulk | | | | | 71.5 | 1244 | 17.4 |
| | 0 | 0.67 | 0.45 | 7.64 | 448 | 113.8 | 1748 | 15.4 |
| | 2 | 0.67 | 0.45 | 7.63 | 411 | 86.4 | 1806 | 20.9 |
| | 4 | 0.67 | 0.45 | 7.77 | 362 | 109.9 | 1897 | 17.3 |
| | 7 | 0.67 | 0.45 | 7.90 | 379 | 95.2 | 686 | (7.2) |
| | 9 | 0.67 | 0.67 | 7.63 | 273 | 59.7 | 1090 | 18.3 |
| 5 | bulk | | | | | 91.0 | 1610 | 17.7 |
| | 0 | 0.67 | 0.45 | 7.65 | 296 | 119.4 | 2014 | 16.9 |
| | 2 | 0.67 | 0.45 | 7.61 | 285 | 112.3 | 2093 | 18.6 |
| | 4 | 0.67 | 0.45 | 7.90 | 292 | 125.1 | 2409 | 19.3 |
| | 7 | 0.67 | 0.45 | 7.88 | 297 | 116.4 | 1928 | 16.6 |
| | 9 | 0.67 | 0.45 | 7.34 | 278 | 102.5 | 1490 | 14.5 |
| 6 | bulk | | | | | 60.7 | 992 | 16.3 |
| | 0 | 0.67 | 0.335 | 7.63 | 295 | 112.6 | 1753 | 15.6 |
| | 2 | 0.67 | 0.335 | 7.60 | 288 | 86.9 | 1787 | 20.6 |
| | 4 | 0.67 | 0.335 | 7.83 | 287 | 116.4 | 2106 | 18.1 |
| | 7 | 0.67 | 0.335 | 8.20 | 299 | 109.7 | 695 | (6.3) |
| | 9 | 0.67 | 0.335 | 7.44 | 287 | 95.2 | 1636 | 17.2 |

TABLE 21-continued

| Solution | Measuring point (week) | Fill. Vol (ml) | Rec. Vol (ml) | pH | Osmolality (mosmol/kg) | Protein concentration (mg/ml) | Activity (U/ml) | Specific activity (U/mg) |
|---|---|---|---|---|---|---|---|---|
| 7 | bulk | | | | | 116.4 | 1926 | 16.5 |
|   | 0 | 0.67 | 0.67 | 7.56 | 275 | 101.1 | 1750 | 17.3 |
|   | 2 | 0.67 | 0.67 | 7.51 | 276 | 93.4 | 1831 | 19.6 |
|   | 4 | 0.67 | 0.67 | 7.60 | 270 | 101.6 | 1774 | 17.5 |
|   | 7 | 0.67 | 0.67 | 7.53 | 283 | 102.2 | 1639 | 16.0 |
|   | 9 | 0.67 | 0.67 | 7.46 | 274 | 89.9 | 960 | 10.7 |
| 8 | bulk | | | | | 64.5 | 1119 | 17.4 |
|   | 0 | 0.67 | 0.335 | 7.52 | 511 | 100.7 | 1718 | 17.1 |
|   | 2 | 0.67 | 0.335 | 7.51 | 459 | 99.3 | 1900 | 19.1 |
|   | 4 | 0.67 | 0.335 | 7.70 | 482 | 114.5 | 1913 | 16.7 |
|   | 9 | 0.67 | 0.335 | 7.29 | 425 | 102.3 | 1650 | 16.1 |
| 9 | bulk | | | | | 165 | 3587 | 21.7 |
|   | 0 | 0.60 | 0.60 | 7.71 | 309 | 121.4 | 2819 | 23.2 |
|   | 4 | 0.60 | 0.60 | 7.74 | — | 140.3 | 2014 | 14.4 |
|   | 7.5 | 0.60 | 0.60 | 7.61 | 292 | 135.9 | 1640 | 12.1 |
| 10 | bulk | | | | | 165 | 3587 | 21.7 |
|   | 0 | 0.60 | 0.60 | 7.86 | 276 | 142.1 | 2397 | 16.9 |
|   | 3 | 0.40 | 0.40 | 8.20 | 314 | 141.9 | 2381 | 16.8 |
|   | 5 | 0.60 | 0.60 | 7.60 | 302 | 131.8 | 2304 | 17.5 |

Example 7

Effect of Different Excipients on the Stability of rhPBGD rhPBGD was concentrated as described in example 4 and then the buffer was changed as to one of the four buffers described below. The products were then freeze-dried as described in example 4 with an original annealing step included and the stability of the samples were tested as described in example 6.

The effect of the following four formulations on the stability of rhPBGD was tested:

Formulation A (corresponds to solution 9 in example 6): 250 mM mannitol, 27 mM glycine and 3.67 mM $Na_2HPO_4$.

Formulation B: 250 mM mannitol, 27 mM glycine and 10 mM TRIS-HCL.

Formulation C: 250 mM mannitol, 27 mM glycine, 3.67 mM $Na_2HPO_4$ and 0.1% Tween 80.

Formulation D: 221 mM mannitol, 29 mM sucrose, 27 mM glycine, 3.67 mM $Na_2HPO_4$ and 0.1% Tween 80.

The results are shown in Table 22.

TABLE 22

| Formulation | Measuring point (week) | Fill. Vol (ml) | Rec. Vol (ml) | pH | Osmolality (mosmol/kg) | Protein concentration (mg/ml) | Activity (U/ml) | Specific activity (U/mg) |
|---|---|---|---|---|---|---|---|---|
| A | Bulk | | | 7.69 | 366 | 165 | 3587 | 21.7 |
|   | 0 | 0.60 | 0.60 | 7.71 | 309 | 121.4 | 2819 | 23.2 |
|   | 4 | 0.60 | 0.60 | 7.74 | — | 140.3 | 2014 | 14.4 |
|   | 7.5 | 0.60 | 0.60 | 7.61 | 292 | 135.9 | 1640 | 12.1 |
| B | Bulk | | | 7.54 | 320 | 173 | 3595 | 20.8 |
|   | 0 | 0.60 | 0.60 | 7.58 | 284 | 148.1 | 3726 | 25.2 |
|   | 3 | 0.60 | 0.60 | 7.57 | 280 | 165.4 | 2947 | 17.8 |
|   | 4 | 0.60 | 0.60 | 7.69 | — | 167.5 | 2367 | 14.1 |
|   | 7.5 | 0.60 | 0.60 | 7.60 | 283 | 150.4 | 2235 | 14.9 |
| C | Bulk | | | 7.40 | 338 | 178 | 3606 | 20.2 |
|   | 0 | 0.60 | 0.60 | 7.76 | 290 | 142.9 | 2662 | 18.6 |
|   | 3 | 0.60 | 0.60 | 7.43 | 285 | 181.7 | 2332 | 12.8 |
|   | 4 | 0.60 | 0.60 | 7.42 | — | 173.1 | 1436 | 8.3 |
|   | 6 | 0.60 | 0.60 | 7.55 | 274 | 156.6 | 1254 | 7.4 |
|   | 7.5 | 0.60 | 0.60 | 7.34 | 274 | 141.5 | 1252 | 8.9 |
| D | Bulk | | | 7.41 | 337 | 175 | 3869 | 22.1 |
|   | 0 | 0.60 | 0.60 | 7.80 | 292 | 127.5 | 2355 | 18.5 |
|   | 3 | 0.60 | 0.60 | 7.35 | 288 | 143.9 | 1988 | 13.8 |
|   | 4 | 0.60 | 0.60 | 7.26 | — | 159.3 | 1644 | 10.3 |
|   | 6 | 0.60 | 0.60 | 7.30 | 281 | 135.7 | 1236 | 9.1 |
|   | 7.5 | 0.60 | 0.60 | 7.28 | 282 | 125.7 | 1146 | 9.1 |

The invention claimed is:

1. A method of treating metachromatic leukodystrophy comprising administering to a subject in need of treatment a composition comprising at least 25 mg/mL recombinant human arylsulfatase A (rhASA), wherein the amount of rhASA present as aggregates constitutes at least few and less than 5 w/w % of the total amount of rhASA in the composition.

2. The method of claim 1, wherein the rhASA is present at a concentration no greater than 500 mg/mL.

3. The method of claim 1, wherein the composition is an aqueous solution.

4. The method of claim 1, wherein the composition further comprises a detergent.

5. The method of claim 1, wherein the rhASA contains mannose-6-phosphate residues.

6. The method of claim 1, wherein the rhASA comprises an amino acid sequence selected from the group consisting of
   (i) an amino acid sequence as defined by any one of SEQ ID NOs: 18, 19, or 20; and
   (ii) an amino acid sequence at least 95% identical to any one of SEQ ID NOs: 18, 19, or 20.

7. The method of claim 1, wherein the rhASA is produced in mammalian host cells.

8. The method of claim 7, wherein the mammalian host cells are human cells.

9. The method of claim 7, wherein the mammalian host cells are Chinese Hamster Ovary (CHO) cells.

* * * * *

SEQUENCE LISTING

<160> NUMBER OF SEQ ID NOS: 26

<210> SEQ ID NO 1
<211> LENGTH: 1035
<212> TYPE: DNA

<213> ORGANISM: Homo sapiens

<400> SEQUENCE: 1

| | |
|---|---|
| atgagagtga ttcgcgtggg tacccgcaag agccagcttg ctcgcataca gacggacagt | 60 |
| gtggtggcaa cattgaaagc ctcgtaccct ggcctgcagt ttgaaatcat tgctatgtcc | 120 |
| accacagggg acaagattct tgatactgca ctctctaaga ttggagagaa aagcctgttt | 180 |
| accaaggagc ttgaacatgc cctggagaag aatgaagtgg acctggttgt tcactccttg | 240 |
| aaggacctgc ccactgtgct tcctcctggc ttcaccatcg agccatctg caagcgggaa | 300 |
| aaccctcatg atgctgttgt cttcacccca aaatttgttg ggaagaccct agaaaccctg | 360 |
| ccagagaaga gtgtggtggg aaccagctcc ctgcgaagag cagcccagct gcagagaaag | 420 |
| ttcccgcatc tggagttcag gagtattcgg ggaaaccctca acacccggct tcggaagctg | 480 |
| gacgagcagc aggagttcag tgccatcatc ctggcaacag ctggcctgca gcgcatgggc | 540 |
| tggcacaacc gggttgggca gatcctgcac cctgaggaat gcatgtatgc tgtgggccag | 600 |
| ggggccttgg gcgtggaagt gcgagccaag gaccaggaca tcttggatct ggtgggtgtg | 660 |
| ctgcacgatc ccgagactct gcttcgctgc atcgctgaaa gggccttcct gaggcacctg | 720 |
| gaaggaggct gcagtgtgcc agtagccgtg catacagcta tgaaggatgg gcaactgtac | 780 |
| ctgactggag gagtctggag tctagacggc tcagatagca tacaagagac catgcaggct | 840 |
| accatccatg tccctgccca gcatgaagat ggccctgagg atgacccaca gttggtaggc | 900 |
| atcactgctc gtaacattcc acgagggccc cagttggctg cccagaactt gggcatcagc | 960 |
| ctggccaact tgttgctgag caaaggagcc aaaaacatcc tggatgttgc acggcaattg | 1020 |
| aacgatgccc attaa | 1035 |

<210> SEQ ID NO 2
<211> LENGTH: 1035
<212> TYPE: DNA
<213> ORGANISM: Homo sapiens

<400> SEQUENCE: 2

| | |
|---|---|
| atgagagtga ttcgcgtggg tacccgcaag agccagcttg ctcgcataca gacggacagt | 60 |
| gtggtggcaa cattgaaagc ctcgtaccct ggcctgcagt ttgaaatcat tgctatgtcc | 120 |
| accacagggg acaagattct tgatactgca ctctctaaga ttggagagaa aagcctgttt | 180 |
| accaaggagc ttgaacatgc cctggagaag aatgaagtgg acctggttgt tcactccttg | 240 |
| aaggacctgc ccactgtgct tcctcctggc ttcaccatcg agccatctg caagcgggaa | 300 |
| aaccctcatg atgctgttgt cttcacccca aaatttgttg ggaagaccct agaaaccctg | 360 |
| ccagagaaga gtgtggtggg aaccagctcc ctgcgaagag cagcccagct gcagagaaag | 420 |
| ttcccgcatc tggagttcag gagtattcgg ggaaaccctca acacccggct tcggaagctg | 480 |
| gacgagcagc aggagttcag tgccatcatc ctggcaacag ctggcctgca gcgcatgggc | 540 |
| tggcacaacc gggtggggca gatcctgcac cctgaggaat gcatgtatgc tgtgggccag | 600 |
| ggggccttgg gcgtggaagt gcgagccaag gaccaggaca tcttggatct ggtgggtgtg | 660 |
| ctgcacgatc ccgagactct gcttcgctgc atcgctgaaa gggccttcct gaggcacctg | 720 |
| gaaggaggct gcagtgtgcc agtagccgtg catacagcta tgaaggatgg gcaactgtac | 780 |
| ctgactggag gagtctggag tctagacggc tcagatagca tacaagagac catgcaggct | 840 |
| accatccatg tccctgccca gcatgaagat ggccctgagg atgacccaca gttggtaggc | 900 |
| atcactgctc gtaacattcc acgagggccc cagttggctg cccagaactt gggcatcagc | 960 |

```
ctggccaact tgttgctgag caaaggagcc aaaaacatcc tggatgttgc acggcaattg    1020
aacgatgccc attaa                                                    1035

<210> SEQ ID NO 3
<211> LENGTH: 1035
<212> TYPE: DNA
<213> ORGANISM: Homo sapiens

<400> SEQUENCE: 3
atgagagtga ttcgcgtggg tacccgcaag agccagcttg ctcgcataca gacggacagt      60
gtggtggcaa cattgaaagc tcgtaccct ggcctgcagt ttgaaatcat tgctatgtcc     120
accacagggg acaagattct tgatactgca ctctctaaga ttggagagaa aagcctgttt     180
accaaggagc ttgaacatgc cctggagaag aatgaagtgg acctggttgt tcactccttg     240
aaggacctgc ccactgtgct tcctcctggc ttcaccatcg agccatctg caagcgggaa     300 aaccctcatg atgctgttgt ctttcaccca aaatttgttg gaagacccct agaaaccctg     360
ccagagaaga gtgtggtggg aaccagctcc ctgcgaagag cagcccagct gcagagaaag     420
ttcccgcatc tggagttcag gagtattcgg ggaaaccctca acccggct cggaagctg     480 gacgagcagc aggagttcag tgccatcatc ctggcaacag ctggcctgca gcgcatgggc     540
tggcacaacc gggtggggca gatcctgcac cctgaggaat gcatgtatgc tgtgggccag     600
ggggccttgg gcgtggaagt gcgagccaag gaccaggaca tcttggatct ggtgggtgtg     660
ctgcacgatc ccgagactct gcttcgctgc atcgctgaaa gggccttcct gaggcacctg     720
gaaggaggct gcagtgtgcc agtagccgtg catacagcta tgaaggatgg gcaactgtac     780
ctgactggag gagtctggag tctagacggc tcagatagca tacaagagac catgcaggct     840
accatccatg tccctgccca gcatgaagat ggccctgagg atgacccaca gttggtaggc     900
atcactgctc gtaacattcc acgagggccc cagttggctg cccagaactt gggcatcagc     960
ctggccaact tgttgctgag caaaggagcc aaaaacatcc tggatgttgc acggcaattg    1020
aacgatgccc attaa                                                    1035

<210> SEQ ID NO 4
<211> LENGTH: 1034
<212> TYPE: DNA
<213> ORGANISM: Homo sapiens

<400> SEQUENCE: 4
atgagagtga ttcgcgtggg tacccgcaag agccagcttg ctcgcataca gacggacagt      60
gtggtggcaa cattgaaagc tcgtaccct ggcctgcagt ttgaaatcat tgctatgtcc     120
accacagggg acaagattct tgatactgca ctctctaaga ttggagagaa aagcctgttt     180
accaaggagc ttgaacatgc cctggagaag aatgaagtgg acctggttgt tcactccttg     240
aaggacctgc ccactgtgct tcctcctggc ttcaccatcg agccatctg caagcgggaa     300 aaccctcatg atgctgttgt cttcacccaa aatttgttgg aagacccta gaaaccctgc     360 cagagaagag tgtggtggga accagctccc tgcgaagagc agcccagctg cagagaaagt     420
tcccgcatct ggagttcagg agtattcggg gaaacctcaa cacccggctt cggaagctgg     480
acgagcagca ggagttcagt gccatcatcc tggcaacagc tggcctgcag cgcatgggct     540
ggcacaaccg ggtggggcag atcctgcacc ctgaggaatg catgtatgct gtgggccagg     600
ggccttgggc gtggaagtgc gagccaagg accaggacat cttggatctg gtgggtgtgc     660
```

| | |
|---|---|
| tgcacgatcc cgagactctg cttcgctgca tcgctgaaag ggccttcctg aggcacctgg | 720 |
| aaggaggctg cagtgtgcca gtagccgtgc atacagctat gaaggatggg caactgtacc | 780 |
| tgactggagg agtctggagt ctagacggct cagatagcat acaagagacc atgcaggcta | 840 |
| ccatccatgt ccctgcccag catgaagatg gccctgagga tgacccacag ttggtaggca | 900 |
| tcactgctcg taacattcca cgagggcccc agttggctgc ccagaacttg ggcatcagcc | 960 |
| tggccaactt gttgctgagc aaaggagcca aaaacatcct ggatgttgca cggcaattga | 1020 |
| acgatgccca ttaa | 1034 |

<210> SEQ ID NO 5
<211> LENGTH: 1035
<212> TYPE: DNA
<213> ORGANISM: Homo sapiens

<400> SEQUENCE: 5

| | |
|---|---|
| atgagagtga ttcgcgtggg tacccgcaag agccagcttg ctcgcataca gacgggcagt | 60 |
| gtggtggcaa cattgaaagc ctcgtaccct ggcctgcagt ttgaaatcat tgctatgtcc | 120 |
| accacagggg acaagattct tgatactgca ctctctaaga ttggagagaa aagcctgttt | 180 |
| accaaggagc ttgaacatgc cctggagaag aatgaagtgg acctggttgt tcactccttg | 240 |
| aaggacctgc ccactgtgct tcctcctggc ttcaccatcg agccatctg caagcgggaa | 300 |
| aaccctcatg atgctgttgt cttcacccca aatttgttg gaagacccct agaaccctg | 360 |
| ccagagaaga gtgtggtggg aaccagctcc ctgcgaagag cagcccagct gcagagaagg | 420 |
| ttcccgcatc tggagttcag gagtattcgg ggaaacctca cacccggct cggaagctg | 480 |
| gacgagcagc aggagttcag tgtcatcatc ctggcaacag ctggcctgca cgcatgggc | 540 |
| tggcacaacc gggttgggca gatcctgcac cctgaggaat gcatgtatgc tgtgggccag | 600 |
| ggggccttgg gcgtggaagt gcgagccaag gaccaggaca tcttggatct ggtgggtgtg | 660 |
| ctgcacgatc ccgagactct gcttcgctgc atcgctgaaa gggccttcct gaggcacctg | 720 |
| gaaggaggct gcagtgtgcc agtagccgtg catacagcta tgaaggatgg gcaactgtac | 780 |
| ctgactggag gagtctggag tctagacggc tcagatagca tacaagagac catgcaggct | 840 |
| accatccatg tccctgccca gcatgaagat ggccctgagg atgacccaca gttggtaggc | 900 |
| atcactgctc gtaacattcc acgagggccc cagttggctg cccagaactt gggcatcagc | 960 |
| ctggccaact tgttgctgag caagggagcc aaaaacatcc tggatgttgc acggcaattg | 1020 |
| aacgatgccc attaa | 1035 |

<210> SEQ ID NO 6
<211> LENGTH: 1035
<212> TYPE: DNA
<213> ORGANISM: Homo sapiens

<400> SEQUENCE: 6

| | |
|---|---|
| atgagagtga ttcgcgtggg tacccgcaag agccagcttg ctcgcataca gacggacagt | 60 |
| gtggtggcaa cattgaaagc ctcgtaccct ggcctgcagt ttgaaatcat tgctatgtcc | 120 |
| accacagggg acaagattct tgatactgca ctctctaaga ttggagagaa aagcctgttt | 180 |
| accaaggagc ttgaacatgc cctggagaag aatgaagtgg acctggttgt tcactccttg | 240 |
| aaggacctgc ccactgtgct tcctcctggc ttcaccatcg agccatctg caagcgggaa | 300 |
| aaccctcatg atgctgttgt cttcacccca aatttgttg gaagacccct agaaccctg | 360 |
| ccagagaaga gtgtggtggg aaccagctcc ctgcgaagag cagcccagct gcagagaaag | 420 |

```
ttcccgcatc tggagttcag gagtattcgg ggaaacctca acacccggct tcggaagctg      480
gacgagcagc aggagttcag tgccatcatc ctggcaacag ctggcctgca gcgcatgggc      540
tggcacaacc gggtggggca gatcctgcac cctgaggaat gcatgtatgc tgtgggccag      600
ggggccttgg gcgtggaagt gcgagccaag gaccaggaca tcttggatct ggtgggtgtg      660
ctgcacgatc ccgagactct gcttcgctgc atcgctgaaa gggccttcct gaggcacctg      720
gaaggaggtt gcagtgtgcc agtagccgtg catacagcta tgaaggatgg gcaactgtac      780
ctgactggag gagtctggag tctagacggc tcagatagca tacaagagac catgcaggct      840
accatccatg tccctgccca gcatgaagat ggccctgagg atgacccaca gttggtaggc      900
atcactgctc gtaacattcc acgagggccc cagttggctg cccagaactt gggcatcagc      960
ctggccaact tgttgctgag caaaggagcc aaaaacatcc tggatgttgc acggcaattg     1020
aacgatgccc attaa                                                      1035

<210> SEQ ID NO 7
<211> LENGTH: 1034
<212> TYPE: DNA
<213> ORGANISM: Homo sapiens

<400> SEQUENCE: 7
atgagagtga ttcgcgtggg tacccgcaag agccagcttg ctcgcataca gacggacagt       60
gtggtggcaa cattgaaagc ctcgtaccct ggcctgcagt ttgaaatcat tgctatgtcc      120
accacagggg acaagattct tgatactgca ctctctaaga ttggagagaa agcctgttt       180 accaaggagc ttgaacatgc cctggagaag aatgaagtgg acctggttgt tcactccttg      240
aaggacctgc ccactgtgct tcctcctggc ttcaccatcg agccatctg caagcgggaa       300 aaccctcatg atgctgttgt cttttcaccca aaatttgttg ggaagaccct agaaaccctg      360
ccagagaaga gtgtggtggg aaccagctcc ctgcgaagag cagcccagct gcagagaaag      420
ttcccgcatc tggagttcag gagtattcgg ggaaacctca acacccggct tcggaagctg      480
gacgagcagc aggagttcag tgccatcatc ctggcaacag ctggcctgca gcgcatgggc      540
tggcacaacc gggtggggca gatcctgcac cctgaggaat gcatgtatgc tgtgggccag      600
ggggccttgg gcgtggaagt gcgagccaag gaccaggaca tcttggatct ggtgggtgtg      660
ctgcacgatc ccgagactct gcttcgctgc atcgctgaaa gggccttcct gaggcacctg      720
gaaggaggct gcagtgtgcc agtagccgtg catacagcta tgaaggatgg gcaactgtac      780
ctgactggag gagtctggag tctagacggc tcagatagca tacaagagac catgcaggct      840
accatccatg tccctgccca gcatgaagat ggccctgagg atgacccaca gttggtaggc      900
atcactgctc gtaacattcc acgagggccc cagttggctg cccagaactt gggcatcagc      960
ctggccaact tgttgctgag caaaggagcc aaaaacatcc tggatgttgc acggcaatta     1020
acgatgccca ttaa                                                       1034

<210> SEQ ID NO 8
<211> LENGTH: 1035
<212> TYPE: DNA
<213> ORGANISM: Homo sapiens

<400> SEQUENCE: 8
atgagagtga ttcgcgtggg tacccgcaag agccagcttg ctcgcataca gacggacagt       60
gtggtggcaa cattgaaagc ctcgtaccct ggcctgcagt ttgaaatcat tgctatgtcc      120
```

-continued

| | |
|---|---|
| accacagggg acaagattct tgatactgca ctctctaaga ttggagagaa aagcctgttt | 180 |
| accaaggagc ttgaacatgc cctggagaag aatgaagtgg acctggttgt tcactccttg | 240 |
| aaggacctgc ccactgtgct tcctcctggc ttcaccatcg agccatctg caagcgggaa | 300 |
| aaccctcatg atgctgttgt ctttcaccca aaatttgttg ggaagaccct agaaaccctg | 360 |
| ccagagaaga gtgtggtggg aaccagctcc ctgcgaagag cagcccagct gcagagaaag | 420 |
| ttcccgcatc tggagttcag gagtattcgg ggaaacctca cacccggct tcggaagctg | 480 |
| gacgagcagc aggagttcag tgccatcatc ctggcaacag ctggcctgca gcgcatgggc | 540 |
| tggcacaacc gggtggggca gatcctgcac cctgaggaat gcatgtatgc tgtgggccag | 600 |
| ggggccttgg gcgtggaagt gcgagccaag gaccaggaca tcttggatct ggtgggtgtg | 660 |
| ctgcacgatc ccgagactct gcttcgctgc atcgctgaaa gggccttcct gaggcacctg | 720 |
| gaaggaggct gcagtgtgcc agtagccgtg catacagcta tgaaggatgg gcaactgtac | 780 |
| ctgactggag gagtctggag tctagacggc tcagatagca tacaagagac catgcaggcc | 840 |
| accatccatg tccctaccca gcatgaagat ggccctgagg atgacccaca gttggtaggc | 900 |
| atcactgctc gtaacattcc acgagggccc cagttggctg cccagaactt gggcatcagc | 960 |
| ctggccaact tgttgctgag caaaggagcc aaaaacatcc tggatgttgc acggcaattg | 1020 |
| aacgatgccc attaa | 1035 |

<210> SEQ ID NO 9
<211> LENGTH: 1260
<212> TYPE: DNA
<213> ORGANISM: Homo sapiens

<400> SEQUENCE: 9

| | |
|---|---|
| cacaggaaac agctatgacc atgattacgc caagctcgaa attaaccctc actaaggga | 60 |
| acaaaagctg gagctccacc gcggtggcgg ccgctctaga actagtggat ccccgggct | 120 |
| gcaggaattc atgagagtga ttcgcgtggg tacccgcaag agccagcttg ctcgcataca | 180 |
| gacggacagt gtggtggcaa cattgaaagc ctcgtaccct ggcctgcagt ttgaaatcat | 240 |
| tgctatgtcc accacagggg acaagattct tgatactgca ctctctaaga ttggagagaa | 300 |
| aagcctgttt accaaggagc ttgaacatgc cctggagaag aatgaagtgg acctggttgt | 360 |
| tcactccttg aaggacctgc ccactgtgct tcctcctggc ttcaccatcg agccatctg | 420 |
| caagcgggaa aaccctcatg atgctgttgt ctttcaccca aaatttgttg ggaagaccct | 480 |
| agaaaccctg ccagagaaga gtgtggtggg aaccagctcc ctgcgaagag cagcccagct | 540 |
| gcagagaaag ttcccgcatc tggagttcag gagtattcgg ggaaacctca cacccggct | 600 |
| tcggaagctg gacgagcagc aggagttcag tgccatcatc ctggcaacag ctggcctgca | 660 |
| gcgcatgggc tggcacaacc gggttgggca gatcctgcac cctgaggaat gcatgtatgc | 720 |
| tgtgggccag ggggccttgg gcgtggaagt gcgagccaag gaccaggaca tcttggatct | 780 |
| ggtgggtgtg ctgcacgatc ccgagactct gcttcgctgc atcgctgaaa gggccttcct | 840 |
| gaggcacctg gaaggaggct gcagtgtgcc agtagccgtg catacagcta tgaaggatgg | 900 |
| gcaactgtac ctgactggag gagtctggag tctagacggc tcagatagca tacaagagac | 960 |
| catgcaggct accatccatg tccctgccca gcatgaagat ggccctgagg atgacccaca | 1020 |
| gttggtaggc atcactgctc gtaacattcc acgagggccc cagttggctg cccagaactt | 1080 |
| gggcatcagc ctggccaact tgttgctgag caaaggagcc aaaaacatcc tggatgttgc | 1140 |
| acggcaattg aacgatgccc attaataagc ttatcgatac cgtcgacctc gaggggggc | 1200 |

```
ccggtaccca attcgccta tagtgagtcg tattacaatt cactggccgt cgttttacaa    1260
```

<210> SEQ ID NO 10
<211> LENGTH: 1113
<212> TYPE: DNA
<213> ORGANISM: Homo sapiens

<400> SEQUENCE: 10

```
cacacagcct actttccaag cggagccatg tctggtaacg gcaatgcggc tgcaacggcg     60
gaagaaaaca gcccaaagat gagagtgatt cgcgtgggta cccgcaagag ccagcttgct    120
cgcatacaga cggacagtgt ggtggcaaca ttgaaagcct cgtaccctgg cctgcagttt    180
gaaatcattg ctatgtccac cacaggggac aagattcttg atactgcact ctctaagatt    240
ggagagaaaa gcctgtttac caaggagctt gaacatgccc tggagaagaa tgaagtggac    300
ctggttgttc actccttgaa ggacctgccc actgtgcttc ctcctggctt caccatcgga    360
gccatctgca gcgggaaaa  ccctcatgat gctgttgtct ttcacccaaa atttgttggg    420
aagaccctag aaaccctgcc agagaagagt gtggtgggaa ccagctccct gcgaagagca    480
gcccagctgc agagaaagtt cccgcatctg gagttcagga gtattcgggg aaacctcaac    540
acccggcttc ggaagctgga cgagcagcag gagttcagtg ccatcatcct ggcaacagct    600
ggcctgcagc gcatgggctg gcacaaccgg gttgggcaga tcctgcaccc tgaggaatgc    660
atgtatgctg tgggccaggg ggccttgggc gtggaagtgc gagccaagga ccaggacatc    720
ttggatctgg tgggtgtgct gcacgatccc gagactctgc ttcgctgcat cgctgaaagg    780
gccttcctga ggcacctgga aggaggctgc agtgtgccag tagccgtgca tacagctatg    840
aaggatgggc aactgtacct gactggagga gtctggagtc tagacggctc agatagcata    900
caagagacca tgcaggctac catccatgtc cctgcccagc atgaagatgg ccctgaggat    960
gacccacagt tggtaggcat cactgctcgt aacattccac gagggcccca gttggctgcc   1020
cagaacttgg gcatcagcct ggccaacttg ttgctgagca aggagccaa  aaacatcctg   1080 gatgttgcac ggcaattgaa cgatgcccat taa                                1113
```

<210> SEQ ID NO 11
<211> LENGTH: 1380
<212> TYPE: DNA
<213> ORGANISM: Homo sapiens

<400> SEQUENCE: 11

```
agcaggtcct actatcgcct ccctctagtc tctgcttctt tggatccctg aggagggcag     60
aaggaagaaa acagcccaaa gatgagagtg attcgcgtgg gtacccgcaa gagccagctt    120
gctcgcatac agacggacag tgtggtggca acattgaaag cctcgtaccc tggcctgcag    180
tttgaaatca ttgctatgtc caccacaggg gacaagattc ttgatactgc actctctaag    240
attggagaga aaagcctgtt taccaaggag cttgaacatg ccctggagaa gaatgaagtg    300
gacctggttg ttcactcctt gaaggacctg cccactgtgc ttcctcctgg cttcaccatc    360
ggagccatct gcaagcggga aaaccctcat gatgctgttg tctttcaccc aaaatttgtt    420
gggaagaccc tagaaaccct gccagagaag agtgtggtgg aaccagctcc ctgcgaaga    480 gcagcccagc tgcagagaaa gttcccgcat ctggagttca ggagtattcg gggaaacctc    540
aacacccggc ttcggaagct ggacgagcag caggagttca gtgccatcat cctagcaaca    600
gctggcctgc agcgcatggg ctggcacaac cgggttgggc agatcctgca ccctgaggaa    660
```

```
tgcatgtatg ctgtgggcca gggggccttg ggcgtggaag tgcgagccaa ggaccaggac      720
atcttggatc tggtgggtgt gctgcacgat cccgagactc tgcttcgctg catcgctgaa      780
agggccttcc tgaggcacct ggaaggaggc tgcagtgtgc cagtagccgt gcatacagct      840
atgaaggatg gcaactgta cctgactgga ggagtctgga gtctagacgg ctcagatagc       900
atacaagaga ccatgcaggc taccatccat gtccctgccc agcatgaaga tggccctgag      960
gatgacccac agttggtagg catcactgct cgtaacattc cacgagggcc ccagttggct      1020
gcccagaact tgggcatcag cctggccaac ttgttgctga gcaaaggagc caaaaccatc      1080
ctggatgttg cacggcagct taacgatgcc cattaactgg tttgtggggc acagatgcct      1140
gggttgctgc tgtccagtgc ctacatcccg ggcctcagtg ccccattctc actgctatct      1200
ggggagtgat tacccgggga gactgaactg cagggttcaa gccttccagg gatttgcctc      1260
accttggggc cttgatgact gccttgcctc ctcagtatgt gggggcttca tctctttaga      1320
gaagtccaag caacagcctt tgaatgtaac caatcctact aataaaccag ttctgaaggt      1380

<210> SEQ ID NO 12
<211> LENGTH: 1377
<212> TYPE: DNA
<213> ORGANISM: Homo sapiens

<400> SEQUENCE: 12
cacacagcct actttccaag cggagccatg tctggtaacg gcaatgcggc tgcaacggcg       60
gaagaaaaca gcccaaagat gagagtgatt cgcgtgggta cccgcaagag ccagcttgct      120
cgcatacaga cggacagtgt ggtggcaaca ttgaaagcct cgtaccctgg cctgcagttt      180
gaaatcattg ctatgtccac cacagggac aagattcttg atactgcact ctctaagatt       240
ggagagaaaa gcctgtttac caaggagctt gaacatgccc tggagaagaa tgaagtggac      300
ctggttgttc actccttgaa ggacctgccc actgtgcttc ctcctggctt caccatcgga      360
gccatctgca gcgggaaaa ccctcatgat gctgttgtct tcacccaaa atttgttggg        420 aagaccctag aaaccctgcc agagaagagt gtggtgggaa ccagctccct gcgaagagca      480
gcccagctgc agagaaagtt cccgcatctg gagttcagga gtattcgggg aaacctcaac      540
acccggcttc ggaagctgga cgagcagcag gagttcagtg ccatcatcct agcaacagct      600
ggcctgcagc gcatgggctg gcacaaccgg gtggggcaga tcctgcaccc tgagaaatgc      660
atgtatgctg tgggccaggg ggccttgggc gtggaagtgc gagccaagga ccaggacatc      720
ttggatctgg tgggtgtgct gcacgatccc gagactctgc ttcgctgcat cgctgaaagg      780
gccttcctga ggcacctgga aggaggctgc agtgtgccag tagccgtgca tacagctatg      840
aaggatggga actgtacct gactggagga gtctggagtc tagacggctc agatagcata      900
caagagacca tgcaggctac catccatgtc cctgcccagc atgaagatgg ccctgaggat      960
gacccacagt tggtaggcat cactgctcgt aacattccac gagggcccca gttggctgcc      1020
cagaacttgg gcatcagcct ggccaacttg ttgctgagca aggagccaa aaacatcctg      1080 gatgttgcac ggcagcttaa cgatgcccat taactggttt gtggggcaca gatgcctggg      1140
ttgctgctgt ccagtgccta catcccgggc tcagtgccc cattctcact gctatctggg      1200
gagtgattac cccgggagac tgaactgcag ggttcaagcc ttcagggat ttgcctcacc      1260 ttggggcctt gatgactgcc ttgcctcctc agtatgtggg ggcttcatct ctttagagaa      1320
gtccaagcaa cagcctttga atgtaaccaa tcctactaat aaaccagttc tgaaggt       1377
```

-continued

```
<210> SEQ ID NO 13
<211> LENGTH: 10024
<212> TYPE: DNA
<213> ORGANISM: Homo sapiens

<400> SEQUENCE: 13
aatcatgatt gttaattatg ttcatgatta caggcgcggt ggctcacgcc tgtactccca      60
gcactttggg aggccgaggt gggcgaatca cctgaggtca ggagttcaag acctgcctga     120
ctaacatgga gaaacctcat ctctaccaaa aatacaaaat tagccgggtg tggtggtgcg     180
tgcctgtaat cccagctact cgggggggctg aggcaggaga attgcttgaa cccgggaggc    240
ggaggttgca gtgagctgag atcgtgccat tgcattccag cctgggcaac aagagcgaaa    300
ctccgtctca aaaaaaaaaa aaaattatgt tcatgggaaa gcacttttcc taacaagccc    360
ttttctcact acatgtaggt ttgtgctccc acttcagtta cttgtcttta ggcatgacct    420
ttaatctctc tgaaccagtt tcctcatttt aagaattgaa atgctggctg gccagtcgt     480 cacgcctgta atcccagcac tttgggaggc caaggcgaga tgactgcttg agtccaggag    540
ttcgagacta gcctgggcaa catagtgagg ccacctcccc gctgtctcta taaaaaatc    600 tagaaattag tcccacgtgg tgatgtgcgc ctgtagtccc agctgcttgg gaggctgagg    660 tgggggatc gctgaagccg ggaggtcaag gctgcagtga cccgtggtca tgccgctgca    720
ctctagtctg gggacacagt gagacccgt atcaaaaga aaaatgctgc ctatttcaag      780
gttgtagcaa agctaagttt gaacagagca aaggaagcgc catagaagct gcactacttg    840
ctcatgtcac agctgggaa tggggaggtc gaatggggag gtccactgtc gcaatgttcc     900
aattcccgcc cagagggagg gacctcccct tcgagggagg gcgccggaag tgacgcgagg    960
ctctgcggag accaggagtc agactgtagg acgacctcgg gtcccacgtg tccccggtac   1020
tcgccggccg gagcctccgg cttcccgggg ccggggggacc ttagcggcac ccacacacag   1080
cctactttcc aagcggagcc atgtctggta acggcaatgc ggctgcaacg gcggtgagtg   1140
ctgagccggt gaccagcaca ctttgggctt ctggacgagc cgtgcagcga ttggccccag   1200
gttgccatcc tcagtcgtct attggtcaga acggctatct ttttttttt tttttttt     1260 tttttggtcc gagtagcttt taaagggcca gtagctcggt tgccctccgg aaggaatggg   1320
gaaatcagag agcggtgata ctgggttaag agtggaagga ttgtttggaa cggaactccg   1380
gtccctgcgg gcatctgggt gggattccca tcaggcctgg gatgcacggc tctagattta    1440
gtgacccaga ccaagaacgt tcgtctacac agacggggtc ctttcattcg aggctgggct   1500
gaggcggatg cagatacggc ccctttggga agacacgttc cacttttgat tcataggaga    1560
gagtatcagc caagcctccg aactgcacac aaacgtctta gaagtgcgcc ttctttttgt    1620
gttatagtgg tctcccagcc acagccaacg ctccaagtcc ccagctgtga cacacctact   1680
gaattactac cgtgggtggg aggccgccgt gggcctttcc attacgagcc tgcttgccga   1740
gccctgggct tgtgcacaga caaactgcag agctggtgga ggccactgcc aggccgagat   1800
aagaaagaga tggggagctg ctaatctccc cctgtccagc ctgttggtga gggctgggat   1860
ctttgctctt gcagtcattc cagagccctg gactaggagt aggaagatct gaattgtggc   1920
cccaactctc tttcggttat tagctctgtg acccctaggca agtcacctca tcccttgatg   1980
ccacccgttg cttctgtaac atggtcccaa aggtgcctgt cttgtccacc tgataggatt   2040
tttgagacga caacaatatg caaaagcaat agcttcaaca tagaagtgct cagtgtttta   2100 tttttttaatg aaacggtttg acttggatat gctgtgcaca ttcaatgaac ttaaggaatt   2160
```

```
gtttgaacct agtagttctg ggaccttaga gtcctttctg tgggctccct gtggcccaga    2220 ttttggtgg ccacgtttaa tatcaagcct agcctaattt gcaaagggtc tcccagggtt     2280
aatttattgg agtgatcaca tggagtagac cagagtctga gggcagaaag ctgtcacctg    2340
cttcggcaat agaggcccca gatgtctggg tgcaaaagaa ctccatagca ccccgaccaa    2400
catggtgaaa ccccgtctct actaaaaata taaaaattag ccgagcaca gtggctcatg     2460 cctgtaatcc tagcactttg ggaggccgag gcaggtggat tgcctgagct caggagttcg    2520
agaccagcct agggaacaca gtgaaacccc gtttctacta aaatacaaa aaattagccg     2580 acgtggtggc atgcgcctgc agtcccagct acttgggagg ctaagacagg agaatcgctt    2640
gaacctggga ggtggaggtt gcactgagcc gagaccgcgc cattgcactc cagcctgggt    2700
gacagagcgc aactccccct caaaaaaaga aaaaaatata tatatatata tatatatata    2760
tacacacata ttttagctgg gcatggtggt gtgcgtctgt agtagtccca gctacttggg    2820
aggctgagtc aggagaatcg cttgaacctg gaaggcagtg gttgtagtta gctgagaaca    2880
tgccactgca ctccagcctg gcaacgagag ggagactctg tctcaaaaaa aaaaaaaaaa    2940
aggaactaca taggatgaac atcccagatc agggaatgtt gactgtcgac agtatcagta    3000
tctacagtgg ctactgtctg atgtagaaag aaatgggatc aggctaggcg tggtggctca    3060
cgcctgtaat cccagctctt tgggaggctg ggcaggagg atcacaagtt cgagaccagc     3120
ctggccaaca cagtgaaacc ccgtctctac taaaaatgtg aaaattagct gggcatggtg    3180
gaacatgctg tagttccagc ttgaacccag gggtggaggt tgtagtgagc ctagatcacg    3240
ccactgcact ccagcctgag caaaacagtg agactctgtc taaaaaaaa aaaaaaaaa      3300 agagaaatgg gacctccgtc ttagactgaa gaattcagtt ctacgtgctt agcagtgaat    3360
acttttgtcc aaggtactct ggcaggagga agaggcgtgt cctcttgagt tcttgacttg    3420
ggctctggcc tgttaatatt tccatgttgg tgaaaccaga ggcagcactc taggtgaacg    3480
aactttaggc agcgcagcct cctagtctta tggaacatct gaggcagaag aaacctgagt    3540 ccaaccttt catttatag atgaacaaac agatcctgat gggacagtgt acccaaggtc      3600
acccagccaa gaggctgagc aggactgtac gtcagatccg tttacctcag tccttaatgc    3660
atgcagtcca gccagattaa gggacccctta atactgtcag cttttcccac tgtgggatct   3720
tcatcctctt gacttctttt gtagccagac atctgggcct cttgctggag aaggtggcag    3780
cttgctgctc ttagactcta gtctactcca tgtggcatct ggatggcact gaaattttct    3840
caagtgcctt gtctgttgta gataatgaat ctatcctcca gtgactcagc acaggttccc    3900
cagtgtggtc ctggctgccc tgcccctgcc agctgcaggc cccacccttc ctgtggccag    3960
gctgatgggc cttatctctt tacccacctg gctgtgcaca gcactccac tgacaactgc     4020 cttggtcaag gtgggcttca gggctcagtg tcctggttac tgcagcggca gcaacagcag    4080
gtcctactat cgcctccctc tagtctctgc ttctctggat ccctgaggag ggcagaaggt    4140
actgaggaag gttaaaggga ccagccttgg agtatttccc cactctgaga ctcagctggc    4200
cacaggccag gttctgaatt tcctttcttc aagccagtg attctggttc ttggacaagg     4260
tgttgaggaa cactagaaac agaggggact gtgacctggg gactttttct gcaggaagaa    4320
aacagcccaa agatgagagt gattcgcgtg gtacccgca agagccaggt gggtgcagga     4380
gccggggtgg aggaggtttg tcagaacagt tatgatgctc acagcatcac aaattggggg   4440
actcagaggg ttagttccta gtatgaagga gatggggtgg ctgggcgtta agttccccgg    4500
gaaatggcag attacattct atggcaagat catccctagg ctgggaaaat tgttggagtg    4560
```

```
cagagggctc caagcccct  tctcatgccc agatggaaat tccagtccct tcaggatctg    4620
cctaacctgt gacagtctaa agagtctgag ccgtggctgg gaagggcagg actaatccaa    4680
atctctaccc gcagcttgct cgcatacaga cggacagtgt ggtggcaaca ttgaaagcct    4740
cgtaccctgg cctgcagttt gaaatcagtg agttttctgg aaaggagtgg aagctaatgg    4800
gaagcccagt accccgagag gagagaacac aacatttctg gctttgccta tagctaaagc    4860
ccgtcccgct gccccgagat tccttctggg ctgctcccag ttctgaaggt gctttcctct    4920
gaatacctcc agctctgact acctggatta gcctggcatt taacatcttg agctttgggt    4980
ctttttatga gtgtttctgg tcttcctgct cgattgtata tactcagagg gcaggaacca    5040
gggattatgt gcctctgtcc ccatcatgaa tcgtagcaca gtgctaggct cagtaaatgc    5100
tgatcaataa tgagcacctg attgattgac tctctcctca gttgctatgt ccaccacagg    5160
ggacaagatt cttgatactg cactctctaa ggtaacaaca tcttcctccc cagttcttgt    5220
ccccactctt ctttccttcc ctgaagggat tcactcaggc tctttctgtc cggcagattg    5280
gagagaaaag cctgtttacc aaggagcttg aacatgccct ggagaagaat gagtaagtaa    5340
agataggaga gtgtggtgcc ctcccagtct cttgctggga ccctagtatg ctaggtctct    5400
tgctgggacc cggggtgtca gataggctgc tgggcttaaa ccctcagaga ggctgaaggc    5460
agctcatagg tgggttttt caggcttcag aaaaggagag tgtctggttc tgagccatct    5520
ggctgcctgg actgcaagaa tggctggggg agggagggta ggagggagag taggagggag    5580
agtgagagga gagcagtttt catgctcctg agatcttgag aaggtgtgct tcctgaactg    5640
ccctaggctc caccactgaa gtagaggcag gggtgggtgg agaagggtg aaggctggct    5700 gctcataccc tttctctttg ccccctctc ccatctctat agagtggacc tggttgttca    5760
ctccttgaag gacctgccca ctgtgcttcc tcctggcttc accatcggag ccatctgcaa    5820
gtaagagtct tgcaagtaag gggcttgggc aggggtaggc atcatgtgaa cctttgcctt    5880
tccctttggg gcctgaccct ctgcttcagg gttatctcct ctgccctgag gagtgttgac    5940
tggtggcaga aaactcaaga aataccagtg agttggcaat cgagagagaa tagaggtgat    6000
ctgaacttaa atctcttccc tcattctgtg cccttccctc ctcccccagg cgggaaaacc    6060
ctcatgatgc tgttgtcttt cacccaaaat ttgttgggaa gaccctagaa accctgccag    6120
agaagaggta agtggggcct ggataggcag cttggtggga tgtgcccaga agatgcaggg    6180
atgggaggag gaggaaagga acagtgactg cctagtgtta aaatctcatt gtaacttctc    6240
tctgggcagt gtggtgggaa ccagctccct gcgaagagca gcccagctgc agagaaagtt    6300
cccgcatctg gagttcagga gtattgtatc cttttagaag agtgacggat ccttttggaa    6360
gagtgacgga gacagcagcc aaggaaaaag acaaggtcta gagggctctg ggagtccgga    6420
gagtggaagg ggcttccagc aagcagcccg tggggtcagt ggcctgtctg tctttccatg    6480
cactcatccg tccactcatt tacagtctaa tgttttctta gccccagaca agtgttcaga    6540
gtgcaaggca ttgggggataa tggtgagcaa gataaacatt cccctgcata tgtagagttt    6600
acgtcttact tagggataat gcagttatac tgaactgaat agtgactact tctggaggga    6660
tagggagtac ttccttttt tttttttttt tttctgagac ggagtctcgc tctgttgccc    6720
aggttggagt gcagtggcgc aatctaggct cactgcaact tctgcctcct gagttcaagc    6780
aatcttcctg cctcagcctc ctaagtagtt gggattacag gtgccaccac acctggctaa    6840 ttttttgtatt tttagtagag actgggtttc accatgttag tcaggctggt ctcaaactcc    6900
```

| | | | | |
|---|---|---|---|---|
| tgacctcagg | tgatccacca | gcctcggcct | cccaagggc | tgggattaca ggcttgagcc | 6960 |
| ccgcacccgg | tcagtacttc | cattttata | tgctactata | ttgtcttgac ttttacaatg | 7020 |
| aatatgtagt | acatttcata | aaactaaatt | taaaaatagt | atgtgctaag tgctccaata | 7080 |
| agtgaagttg | ggaattttct | ggaaacttct | agttggaaca | tctaaacaca gaagtctggg | 7140 |
| gtgtcaggga | aggttctca | gaggtcttgt | aaccttggca | agttatttag cctccctatg | 7200 |
| tcattttcct | tatctgtaaa | gtggggataa | taatactacc | ttcctcacag ggttgttgtg | 7260 |
| aagatgaaat | gagctgacat | atggaaagta | cttttagagc | agtgtctggc atgtagtaag | 7320 |
| tatgatgtaa | ctgttagctg | ttaacattaa | gctgagagct | ggaagatgac tgaaagtcag | 7380 |
| ccagctagag | agggaaagac | agactcaggc | agagggaacc | gcacgaggcc ccagattgcc | 7440 |
| cgacactgtg | gtccttagca | actctccaca | gcggggaaac | ctcaacaccc ggcttcggaa | 7500 |
| gatggacgag | cagcaggagt | tcagtgccat | catcctggca | acagctggcc tgcagcgcat | 7560 |
| gggctggcac | aaccgggttg | ggcaggtagg | gcctgcccct | atcctctccc cagctcatct | 7620 |
| gcatctcctt | tctgccttac | agtcatcccc | aatttaggat | ttttagactt tatgattgtg | 7680 |
| tgaaagcgat | atacgttcag | tagaaactgt | acttagtacc | catacagcca ttctgttttt | 7740 |
| tactttcagt | acagtattca | ttacatgaga | tattcacttt | attgtaaaac aggcttggtg | 7800 |
| tcagatgatt | ttgtccaact | ataataggct | aatcttaagt | gttctgagca catgtaaggt | 7860 |
| aggctaggtg | tattaaatgc | attttcagct | tgttttcaac | ttaacaatgg gtttatcagg | 7920 |
| atgtaaccct | attgtaagtc | aaggaccatc | tgtcttcact | tcttgaccac cccacctcta | 7980 |
| acaccgtagg | ctgggaagat | tgtgaatcag | aggccagact | ctaggctttc atggagaaaa | 8040 |
| tttacaaaaa | aaaaaaaag | aggccagact | cacacttagg | cctacccagg ctttctagat | 8100 |
| gatagggaac | tccatctcca | ctgccagtg | cttttagaca | ccccgtgtc caccttttg | 8160 |
| actccctgtt | ccgcctccac | agatcctgca | ccctgaggaa | tgcatgtatg ctgtgggcca | 8220 |
| ggtacacttg | accagggaag | ccacatggtg | acatatgcct | tccctttgtt ctcaaccaag | 8280 |
| aagcttgtct | cacaaccttc | tgcatctgct | tccccagaat | agcattctca gggaggggca | 8340 |
| gaccttggga | tgctaccggt | ccaaaaggcg | ctggggagca | agtagataga ggtggtccca | 8400 |
| tgctttgcgc | cattggttgg | ggaaagatca | ggcctgatgt | cctaggatgt ttttccatca | 8460 |
| gggggccttg | ggcgtggaag | tgcgagccaa | ggaccaggac | atcttggatc tggtgggtgt | 8520 |
| gctgcacgat | cccgagactc | tgcttcgctg | catcgctgaa | agggccttcc tgaggcacct | 8580 |
| ggtagggcct | gtgctccacc | tgtggagggc | tggggacttg | gagagctggg aaaggtggca | 8640 |
| gggaagattt | cttacatgaa | tgctctgtat | acagtgctaa | ctcattcttg ttgaatgttg | 8700 |
| tgtatggata | ggaccaggtc | tgggcccaca | gttgcctttt | cagtgatgtc ctcaggtctg | 8760 |
| tggtcacagg | gtggtgttaa | gagcccttgc | agctcacaag | aacttcttgt tacaggaagg | 8820 |
| aggctgcagt | gtgccagtag | ccgtgcatac | agctatgaag | gatgggcaag taagtggggg | 8880 |
| gaaatgggcg | ggaagccagg | gaaaggagga | ctgtggcatt | tcttcctgtg catcccaggt | 8940 |
| ttctaggtag | tcccctctca | gactgtgctg | aggcaactgt | tttcttcccc agctgtacct | 9000 |
| gactggagga | gtctggagtc | tagacggctc | agatagcata | caagagacca tgcaggctac | 9060 |
| catccatgtc | cctgcccagg | taccaaagct | ggagggcgag | ggggtaataa acaagagtgc | 9120 |
| atataatctc | ttgttctcac | caaatcccac | ctccttccct | catacagcat gaagatggcc | 9180 |
| ctgaggatga | cccacagttg | gtaggcatca | ctgctcgtaa | cattccacga gggccccagt | 9240 |
| tggctgccca | gaacttgggc | atcagcctgg | ccaacttgtt | gctgagcaaa ggagccaaaa | 9300 |

```
acatcctgga tgttgcacgg cagcttaacg atgcccatta actggtttgt ggggcacaga    9360
tgcctgggtt gctgctgtcc agtgcctaca tcccgggcct cagtgcccca ttctcactgc    9420
tatctgggga gtgattaccc cgggagactg aactgcaggg ttcaagcctt ccagggattt    9480
gcctcacctt ggggccttga tgactgcctt gcctcctcag tatgtggggg cttcatctct    9540
ttagagaagt ccaagcaaca gcctttgaat gtaaccaatc ctactaataa accagttctg    9600
aaggtgttgt gtgtgcgcgt gtggagttgg cgggaagata ggaacaaaca caaagccctt    9660
tcatccttac ctcagaggct gggacttttg cccagagttc tcctggtacg tcctttctgc    9720
ttctgcctca atagttttca tttcacacag aataaattgt ctcccaggaa caccaagaaa    9780
cagagccaca atcttaaatt cctatggttt gccccttcag ttaacagtag agcctgttta    9840
tattgcatgg cccctcccac ccctattatc aggaaagtat agaaagtcac taattctaca    9900
actctcttgc aaaatgaaaa caaatgctcc atttaaaaaa aaaacaatcc tttaataaaa    9960
ttagtccatc taaaactccc caatgcctaa ggttctagtc gtggaagggt tagctgcaga    10020
attc                                                                 10024
```

<210> SEQ ID NO 14
<211> LENGTH: 361
<212> TYPE: PRT
<213> ORGANISM: Homo sapiens

<400> SEQUENCE: 14

```
Met Ser Gly Asn Gly Asn Ala Ala Ala Thr Ala Glu Glu Asn Ser Pro
1               5                   10                  15

Lys Met Arg Val Ile Arg Val Gly Thr Arg Lys Ser Gln Leu Ala Arg
            20                  25                  30

Ile Gln Thr Asp Ser Val Val Ala Thr Leu Lys Ala Ser Tyr Pro Gly
        35                  40                  45

Leu Gln Phe Glu Ile Ile Ala Met Ser Thr Thr Gly Asp Lys Ile Leu
    50                  55                  60

Asp Thr Ala Leu Ser Lys Ile Gly Glu Lys Ser Leu Phe Thr Lys Glu
65                  70                  75                  80

Leu Glu His Ala Leu Glu Lys Asn Glu Val Asp Leu Val Val His Ser
                85                  90                  95

Leu Lys Asp Leu Pro Thr Val Leu Pro Pro Gly Phe Thr Ile Gly Ala
            100                 105                 110

Ile Cys Lys Arg Glu Asn Pro His Asp Ala Val Val Phe His Pro Lys
        115                 120                 125

Phe Val Gly Lys Thr Leu Glu Thr Leu Pro Glu Lys Ser Val Val Gly
    130                 135                 140

Thr Ser Ser Leu Arg Arg Ala Ala Gln Leu Gln Arg Lys Phe Pro His
145                 150                 155                 160

Leu Glu Phe Arg Ser Ile Arg Gly Asn Leu Asn Thr Arg Leu Arg Lys
                165                 170                 175

Met Asp Glu Gln Gln Glu Phe Ser Ala Ile Ile Leu Ala Thr Ala Gly
            180                 185                 190

Leu Gln Arg Met Gly Trp His Asn Arg Val Gly Gln Ile Leu His Pro
        195                 200                 205

Glu Glu Cys Met Tyr Ala Val Gly Gln Gly Ala Leu Gly Val Glu Val
    210                 215                 220

Arg Ala Lys Asp Gln Asp Ile Leu Asp Leu Val Gly Val Leu His Asp
225                 230                 235                 240
```

```
Pro Glu Thr Leu Leu Arg Cys Ile Ala Glu Arg Ala Phe Leu Arg His
            245                 250                 255

Leu Glu Gly Gly Cys Ser Val Pro Val Ala Val His Thr Ala Met Lys
        260                 265                 270

Asp Gly Gln Leu Tyr Leu Thr Gly Gly Val Trp Ser Leu Asp Gly Ser
        275                 280                 285

Asp Ser Ile Gln Glu Thr Met Gln Ala Thr Ile His Val Pro Ala Gln
        290                 295                 300

His Glu Asp Gly Pro Glu Asp Pro Gln Leu Val Gly Ile Thr Ala
305                 310                 315                 320

Arg Asn Ile Pro Arg Gly Pro Gln Leu Ala Ala Gln Asn Leu Gly Ile
                325                 330                 335

Ser Leu Ala Asn Leu Leu Ser Lys Gly Ala Lys Asn Ile Leu Asp
            340                 345                 350

Val Ala Arg Gln Leu Asn Asp Ala His
            355                 360

<210> SEQ ID NO 15
<211> LENGTH: 344
<212> TYPE: PRT
<213> ORGANISM: Homo sapiens

<400> SEQUENCE: 15

Met Arg Val Ile Arg Val Gly Thr Arg Lys Ser Gln Leu Ala Arg Ile
1               5                   10                  15

Gln Thr Asp Ser Val Val Ala Thr Leu Lys Ala Ser Tyr Pro Gly Leu
            20                  25                  30

Gln Phe Glu Ile Ile Ala Met Ser Thr Thr Gly Asp Lys Ile Leu Asp
        35                  40                  45

Thr Ala Leu Ser Lys Ile Gly Glu Lys Ser Leu Phe Thr Lys Glu Leu
50                  55                  60

Glu His Ala Leu Glu Lys Asn Glu Val Asp Leu Val Val His Ser Leu
65                  70                  75                  80

Lys Asp Leu Pro Thr Val Leu Pro Pro Gly Phe Thr Ile Gly Ala Ile
                85                  90                  95

Cys Lys Arg Glu Asn Pro His Asp Ala Val Val Phe His Pro Lys Phe
            100                 105                 110

Val Gly Lys Thr Leu Glu Thr Leu Pro Glu Lys Ser Val Val Gly Thr
        115                 120                 125

Ser Ser Leu Arg Arg Ala Ala Gln Leu Gln Arg Lys Phe Pro His Leu
        130                 135                 140

Glu Phe Arg Ser Ile Arg Gly Asn Leu Asn Thr Arg Leu Arg Lys Met
145                 150                 155                 160

Asp Glu Gln Gln Glu Phe Ser Ala Ile Ile Leu Ala Thr Ala Gly Leu
                165                 170                 175

Gln Arg Met Gly Trp His Asn Arg Val Gly Gln Ile Leu His Pro Glu
            180                 185                 190

Glu Cys Met Tyr Ala Val Gly Gln Gly Ala Leu Gly Val Glu Val Arg
        195                 200                 205

Ala Lys Asp Gln Asp Ile Leu Asp Leu Val Gly Val Leu His Asp Pro
    210                 215                 220

Glu Thr Leu Leu Arg Cys Ile Ala Glu Arg Ala Phe Leu Arg His Leu
225                 230                 235                 240

Glu Gly Gly Cys Ser Val Pro Val Ala Val His Thr Ala Met Lys Asp
```

```
                  245                 250                 255
Gly Gln Leu Tyr Leu Thr Gly Gly Val Trp Ser Leu Asp Gly Ser Asp
            260                 265                 270

Ser Ile Gln Glu Thr Met Gln Ala Thr Ile His Val Pro Ala Gln His
        275                 280                 285

Glu Asp Gly Pro Glu Asp Pro Gln Leu Val Gly Ile Thr Ala Arg
    290                 295                 300

Asn Ile Pro Arg Gly Pro Gln Leu Ala Ala Gln Asn Leu Gly Ile Ser
305                 310                 315                 320

Leu Ala Asn Leu Leu Ser Lys Gly Ala Lys Asn Ile Leu Asp Val
                325                 330                 335

Ala Arg Gln Leu Asn Asp Ala His
                340

<210> SEQ ID NO 16
<211> LENGTH: 2022
<212> TYPE: DNA
<213> ORGANISM: Homo sapiens

<400> SEQUENCE: 16
ccggtaccgg ctcctcctgg gctccctcta gcgccttccc cccggcccga ctgcctggtc      60
agcgccaagt gacttacgcc cccgaccctg agcccggacc gctaggcgag gaggatcaga     120
tctccgctcg agaatctgaa ggtgcccctgg tcctggagga gttccgtccc agccctgcgg    180 tctccggta ctgctcgccc cggccctctg agcttcagg aggcggccgt cagggtcggg       240
gagtatttgg gtccggggtc tcagggaagg gcggcgcctg ggtctgcggt atcggaaaga    300
gcctgctgga gccaagtagc cctccctctc ttgggacaga cccctcggtc ccatgtccat    360
gggggcaccg cggtccctcc tcctggccct ggctgctggc ctggccgttg ccgtccgcc    420 caacatcgtg ctgatctttg ccgacgacct cggctatggg gacctgggct gctatgggca    480
ccccagctct accactccca acctggacca gctggcggcg ggagggctgc ggttcacaga   540
cttctacgtg cctgtgtctc tgtgcacacc tctagggcc gccctcctga ccggccggct    600
cccggttcgg atgggcatgt accctggcgt cctggtgccc agctcccggg ggggcctgcc    660
cctggaggag gtgaccgtgg ccgaagtcct ggctgcccga ggctacctca caggaatggc    720
cggcaagtgg caccttgggg tggggcctga ggggcctttc ctgccccccc atcagggctt    780
ccatcgattt ctaggcatcc cgtactccca cgaccagggc cctgccaga acctgacctg    840 cttcccgccg ccactccttc gcgacggtgg ctgtgaccag gcctggtcc catcccact    900 gttggccaac ctgtccgtgg aggcgcagcc ccctggctg cccggactag aggcccgcta    960
catggctttc gccatgacc tcatggccga cgcccagcgc caggatcgcc ccttcttcct    1020
gtactatgcc tctcaccaca cccactaccc tcagttcagt gggcagagct ttgcagagcg   1080
ttcaggccgc gggccattg gggactccct gatggagctg gatgcagctg tggggaccct   1140
gatgacagcc atagggggac ctggggctgct tgaagagacg ctggtcatct tcactgcaga   1200
caatggacct gagaccatgc gtatgtcccg aggcggctgc tccggtctct tgcggtgtgg   1260
aaagggaacg acctacgagg gcggtgtccg agagcctgcc ttggccttct ggccaggtca   1320
tatcgctccc ggcgtgaccc acgagctggc cagctccctg gacctgctgc taccctggc    1380 agccctggct ggggccccac tgcccaatgt caccttggat ggctttgacc tcagcccct    1440 gctgctgggc acaggcaaga gccctcggca gtctctcttc ttctaccgt cctacccaga    1500 cgaggtccgt ggggttttg ctgtgcggac tggaaagtac aaggctcact tcttcaccca    1560
```

```
gggctctgcc cacagtgata ccactgcaga ccctgcctgc cacgcctcca gctctctgac    1620
tgctcatgag cccccgctgc tctatgacct gtccaaggac cctggtgaga actacaacct    1680 gctgggggt gtggccgggg ccaccccaga ggtgctgcaa ccctgaaac agcttcagct      1740 gctcaaggcc cagttagacg cagctgtgac cttcggcccc agccaggtgg cccggggcga    1800
ggaccccgcc ctgcagatct gctgtcatcc tggctgcacc cccgcccag cttgctgcca    1860 ttgcccagat ccccatgcct gagggcccct cggctggcct gggcatgtga tggctcctca    1920
ctgggagcct gtggggagg ctcaggtgtc tggaggggt ttgtgcctga taacgtaata     1980
acaccagtgg agacttgcac atctgaaaaa aaaaaaaaaa aa                      2022
```

<210> SEQ ID NO 17  
<211> LENGTH: 1524  
<212> TYPE: DNA  
<213> ORGANISM: Homo sapiens

<400> SEQUENCE: 17

```
atgggggcac cgcggtccct cctcctggcc ctggctgctg gcctggccgt tgcacgtccg     60
cccaacatcg tgctgatctt tgccgacgac ctcggctatg ggacctgggg ctgctatggg    120
caccccagct ctaccactcc caacctggac cagctggcgg cgggagggct gcggttcaca    180
gacttctacg tgcctgtgtc tctgtgcaca ccctctaggg ccgccctcct gaccggccgg    240
ctcccggttc ggatgggcat gtaccctggc gtcctggtgc ccagctcccg ggggggcctg    300
cccctggagg aggtgaccgt ggccgaagtc ctggctgccc gaggctacct cacaggaatg    360
gccggcaagt ggcaccttgg ggtggggcct gagggggcct tcctgccccc ccatcagggc    420
ttccatcgat ttctaggcat cccgtactcc cacgaccagg gccctgcca gaacctgacc     480 tgcttcccgc cggccactcc ttgcgacggt ggctgtgacc agggcctggt ccccatccca    540
ctgttggcca acctgtccgt ggaggcgcag ccccccctggc tgcccggact agaggcccgc    600
tacatggctt tcgcccatga cctcatggcc gacgcccagc gccaggatcg ccccttcttc    660
ctgtactatg cctctcacca cacccactac cctcagttca gtgggcagag ctttgcagag    720
cgttcaggcc gcgggccatt tggggactcc ctgatggagc tggatgcagc tgtggggacc    780
ctgatgacag ccatagggga cctggggctg cttgaagaga cgctggtcat cttcactgca    840
gacaatggac ctgagaccat gcgtatgtcc cgaggcggct gctccggtct cttgcggtgt    900
ggaaagggaa cgacctacga gggcggtgtc cgagagcctg ccttggcctt ctggccaggt    960
catatcgctc ccgcgtgac ccacgagctg gccagctccc tggacctgct gcctaccctg   1020
gcagccctgg ctggggcccc actgcccaat gtcaccttgg atggctttga cctcagcccc   1080
ctgctgctgg gcacaggcaa gagccctcgg cagtctctct tcttctaccc gtcctaccca   1140
gacgaggtcc gtgggtttt tgctgtgcgg actggaaagt acaaggctca cttcttcacc   1200
cagggctctg cccacagtga taccactgca gaccctgcct gccacgcctc cagctctctg   1260
actgctcatg agcccccgct gctctatgac ctgtccaagg accctggtga gaactacaac   1320
ctgctggggg gtgtggccgg ggccacccca gaggtgctgc aagccctgaa acagcttcag   1380
ctgctcaagg cccagttaga cgcagctgtg accttcggcc ccagccaggt ggcccggggc   1440
gaggaccccg ccctgcagat ctgctgtcat cctggctgca ccccccgccc agcttgctgc   1500
cattgcccag atccccatgc ctga                                         1524
```

<210> SEQ ID NO 18

<211> LENGTH: 507
<212> TYPE: PRT
<213> ORGANISM: Homo sapiens

<400> SEQUENCE: 18

```
Met Gly Ala Pro Arg Ser Leu Leu Ala Leu Ala Ala Gly Leu Ala
1               5                   10                  15

Val Ala Arg Pro Pro Asn Ile Val Leu Ile Phe Ala Asp Asp Leu Gly
            20                  25                  30

Tyr Gly Asp Leu Gly Cys Tyr Gly His Pro Ser Ser Thr Thr Pro Asn
                35                  40                  45

Leu Asp Gln Leu Ala Ala Gly Gly Leu Arg Phe Thr Asp Phe Tyr Val
    50                  55                  60

Pro Val Ser Leu Cys Thr Pro Ser Arg Ala Ala Leu Leu Thr Gly Arg
65                  70                  75                  80

Leu Pro Val Arg Met Gly Met Tyr Pro Gly Val Leu Val Pro Ser Ser
                85                  90                  95

Arg Gly Gly Leu Pro Leu Glu Glu Val Thr Val Ala Glu Val Leu Ala
                100                 105                 110

Ala Arg Gly Tyr Leu Thr Gly Met Ala Gly Lys Trp His Leu Gly Val
            115                 120                 125

Gly Pro Glu Gly Ala Phe Leu Pro Pro His Gln Gly Phe His Arg Phe
        130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Gly Cys Asp Gln Gly Leu
                165                 170                 175

Val Pro Ile Pro Leu Leu Ala Asn Leu Ser Val Glu Ala Gln Pro Pro
            180                 185                 190

Trp Leu Pro Gly Leu Glu Ala Arg Tyr Met Ala Phe Ala His Asp Leu
        195                 200                 205

Met Ala Asp Ala Gln Arg Gln Asp Arg Pro Phe Phe Leu Tyr Tyr Ala
    210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
            260                 265                 270

Glu Thr Leu Val Ile Phe Thr Ala Asp Asn Gly Pro Glu Thr Met Arg
        275                 280                 285

Met Ser Arg Gly Gly Cys Ser Gly Leu Leu Arg Cys Gly Lys Gly Thr
    290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335

Leu Pro Thr Leu Ala Ala Leu Ala Gly Ala Pro Leu Pro Asn Val Thr
            340                 345                 350

Leu Asp Gly Phe Asp Leu Ser Pro Leu Leu Leu Gly Thr Gly Lys Ser
        355                 360                 365

Pro Arg Gln Ser Leu Phe Phe Tyr Pro Ser Tyr Pro Asp Glu Val Arg
    370                 375                 380

Gly Val Phe Ala Val Arg Thr Gly Lys Tyr Lys Ala His Phe Phe Thr
```

```
                385                 390                 395                 400
            Gln Gly Ser Ala His Ser Asp Thr Thr Ala Asp Pro Ala Cys His Ala
                            405                 410                 415

Ser Ser Ser Leu Thr Ala His Glu Pro Pro Leu Leu Tyr Asp Leu Ser
                            420                 425                 430

Lys Asp Pro Gly Glu Asn Tyr Asn Leu Leu Gly Val Ala Gly Ala
                            435                 440                 445

Thr Pro Glu Val Leu Gln Ala Leu Lys Gln Leu Gln Leu Leu Lys Ala
            450                 455                 460

Gln Leu Asp Ala Ala Val Thr Phe Gly Pro Ser Gln Val Ala Arg Gly
            465                 470                 475                 480

Glu Asp Pro Ala Leu Gln Ile Cys Cys His Pro Gly Cys Thr Pro Arg
                            485                 490                 495

Pro Ala Cys Cys His Cys Pro Asp Pro His Ala
                            500                 505

<210> SEQ ID NO 19
<211> LENGTH: 489
<212> TYPE: PRT
<213> ORGANISM: Homo sapiens
<220> FEATURE:
<221> NAME/KEY: MOD_RES
<222> LOCATION: (51)..(51)
<223> OTHER INFORMATION: C-alpha Formylglycine

<400> SEQUENCE: 19

Arg Pro Pro Asn Ile Val Leu Ile Phe Ala Asp Asp Leu Gly Tyr Gly
            1               5                   10                  15

Asp Leu Gly Cys Tyr Gly His Pro Ser Ser Thr Thr Pro Asn Leu Asp
                            20                  25                  30

Gln Leu Ala Ala Gly Gly Leu Arg Phe Thr Asp Phe Tyr Val Pro Val
                            35                  40                  45

Ser Leu Xaa Thr Pro Ser Arg Ala Ala Leu Leu Thr Gly Arg Leu Pro
            50                  55                  60

Val Arg Met Gly Met Tyr Pro Gly Val Leu Val Pro Ser Ser Arg Gly
            65                  70                  75                  80

Gly Leu Pro Leu Glu Glu Val Thr Val Ala Glu Val Leu Ala Ala Arg
                            85                  90                  95

Gly Tyr Leu Thr Gly Met Ala Gly Lys Trp His Leu Gly Val Gly Pro
                            100                 105                 110

Glu Gly Ala Phe Leu Pro Pro His Gln Gly Phe His Arg Phe Leu Gly
                            115                 120                 125

Ile Pro Tyr Ser His Asp Gln Gly Pro Cys Gln Asn Leu Thr Cys Phe
            130                 135                 140

Pro Pro Ala Thr Pro Cys Asp Gly Gly Cys Asp Gln Gly Leu Val Pro
            145                 150                 155                 160

Ile Pro Leu Leu Ala Asn Leu Ser Val Glu Ala Gln Pro Pro Trp Leu
                            165                 170                 175

Pro Gly Leu Glu Ala Arg Tyr Met Ala Phe Ala His Asp Leu Met Ala
                            180                 185                 190

Asp Ala Gln Arg Gln Asp Arg Pro Phe Phe Leu Tyr Tyr Ala Ser His
                            195                 200                 205

His Thr His Tyr Pro Gln Phe Ser Gly Gln Ser Phe Ala Glu Arg Ser
                            210                 215                 220

Gly Arg Gly Pro Phe Gly Asp Ser Leu Met Glu Leu Asp Ala Ala Val
            225                 230                 235                 240
```

```
Gly Thr Leu Met Thr Ala Ile Gly Asp Leu Gly Leu Glu Glu Thr
                    245                 250                 255

Leu Val Ile Phe Thr Ala Asp Asn Gly Pro Glu Thr Met Arg Met Ser
                260                 265                 270

Arg Gly Gly Cys Ser Gly Leu Leu Arg Cys Gly Lys Gly Thr Thr Tyr
                275                 280                 285

Glu Gly Gly Val Arg Glu Pro Ala Leu Ala Phe Trp Pro Gly His Ile
            290                 295                 300

Ala Pro Gly Val Thr His Glu Leu Ala Ser Ser Leu Asp Leu Leu Pro
305                 310                 315                 320

Thr Leu Ala Ala Leu Ala Gly Ala Pro Leu Pro Asn Val Thr Leu Asp
                325                 330                 335

Gly Phe Asp Leu Ser Pro Leu Leu Leu Gly Thr Gly Lys Ser Pro Arg
                340                 345                 350

Gln Ser Leu Phe Phe Tyr Pro Ser Tyr Pro Asp Glu Val Arg Gly Val
                355                 360                 365

Phe Ala Val Arg Thr Gly Lys Tyr Lys Ala His Phe Phe Thr Gln Gly
            370                 375                 380

Ser Ala His Ser Asp Thr Thr Ala Asp Pro Ala Cys His Ala Ser Ser
385                 390                 395                 400

Ser Leu Thr Ala His Glu Pro Pro Leu Leu Tyr Asp Leu Ser Lys Asp
                405                 410                 415

Pro Gly Glu Asn Tyr Asn Leu Leu Gly Gly Val Ala Gly Ala Thr Pro
                420                 425                 430

Glu Val Leu Gln Ala Leu Lys Gln Leu Gln Leu Leu Lys Ala Gln Leu
            435                 440                 445

Asp Ala Ala Val Thr Phe Gly Pro Ser Gln Val Ala Arg Gly Glu Asp
                450                 455                 460

Pro Ala Leu Gln Ile Cys Cys His Pro Gly Cys Thr Pro Arg Pro Ala
465                 470                 475                 480

Cys Cys His Cys Pro Asp Pro His Ala
                485

<210> SEQ ID NO 20
<211> LENGTH: 489
<212> TYPE: PRT
<213> ORGANISM: Homo sapiens

<400> SEQUENCE: 20

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
                20                  25                  30

Gln Leu Ala Ala Gly Gly Leu Arg Phe Thr Asp Phe Tyr Val Pro Val
            35                  40                  45

Ser Leu Cys Thr Pro Ser Arg Ala Ala Leu Leu Thr Gly Arg Leu Pro
        50                  55                  60

Val Arg Met Gly Met Tyr Pro Gly Val Leu Val Pro Ser Ser Arg Gly
65              70                  75                  80

Gly Leu Pro Leu Glu Glu Val Thr Val Ala Glu Val Leu Ala Ala Arg
                85                  90                  95

Gly Tyr Leu Thr Gly Met Ala Gly Lys Trp His Leu Gly Val Gly Pro
            100                 105                 110

Glu Gly Ala Phe Leu Pro Pro His Gln Gly Phe His Arg Phe Leu Gly
```

```
            115                 120                 125
Ile Pro Tyr Ser His Asp Gln Gly Pro Cys Gln Asn Leu Thr Cys Phe
130                 135                 140

Pro Pro Ala Thr Pro Cys Asp Gly Gly Cys Asp Gln Gly Leu Val Pro
145                 150                 155                 160

Ile Pro Leu Leu Ala Asn Leu Ser Val Glu Ala Gln Pro Pro Trp Leu
                165                 170                 175

Pro Gly Leu Glu Ala Arg Tyr Met Ala Phe Ala His Asp Leu Met Ala
            180                 185                 190

Asp Ala Gln Arg Gln Asp Arg Pro Phe Phe Leu Tyr Tyr Ala Ser His
        195                 200                 205

His Thr His Tyr Pro Gln Phe Ser Gly Gln Ser Phe Ala Glu Arg Ser
    210                 215                 220

Gly Arg Gly Pro Phe Gly Asp Ser Leu Met Leu Asp Ala Ala Val
225                 230                 235                 240

Gly Thr Leu Met Thr Ala Ile Gly Asp Leu Gly Leu Leu Glu Glu Thr
                245                 250                 255

Leu Val Ile Phe Thr Ala Asp Asn Gly Pro Glu Thr Met Arg Met Ser
            260                 265                 270

Arg Gly Gly Cys Ser Gly Leu Leu Arg Cys Gly Lys Gly Thr Thr Tyr
        275                 280                 285

Glu Gly Gly Val Arg Glu Pro Ala Leu Ala Phe Trp Pro Gly His Ile
    290                 295                 300

Ala Pro Gly Val Thr His Glu Leu Ala Ser Ser Leu Asp Leu Leu Pro
305                 310                 315                 320

Thr Leu Ala Ala Leu Ala Gly Ala Pro Leu Pro Asn Val Thr Leu Asp
                325                 330                 335

Gly Phe Asp Leu Ser Pro Leu Leu Leu Gly Thr Gly Lys Ser Pro Arg
            340                 345                 350

Gln Ser Leu Phe Phe Tyr Pro Ser Tyr Pro Asp Glu Val Arg Gly Val
        355                 360                 365

Phe Ala Val Arg Thr Gly Lys Tyr Lys Ala His Phe Phe Thr Gln Gly
    370                 375                 380

Ser Ala His Ser Asp Thr Thr Ala Asp Pro Ala Cys His Ala Ser Ser
385                 390                 395                 400

Ser Leu Thr Ala His Glu Pro Pro Leu Leu Tyr Asp Leu Ser Lys Asp
                405                 410                 415

Pro Gly Glu Asn Tyr Asn Leu Leu Gly Gly Val Ala Gly Ala Thr Pro
            420                 425                 430

Glu Val Leu Gln Ala Leu Lys Gln Leu Gln Leu Leu Lys Ala Gln Leu
        435                 440                 445

Asp Ala Ala Val Thr Phe Gly Pro Ser Gln Val Ala Arg Gly Glu Asp
    450                 455                 460

Pro Ala Leu Gln Ile Cys Cys His Pro Gly Cys Thr Pro Arg Pro Ala
465                 470                 475                 480

Cys Cys His Cys Pro Asp Pro His Ala
                485
```

<210> SEQ ID NO 21
<211> LENGTH: 1011
<212> TYPE: PRT
<213> ORGANISM: Homo sapiens

<400> SEQUENCE: 21

```
Met Gly Ala Tyr Ala Arg Ala Ser Gly Val Cys Ala Arg Gly Cys Leu
1               5                   10                  15

Asp Ser Ala Gly Pro Trp Thr Met Ser Arg Ala Leu Arg Pro Pro Leu
            20                  25                  30

Pro Pro Leu Cys Phe Phe Leu Leu Leu Ala Ala Ala Gly Ala Arg
            35                  40                  45

Ala Gly Gly Tyr Glu Thr Cys Pro Thr Val Gln Pro Asn Met Leu Asn
        50                  55                  60

Val His Leu Leu Pro His Thr His Asp Asp Val Gly Trp Leu Lys Thr
65                  70                  75                  80

Val Asp Gln Tyr Phe Tyr Gly Ile Lys Asn Asp Ile Gln His Ala Gly
                85                  90                  95

Val Gln Tyr Ile Leu Asp Ser Val Ile Ser Ala Leu Leu Ala Asp Pro
            100                 105                 110

Thr Arg Arg Phe Ile Tyr Val Glu Ile Ala Phe Phe Ser Arg Trp Trp
            115                 120                 125

His Gln Gln Thr Asn Ala Thr Gln Glu Val Val Arg Asp Leu Val Arg
        130                 135                 140

Gln Gly Arg Leu Glu Phe Ala Asn Gly Gly Trp Val Met Asn Asp Glu
145                 150                 155                 160

Ala Ala Thr His Tyr Gly Ala Ile Val Asp Gln Met Thr Leu Gly Leu
            165                 170                 175

Arg Phe Leu Glu Asp Thr Phe Gly Asn Asp Gly Arg Pro Arg Val Ala
            180                 185                 190

Trp His Ile Asp Pro Phe Gly His Ser Arg Glu Gln Ala Ser Leu Phe
        195                 200                 205

Ala Gln Met Gly Phe Asp Gly Phe Phe Phe Gly Arg Leu Asp Tyr Gln
        210                 215                 220

Asp Lys Trp Val Arg Met Gln Lys Leu Glu Met Glu Gln Val Trp Arg
225                 230                 235                 240

Ala Ser Thr Ser Leu Lys Pro Pro Thr Ala Asp Leu Phe Thr Gly Val
            245                 250                 255

Leu Pro Asn Gly Tyr Asn Pro Pro Arg Asn Leu Cys Trp Asp Val Leu
            260                 265                 270

Cys Val Asp Gln Pro Leu Val Glu Asp Pro Arg Ser Pro Glu Tyr Asn
        275                 280                 285

Ala Lys Glu Leu Val Asp Tyr Phe Leu Asn Val Ala Thr Ala Gln Gly
        290                 295                 300

Arg Tyr Tyr Arg Thr Asn His Thr Val Met Thr Met Gly Ser Asp Phe
305                 310                 315                 320

Gln Tyr Glu Asn Ala Asn Met Trp Phe Lys Asn Leu Asp Lys Leu Ile
            325                 330                 335

Arg Leu Val Asn Ala Gln Gln Ala Lys Gly Ser Ser Val His Val Leu
            340                 345                 350

Tyr Ser Thr Pro Ala Cys Tyr Leu Trp Glu Leu Asn Lys Ala Asn Leu
            355                 360                 365

Thr Trp Ser Val Lys His Asp Asp Phe Phe Pro Tyr Ala Asp Gly Pro
        370                 375                 380

His Gln Phe Trp Thr Gly Tyr Phe Ser Ser Arg Pro Ala Leu Lys Arg
385                 390                 395                 400

Tyr Glu Arg Leu Ser Tyr Asn Phe Leu Gln Val Cys Asn Gln Leu Glu
            405                 410                 415

Ala Leu Val Gly Leu Ala Ala Asn Val Gly Pro Tyr Gly Ser Gly Asp
```

-continued

```
            420                 425                 430
Ser Ala Pro Leu Asn Glu Ala Met Ala Val Leu Gln His His Asp Ala
        435                 440                 445

Val Ser Gly Thr Ser Arg Gln His Val Ala Asn Asp Tyr Ala Arg Gln
    450                 455                 460

Leu Ala Ala Gly Trp Gly Pro Cys Glu Val Leu Leu Ser Asn Ala Leu
465                 470                 475                 480

Ala Arg Leu Arg Gly Phe Lys Asp His Phe Thr Phe Cys Gln Gln Leu
                485                 490                 495

Asn Ile Ser Ile Cys Pro Leu Ser Gln Thr Ala Ala Arg Phe Gln Val
            500                 505                 510

Ile Val Tyr Asn Pro Leu Gly Arg Lys Val Asn Trp Met Val Arg Leu
        515                 520                 525

Pro Val Ser Glu Gly Val Phe Val Lys Asp Pro Asn Gly Arg Thr
    530                 535                 540

Val Pro Ser Asp Val Val Ile Phe Pro Ser Ser Asp Ser Gln Ala His
545                 550                 555                 560

Pro Pro Glu Leu Leu Phe Ser Ala Ser Leu Pro Ala Leu Gly Phe Ser
                565                 570                 575

Thr Tyr Ser Val Ala Gln Val Pro Arg Trp Lys Pro Gln Ala Arg Ala
            580                 585                 590

Pro Gln Pro Ile Pro Arg Arg Ser Trp Ser Pro Ala Leu Thr Ile Glu
        595                 600                 605

Asn Glu His Ile Arg Ala Thr Phe Asp Pro Asp Thr Gly Leu Leu Met
    610                 615                 620

Glu Ile Met Asn Met Asn Gln Gln Leu Leu Leu Pro Val Arg Gln Thr
625                 630                 635                 640

Phe Phe Trp Tyr Asn Ala Ser Ile Gly Asp Asn Glu Ser Asp Gln Ala
                645                 650                 655

Ser Gly Ala Tyr Ile Phe Arg Pro Asn Gln Gln Lys Pro Leu Pro Val
            660                 665                 670

Ser Arg Trp Ala Gln Ile His Leu Val Lys Thr Pro Leu Val Gln Glu
        675                 680                 685

Val His Gln Asn Phe Ser Ala Trp Cys Ser Gln Val Val Arg Leu Tyr
    690                 695                 700

Pro Gly Gln Arg His Leu Glu Leu Glu Trp Ser Val Gly Pro Ile Pro
705                 710                 715                 720

Val Gly Asp Thr Trp Gly Lys Glu Val Ile Ser Arg Phe Asp Thr Pro
                725                 730                 735

Leu Glu Thr Lys Gly Arg Phe Tyr Thr Asp Ser Asn Gly Arg Glu Ile
            740                 745                 750

Leu Glu Arg Arg Arg Asp Tyr Arg Pro Thr Trp Lys Leu Asn Gln Thr
        755                 760                 765

Glu Pro Val Ala Gly Asn Tyr Tyr Pro Val Asn Thr Arg Ile Tyr Ile
    770                 775                 780

Thr Asp Gly Asn Met Gln Leu Thr Val Leu Thr Asp Arg Ser Gln Gly
785                 790                 795                 800

Gly Ser Ser Leu Arg Asp Gly Ser Leu Glu Leu Met Val His Arg Arg
                805                 810                 815

Leu Leu Lys Asp Asp Gly Arg Gly Val Ser Glu Pro Leu Met Glu Asn
            820                 825                 830

Gly Ser Gly Ala Trp Val Arg Gly Arg His Leu Val Leu Leu Asp Thr
        835                 840                 845
```

```
Ala Gln Ala Ala Ala Ala Gly His Arg Leu Leu Ala Glu Gln Glu Val
850                 855                 860

Leu Ala Pro Gln Val Val Leu Ala Pro Gly Gly Gly Ala Ala Tyr Asn
865                 870                 875                 880

Leu Gly Ala Pro Pro Arg Thr Gln Phe Ser Gly Leu Arg Arg Asp Leu
                885                 890                 895

Pro Pro Ser Val His Leu Leu Thr Leu Ala Ser Trp Gly Pro Glu Met
            900                 905                 910

Val Leu Leu Arg Leu Glu His Gln Phe Ala Val Gly Glu Asp Ser Gly
        915                 920                 925

Arg Asn Leu Ser Ala Pro Val Thr Leu Asn Leu Arg Asp Leu Phe Ser
    930                 935                 940

Thr Phe Thr Ile Thr Arg Leu Gln Glu Thr Thr Leu Val Ala Asn Gln
945                 950                 955                 960

Leu Arg Glu Ala Ala Ser Arg Leu Lys Trp Thr Thr Asn Thr Gly Pro
                965                 970                 975

Thr Pro His Gln Thr Pro Tyr Gln Leu Asp Pro Ala Asn Ile Thr Leu
            980                 985                 990

Glu Pro Met Glu Ile Arg Thr Phe Leu Ala Ser Val Gln Trp Lys Glu
        995                 1000                1005

Val Asp Gly
    1010

<210> SEQ ID NO 22
<211> LENGTH: 8079
<212> TYPE: DNA
<213> ORGANISM: Artificial Sequence
<220> FEATURE:
<223> OTHER INFORMATION: Description of Artificial Sequence: Synthetic
      expression plasmid pLamanExp1

<400> SEQUENCE: 22
agatcttcaa tattggccat tagccatatt attcattggt tatatagcat aaatcaatat    60
tggctattgg ccattgcata cgttgtatct atatcataat atgtacattt atattggctc   120
atgtccaata tgaccgccat gttggcattg attattgact agttattaat agtaatcaat   180
tacggggtca ttagttcata gcccatatat ggagttccgc gttacataac ttacggtaaa   240
tggcccgcct ggctgaccgc ccaacgaccc ccgcccattg acgtcaataa tgacgtatgt   300
tcccatagta acgccaatag ggactttcca ttgacgtcaa tgggtggagt atttacggta   360
aactgcccac ttggcagtac atcaagtgta tcatatgcca gtccgcccc ctattgacgt    420 caatgacggt aaatggcccg cctggcatta tgcccagtac atgaccttac gggactttcc   480
tacttggcag tacatctacg tattagtcat cgctattacc atggtgatgc ggttttggca   540
gtacaccaat gggcgtggat agcggtttga ctcacgggga tttccaagtc tccaccccat   600
tgacgtcaat gggagtttgt tttggcacca aaatcaacgg gactttccaa aatgtcgtaa   660
caactgcgat cgcccgcccc gttgacgcaa atgggcggta ggcgtgtacg gtgggaggtc   720
tatataagca gagctcgttt agtgaaccgt cagatcacta gaagcttat tgcggtagtt    780 tatcacagtt aaattgctaa cgcagtcagt gcttctgaca acagtctc gaacttaagc     840 tgcagtgact ctcttaaggt agccttgcag aagttggtcg tgaggcactg gcaggtaag    900 tatcaaggtt acaagacagg tttaaggaga ccaatagaaa ctgggcttgt cgagacagag   960
aagactcttg cgtttctgat aggcacctat tggtcttact gacatccact ttgcctttct  1020
```

```
ctccacaggt gtccactccc agttcaatta cagctcttaa ggctagagta cttaatacga   1080
ctcactatag gctagcctcg agaattcgcc gccatgggcg cctacgcgcg ggcttcgggg   1140
gtctgcgctc gaggctgcct ggactcagca ggcccctgga ccatgtcccg cgccctgcgg   1200
ccaccgctcc cgcctctctg cttttttcct tttgttgctgg cggctgccgg tgctcgggcc   1260
gggggatacg agacatgccc cacagtgcag ccgaacatgc tgaacgtgca cctgctgcct   1320
cacacacatg atgacgtggg ctggctcaaa accgtggacc agtacttttta tggaatcaag   1380
aatgacatcc agcacgccgg tgtgcagtac atcctggact cggtcatctc tgccttgctg   1440
gcagatccca cccgtcgctt catttacgtg gagattgcct tcttctcccg ttggtggcac   1500
cagcagacaa atgccacaca ggaagtcgtg cgagaccttg tgcgccaggg gcgcctggag   1560
ttcgccaatg gtggctgggt gatgaacgat gaggcagcca cccactacgg tgccatcgtg   1620
gaccagatga cacttgggct cgctttctg gaggacacat ttggcaatga tgggcgaccc   1680
cgtgtggcct ggcacattga ccccttcggc cactctcggg agcaggcctc gctgtttgcg   1740
cagatgggct tcgacggctt cttctttggg cgccttgatt atcaagataa gtgggtacgg   1800
atgcagaagc tggagatgga gcaggtgtgg cgggccagca ccagcctgaa gcccccgacc   1860
gcggacctct tcactggtgt gcttcccaat ggttacaacc cgccaaggaa tctgtgctgg   1920
gatgtgctgt gtgtcgatca gccgctggtg gaggaccctc gcagccccga gtacaacgcc   1980
aaggagctgg tcgattactt cctaaatgtg gccactgccc agggccggta ttaccgcacc   2040
aaccacactg tgatgaccat gggctcggac ttccaatatg agaatgccaa catgtggttc   2100
aagaaccttg acaagctcat ccggctggta aatgcgcagc aggcaaaagg aagcagtgtc   2160
catgttctct actccacccc cgcttgttac ctctgggagc tgaacaaggc caacctcacc   2220
tggtcagtga acatgacga cttcttccct tacgcggatg gccccacca gttctggacc   2280
ggttactttt ccagtcggcc ggccctcaaa cgctacgagc gcctcagcta caacttcctg   2340
caggtgtgca accagctgga ggcgctggtg ggcctggcgg ccaacgtggg accctatggc   2400
tccggagaca gtgcacccct caatgaggcg atggctgtgc tccagcatca cgacgccgtc   2460
agcggcacct cccgccagca cgtggccaac gactacgcgc gccagcttgc ggcaggctgg   2520
gggccttgcg aggttcttct gagcaacgcg ctggcgcggc tcagaggctt caaagatcac   2580
ttcaccttt gccaacagct aaacatcagc atctgcccgc tcagccagac ggcggcgcgc   2640
ttccaggtca tcgtttataa tcccctgggg cggaaggtga attggatggt acggctgccg   2700
gtcagcgaag gcgttttcgt tgtgaaggac cccaatggca ggacagtgcc cagcgatgtg   2760
gtaatatttc ccagctcaga cagccaggcg caccctccgg agctgctgtt ctcagcctca   2820
ctgcccgccc tgggcttcag cacctattca gtagcccagg tgcctcgctg gaagcccag   2880
gcccgcgcac cacagcccat ccccagaaga tcctggtccc ctgctttaac catcgaaaat   2940
gagcacatcc gggcaacgtt tgatcctgac acagggctgt tgatggagat tatgaacatg   3000
aatcagcaac tcctgctgcc tgttcgccag accttcttct ggtacaacgc cagtataggt   3060
gacaacgaaa gtgaccaggc ctcaggtgcc tacatcttca gacccaacca acagaaaccg   3120
ctgcctgtga gccgctgggc tcagatccac ctggtgaaga caccccttggt gcaggaggtg   3180
caccagaact tctcagcttg gtgttcccag gtggttcgcc tgtacccagg acagcggcac   3240
ctggagctag agtggtcggt ggggccgata cctgtgggcg acacctgggg gaaggaggtc   3300
atcagccgtt ttgacacacc gctggagaca aaggacgcgt tctacacaga cagcaatggc   3360
cgggagatcc tggagaggag gcgggattat cgacccacct ggaaactgaa ccagacggag   3420
```

```
cccgtggcag gaaactacta tccagtcaac acccggattt acatcacgga tggaaacatg    3480
cagctgactg tgctgactga ccgctcccag gggggcagca gcctgagaga tggctcgctg    3540
gagctcatgg tgcaccgaag gctgctgaag gacgatggac gcggagtatc ggagccacta    3600
atggagaacg ggtcggggc gtgggtgcga gggcgccacc tggtgctgct ggacacagcc     3660
caggctgcag ccgccggaca ccggctcctg gcggagcagg aggtcctggc ccctcaggtg    3720
gtgctggccc cgggtggcgg cgccgcctac aatctcgggg ctcctccgcg cacgcagttc    3780
tcagggctgc gcaggga cct gccgccctcg gtgcacctgc tcacgctggc cagctggggc    3840
cccgaaatgg tgctgctgcg cttggagcac cagtttgccg taggagagga ttccggacgt    3900
aacctgagcg cccccgttac cttgaacttg agggacctgt tctccacctt caccatcacc    3960
cgcctgcagg agaccacgct ggtggccaac cagctccgcg aggcagcctc caggctcaag    4020
tggacaacaa acacaggccc cacaccccac caaactccgt accagctgga cccggccaac    4080
atcacgctgg aacccatgga aatccgcact ttcctggcct cagttcaatg gaaggaggtg    4140
gatggttagg tctgctggga tgggccctct agagtcgacc cggcggccg cttccctttta    4200 gtgagggtta atgcttcgag cagacatgat aagatacatt gatgagtttg acaaaccac    4260 aactagaatg cagtgaaaaa aatgctttat ttgtgaaatt tgtgatgcta ttgctttatt    4320
tgtaaccatt ataagctgca ataaacaagt taacaacaac aattgcattc attttatgtt    4380
tcaggttcag ggggagatgt gggaggtttt ttaaagcaag taaaacctct acaaatgtgg    4440
taaaatccga taaggatcga tccgggctgg cgtaatagcg aagaggcccg caccgatcgc    4500
ccttcccaac agttgcgcag cctgaatggc gaatggacgc gccctgtagc ggcgcattaa    4560
gcgcggcggg tgtggtggtt acgcgcagcg tgaccgctac acttgccagc gccctagcgc    4620
ccgctccttt cgctttcttc ccttcctttc tcgccacgtt cgccggcttt ccccgtcaag    4680
ctctaaatcg ggggctccct ttagggttcc gatttagagc tttacggcac ctcgaccgca    4740
aaaaacttga tttgggtgat ggttcacgta gtgggccatc gccctgatag acggtttttc    4800
gccctttgac gttggagtcc acgttcttta atagtggact cttgttccaa actggaacaa    4860
cactcaaccc tatctcggtc tattcttttg atttataagg gattttgggg atttcggcct    4920
attggttaaa aaatgagctg atttaacaaa aatttaacgc gaattaattc tgtggaatgt    4980
gtgtcagtta gggtgtggaa agtccccagg ctccccaggc aggcagaagt atgcaaagca    5040
tgcatctcaa ttagtcagca accaggtgtg gaaagtcccc aggctcccca gcaggcagaa    5100
gtatgcaaag catgcatctc aattagtcag caaccatagt cccgccccta actccgccca    5160
tcccgcccct aactccgccc agttccgccc attctccgcc ccatggctga ctaatttttt    5220
ttatttatgc agaggccgag gccgcctctg cctctgagct attccagaag tagtgaggag    5280
gcttttttgg aggcctaggc ttttgcaaaa agctcccggg atggtcgac cattgaactg     5340 catcgtcgcc gtgtcccaaa atatggggat tggcaagaac ggagacctac cctgcctcc     5400 gctcaggaac gagttcaagt acttccaaag aatgaccaca acctcttcag tggaaggtaa    5460
acagaatctg gtgattatgg gtaggaaaac ctggttctcc attcctgaga agaatcgacc    5520
tttaaaggac agaattaata tagttctcag tagagaactc aaagaaccac cacgaggagc    5580
tcattttctt gccaaaagtt tggatgatgc cttaagactt attgaacaac cggaattggc    5640
aagtaaagta gacatggttt ggatagtcgg aggcagttct gtttaccagg aagccatgaa    5700
tcaaccaggc caccttagac tctttgtgac aaggatcatg caggaatttg aaagtgacac    5760
```

```
gttttttccca gaaattgatt tgggaaaata taaacttctc ccagaatacc caggcgtcct    5820
ctctgaggtc caggaggaaa aaggcatcaa gtataagttt gaagtctacg agaagaaaga    5880
ctaattcgaa atgaccgacc aagcgacgcc caacctgcca tcacgatggc cgcaataaaa    5940
tatctttatt ttcattacat ctgtgtgttg gttttttgtg tgaatcgata gcgataagga    6000
tccgcgtatg gtgcactctc agtacaatct gctctgatgc cgcatagtta agccagcccc    6060
gacacccgcc aacacccgct gacgcgccct gacgggcttg tctgctcccg gcatccgctt    6120
acagacaagc tgtgaccgtc tccgggagct gcatgtgtca gaggttttca ccgtcatcac    6180
cgaaacgcgc gagacgaaag ggcctcgtga tacgcctatt tttataggtt aatgtcatga    6240
taataatggt ttcttagacg tcaggtggca cttttcgggg aaatgtgcgc ggaaccccta    6300
tttgtttatt tttctaaata cattcaaata tgtatccgct catgagacaa taaccctgat    6360
aaatgcttca ataatattga aaaaggaaga gtatgagtat tcaacatttc cgtgtcgccc    6420
ttattccctt ttttgcggca ttttgccttc ctgttttttgc tcacccagaa acgctggtga    6480
aagtaaaaga tgctgaagat cagttgggtg cacgagtggg ttacatcgaa ctggatctca    6540
acagcggtaa gatccttgag agttttcgcc ccgaagaacg ttttccaatg atgagcactt    6600
ttaaagttct gctatgtggc gcggtattat cccgtattga cgccgggcaa gagcaactcg    6660
gtcgccgcat acactattct cagaatgact tggttgagta ctcaccagtc acagaaaagc    6720
atcttacgga tggcatgaca gtaagagaat tatgcagtgc tgccataacc atgagtgata    6780
acactgcggc caacttactt ctgacaacga tcggaggacc gaaggagcta accgcttttt    6840
tgcacaacat gggggatcat gtaactcgcc ttgatcgttg ggaaccggag ctgaatgaag    6900
ccataccaaa cgacgagcgt gacaccacga tgcctgtagc aatggcaaca acgttgcgca    6960
aactattaac tggcgaacta cttactctag cttcccggca acaattaata gactggatgg    7020
aggcggataa agttgcagga ccacttctgc gctcggccct tccggctggc tggtttattg    7080
ctgataaatc tggagccggt gagcgtgggt ctcgcggtat cattgcagca ctggggccag    7140
atggtaagcc ctcccgtatc gtagttatct acacgacggg gagtcaggca actatggatg    7200
aacgaaatag acagatcgct gagataggtg cctcactgat taagcattgg taactgtcag    7260
accaagttta ctcatatata ctttagattg atttaaaact tcatttttaa tttaaaagga    7320
tctaggtgaa gatcctttt gataatctca tgaccaaaat cccttaacgt gagttttcgt    7380
tccactgagc gtcagacccc gtagaaaaga tcaaaggatc ttcttgagat ccttttttc    7440
tgcgcgtaat ctgctgcttg caaacaaaaa aaccaccgct accagcggtg gtttgtttgc    7500
cggatcaaga gctaccaact cttttttccga aggtaactgg cttcagcaga gcgcagatac    7560
caaatactgt ccttctagtg tagccgtagt taggccacca cttcaagaac tctgtagcac    7620
cgcctacata cctcgctctg ctaatcctgt taccagtggc tgctgccagt ggcgataagt    7680
cgtgtcttac cgggttggac tcaagacgat agttaccgga taaggcgcag cggtcgggct    7740
gaacggggggg ttcgtgcaca cagcccagct tggagcgaac gacctacacc gaactgagat    7800
acctacagcg tgagctatga gaaagcgcca cgcttcccga agggagaaag gcggacaggt    7860
atccggtaag cggcagggtc ggaacaggag agcgcacgag ggagcttcca gggggaaacg    7920
cctggtatct ttatagtcct gtcgggtttc gccacctctg acttgagcgt cgatttttgt    7980
gatgctcgtc agggggggcgg agcctatgga aaaacgccag caacgcggcc tttttacggt    8040
tcctggcctt ttgctggcct tttgctcaca tggctcgac                          8079
```

<210> SEQ ID NO 23
<211> LENGTH: 3761
<212> TYPE: DNA
<213> ORGANISM: Homo sapiens

<400> SEQUENCE: 23

| | | | | | | |
|---|---|---|---|---|---|---|
| ggctactctc | ggcttcctgg | caacgccgag | cgaaagctat | gactgcggcc | gcgggttcgg | 60 |
| cgggccgcgc | cgcggtgccc | ttgctgctgt | gtgcgctgct | ggcgcccggc | ggcgcgtacg | 120 |
| tgctcgacga | ctccgacggg | ctgggccggg | agttcgacgg | catcggcgcg | gtcagcggcg | 180 |
| gcggggcaac | ctcccgactt | ctagtaaatt | acccagagcc | ctatcgttct | cagatattgg | 240 |
| attatctctt | taagccgaat | tttggtgcct | ctttgcatat | tttaaaagtg | gaaataggtg | 300 |
| gtgatgggca | gacaacagac | ggcactgagc | cctcccacat | gcattatgca | ctagatgaga | 360 |
| attatttccg | aggatacgag | tggtggttga | tgaaagaagc | taagaagagg | aatcccaata | 420 |
| ttacactcat | tgggttgcca | tggtcattcc | ctggatggct | gggaaaaggt | ttcgactggc | 480 |
| cttatgtcaa | tcttcagctg | actgccatt | atgtcgtgac | ctggattgtg | ggcgccaagc | 540 |
| gttaccatga | tttggacatt | gattatattg | gaatttggaa | tgagaggtca | tataatgcca | 600 |
| attatattaa | gatattaaga | aaaatgctga | attatcaagg | tctccagcga | gtgaaaatca | 660 |
| tagcaagtga | taatctctgg | gagtccatct | ctgcatccat | gctccttgat | gccgaactct | 720 |
| tcaaggtggt | tgatgttata | ggggctcatt | atcctggaac | ccattcagca | aaagatgcaa | 780 |
| agttgactgg | gaagaagctt | tggtcttctg | aagactttag | cactttaaat | agtgacatgg | 840 |
| gtgcaggctg | ctggggtcgc | attttaaatc | agaattatat | caatggctat | atgacttcca | 900 |
| caatcgcatg | gaatttagtg | gctagttact | atgaacagtt | gccttatggg | agatgcgggt | 960 |
| tgatgacggc | ccaagagcca | tggagtgggc | actacgtggt | agaatctcct | gtctgggtat | 1020 |
| cagctcatac | cactcagttt | actcaacctg | gctggtatta | cctgaagaca | gttggccatt | 1080 |
| tagagaaagg | aggaagctac | gtagctctga | ctgatggctt | agggaacctc | accatcatca | 1140 |
| ttgaaaccat | gagtcataaa | cattctaagt | gcatacggcc | atttcttcct | tatttcaatg | 1200 |
| tgtcacaaca | atttgccacc | tttgttctta | agggatcttt | tagtgaaata | ccagagctac | 1260 |
| aggtatggta | taccaaactt | ggaaaaacat | ccgaaagatt | tctttttaag | cagctggatt | 1320 |
| ctctatggct | ccttgacagc | gatggcagtt | tcacactgag | cctgcatgaa | gatgagctgt | 1380 |
| tcacactcac | cactctcacc | actggtcgca | aaggcagcta | cccgcttcct | ccaaaatccc | 1440 |
| agcccttccc | aagtacctat | aaggatgatt | tcaatgttga | ttacccattt | tttagtgaag | 1500 |
| ctccaaactt | tgctgatcaa | actggtgtat | ttgaatattt | tacaaatatt | gaagaccctg | 1560 |
| gcgagcatca | cttcacgcta | cgccaagttc | tcaaccagag | acccattacg | tgggctgccg | 1620 |
| atgcatccaa | cacaatcagt | attataggag | actacaactg | gaccaatctg | actataaagt | 1680 |
| gtgatgtttta | catagagacc | cctgacacag | gaggtgtgtt | cattgcagga | agagtaaata | 1740 |
| aaggtggtat | tttgattaga | agtgccagag | gaatttttctt | ctggattttt | gcaaatggat | 1800 |
| cttacagggt | tacaggtgat | ttagctggat | ggattatata | tgctttagga | cgtgttgaag | 1860 |
| ttacagcaaa | aaaatggtat | acactcacgt | taactattaa | gggtcatttc | gcctctggca | 1920 |
| tgctgaatga | caagtctctg | tggacagaca | tccctgtgaa | ttttccaaag | aatggctggg | 1980 |
| ctgcaattgg | aactcactcc | tttgaatttg | cacagtttga | caactttctt | gtggaagcca | 2040 |
| cacgctaata | cttaacaggg | catcatgaaa | tactcttggat | tttcttccct | tcttttggt | 2100 |
| tttggttcag | agccaattct | tgtttcattg | gaacagtata | tgaggctttt | gagactaaaa | 2160 |

| | | |
|---|---|---|
| ataatgaaga gtaaaagggg agagaaattt attttaatt tacctgtgg aagattttat | 2220 | |
| tagaattaat ccaagggga aaactggtga atctttaaca ttacctggtg tgttccctaa | 2280 | |
| cattcaaact gtgcattggc catacccta ggagtggttt gagtagtaca gacctcgaag | 2340 | |
| ccttgctgct aacactgagg tagctctctt catcttattt gcaagcggtc ctgtagatgg | 2400 | |
| cagtaacttg atcatcactg agatgtattt atgcatgctg accgtgtgtc caagtgagcc | 2460 | |
| agtgtcttca tcacaagatg atgctgccat aatagaaagc tgaagaacac tagaagtagc | 2520 | |
| tttttgaaaa ccacttcaac ctgttatgct ttatgctcta aaaagtattt ttttattttc | 2580 | |
| cttttaaga tgatactttt gaaatgcagg atatgatgag tgggatgatt ttaaaaacgc | 2640 | |
| ctctttaata aactacctct aacactattt ctgcggtaat agatattagc agattaattg | 2700 | |
| ggttatttgc attatttaat ttttttgatt ccaagttttg gtcttgtaac cactataact | 2760 | |
| ctctgtgaac gtttttccag gtggctggaa gaaggaagaa aacctgatat agccaatgct | 2820 | |
| gttgtagtcg tttcctcagc ctcatctcac tgtgctgtgg tctgtcctca catgtgcact | 2880 | |
| ggtaacagac tcacacagct gatgaatgct tttctctcct tatgtgtgga aggaggggag | 2940 | |
| cacttagaca tttgctaact cccagaattg gatcatctcc taagatgtac ttactttta | 3000 | |
| aagtccaaat atgtttatat ttaaatatac gtgagcatgt tcatcatgtt gtatgattta | 3060 | |
| tactaagcat taatgtggct ctatgtagca aatcagttat tcatgtaggt aaagtaaatc | 3120 | |
| tagaattatt tataagaatt actcattgaa ctaattctac tatttaggaa tttataagag | 3180 | |
| tctaacatag gcttagctac agtgaagttt tgcattgctt ttgaagacaa gaaaagtgct | 3240 | |
| agaataaata agattacaga gaaatttttt tgttaaaaacc aagtgatttc cagctgatgt | 3300 | |
| atctaatatt ttttaaaaca aacattatag aggtgtaatt tatttacaat aaaatgttcc | 3360 | |
| tactttaaat atacaattca gtgagttttg ataaattgat ataccatgt aaccaacact | 3420 | |
| ccagtcaagc ttcagaatat ttccatcacc ccagaaggtt ctcttgtata cctgctcagt | 3480 | |
| cagttccttt cactcccaat tgttggcagc cattgatagg aattctatca ctataggtta | 3540 | |
| gttttctttg ttccagaaca tcatgaaagc ggcgtcatgt actgtgtatt cttatgaatg | 3600 | |
| gtttctttcc atcagcataa tgatttgaga ttggtccatg ttgtgtgatt cagtggtttg | 3660 | |
| ttccttctta tttctgaaga gttttccatt gtatgaatat accacaattt gtttcctccc | 3720 | |
| caccagtttc tgatactaca attaaaactg tctacattta c | 3761 | |

<210> SEQ ID NO 24
<211> LENGTH: 669
<212> TYPE: PRT
<213> ORGANISM: Homo sapiens

<400> SEQUENCE: 24

Met Thr Ala Ala Ala Gly Ser Ala Gly Arg Ala Ala Val Pro Leu Leu
1               5                   10                  15

Leu Cys Ala Leu Leu Ala Pro Gly Gly Ala Tyr Val Leu Asp Asp Ser
            20                  25                  30

Asp Gly Leu Gly Arg Glu Phe Asp Gly Ile Gly Ala Val Ser Gly Gly
        35                  40                  45

Gly Ala Thr Ser Arg Leu Leu Val Asn Tyr Pro Glu Pro Tyr Arg Ser
    50                  55                  60

Gln Ile Leu Asp Tyr Leu Phe Lys Pro Asn Phe Gly Ala Ser Leu His
65                  70                  75                  80

Ile Leu Lys Val Glu Ile Gly Gly Asp Gly Gln Thr Thr Asp Gly Thr
                85                  90                  95

```
Glu Pro Ser His Met His Tyr Ala Leu Asp Glu Asn Tyr Phe Arg Gly
            100                 105                 110

Tyr Glu Trp Trp Leu Met Lys Glu Ala Lys Lys Arg Asn Pro Asn Ile
            115                 120                 125

Thr Leu Ile Gly Leu Pro Trp Ser Phe Pro Gly Trp Leu Gly Lys Gly
        130                 135                 140

Phe Asp Trp Pro Tyr Val Asn Leu Gln Leu Thr Ala Tyr Tyr Val Val
145                 150                 155                 160

Thr Trp Ile Val Gly Ala Lys Arg Tyr His Asp Leu Asp Ile Asp Tyr
                165                 170                 175

Ile Gly Ile Trp Asn Glu Arg Ser Tyr Asn Ala Asn Tyr Ile Lys Ile
            180                 185                 190

Leu Arg Lys Met Leu Asn Tyr Gln Gly Leu Gln Arg Val Lys Ile Ile
        195                 200                 205

Ala Ser Asp Asn Leu Trp Glu Ser Ile Ser Ala Ser Met Leu Leu Asp
    210                 215                 220

Ala Glu Leu Phe Lys Val Val Asp Val Ile Gly Ala His Tyr Pro Gly
225                 230                 235                 240

Thr His Ser Ala Lys Asp Ala Lys Leu Thr Gly Lys Lys Leu Trp Ser
                245                 250                 255

Ser Glu Asp Phe Ser Thr Leu Asn Ser Asp Met Gly Ala Gly Cys Trp
            260                 265                 270

Gly Arg Ile Leu Asn Gln Asn Tyr Ile Asn Gly Tyr Met Thr Ser Thr
        275                 280                 285

Ile Ala Trp Asn Leu Val Ala Ser Tyr Tyr Glu Gln Leu Pro Tyr Gly
    290                 295                 300

Arg Cys Gly Leu Met Thr Ala Gln Glu Pro Trp Ser Gly His Tyr Val
305                 310                 315                 320

Val Glu Ser Pro Val Trp Val Ser Ala His Thr Thr Gln Phe Thr Gln
                325                 330                 335

Pro Gly Trp Tyr Tyr Leu Lys Thr Val Gly His Leu Glu Lys Gly Gly
            340                 345                 350

Ser Tyr Val Ala Leu Thr Asp Gly Leu Gly Asn Leu Thr Ile Ile Ile
        355                 360                 365

Glu Thr Met Ser His Lys His Ser Lys Cys Ile Arg Pro Phe Leu Pro
    370                 375                 380

Tyr Phe Asn Val Ser Gln Gln Phe Ala Thr Phe Val Leu Lys Gly Ser
385                 390                 395                 400

Phe Ser Glu Ile Pro Glu Leu Gln Val Trp Tyr Thr Lys Leu Gly Lys
                405                 410                 415

Thr Ser Glu Arg Phe Leu Phe Lys Gln Leu Asp Ser Leu Trp Leu Leu
            420                 425                 430

Asp Ser Asp Gly Ser Phe Thr Leu Ser Leu His Glu Asp Glu Leu Phe
        435                 440                 445

Thr Leu Thr Thr Leu Thr Thr Gly Arg Lys Gly Ser Tyr Pro Leu Pro
    450                 455                 460

Pro Lys Ser Gln Pro Phe Pro Ser Thr Tyr Lys Asp Asp Phe Asn Val
465                 470                 475                 480

Asp Tyr Pro Phe Phe Ser Glu Ala Pro Asn Phe Ala Asp Gln Thr Gly
                485                 490                 495

Val Phe Glu Tyr Phe Thr Asn Ile Glu Asp Pro Gly Glu His His Phe
            500                 505                 510
```

```
Thr Leu Arg Gln Val Leu Asn Gln Arg Pro Ile Thr Trp Ala Ala Asp
            515                 520                 525

Ala Ser Asn Thr Ile Ser Ile Ile Gly Asp Tyr Asn Trp Thr Asn Leu
        530                 535                 540

Thr Ile Lys Cys Asp Val Tyr Ile Glu Thr Pro Asp Thr Gly Gly Val
545                 550                 555                 560

Phe Ile Ala Gly Arg Val Asn Lys Gly Gly Ile Leu Ile Arg Ser Ala
                565                 570                 575

Arg Gly Ile Phe Phe Trp Ile Phe Ala Asn Gly Ser Tyr Arg Val Thr
                580                 585                 590

Gly Asp Leu Ala Gly Trp Ile Ile Tyr Ala Leu Gly Arg Val Glu Val
            595                 600                 605

Thr Ala Lys Lys Trp Tyr Thr Leu Thr Leu Thr Ile Lys Gly His Phe
        610                 615                 620

Ala Ser Gly Met Leu Asn Asp Lys Ser Leu Trp Thr Asp Ile Pro Val
625                 630                 635                 640

Asn Phe Pro Lys Asn Gly Trp Ala Ala Ile Gly Thr His Ser Phe Glu
                645                 650                 655

Phe Ala Gln Phe Asp Asn Phe Leu Val Glu Ala Thr Arg
                660                 665

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      11 residue basic peptide from HIV TAT protein

<400> SEQUENCE: 25

Tyr Gly Arg Lys Lys Arg Arg Gln Arg Arg Arg
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      TAT peptide

<400> SEQUENCE: 26

Tyr Ala Arg Ala Ala Ala Arg Gln Ala Arg Ala
1               5                   10
```